United States Patent
Fairhead et al.

(10) Patent No.: US 11,732,243 B2
(45) Date of Patent: Aug. 22, 2023

(54) ANTI-BACTERIAL COMPOSITIONS COMPARING LYTIC MODIFIED BACTERIOPHAGE ENGINEERED TO INFECT AND KILL DIFFERENT TARGET BACTERIA

(71) Applicant: PHICO THERAPEUTICS LTD, Cambridge (GB)

(72) Inventors: Heather Fairhead, Histon (GB); Adam Wilkinson, Chrishall (GB)

(73) Assignee: PHICO THERAPEUTICS LTD, Cambridge (GB)

( * ) Notice: Subject to any disclaimer, the term of this patent is extended or adjusted under 35 U.S.C. 154(b) by 1099 days.

(21) Appl. No.: 16/092,096

(22) PCT Filed: Apr. 7, 2017

(86) PCT No.: PCT/EP2017/058470
§ 371 (c)(1),
(2) Date: Oct. 8, 2018

(87) PCT Pub. No.: WO2017/174810
PCT Pub. Date: Oct. 12, 2017

(65) Prior Publication Data
US 2019/0119651 A1    Apr. 25, 2019

(30) Foreign Application Priority Data

Apr. 8, 2016    (GB) .................................... 1606319

(51) Int. Cl.
*C12N 7/00*       (2006.01)
*A61K 35/76*      (2015.01)
(Continued)

(52) U.S. Cl.
CPC ................ *C12N 7/00* (2013.01); *A61K 35/76* (2013.01); *A61K 39/07* (2013.01); *A61K 39/104* (2013.01);
(Continued)

(58) Field of Classification Search
CPC ............ C12N 7/00; C12N 2795/00021; C12N 2795/00031; C12N 2795/00032;
(Continued)

(56) References Cited

U.S. PATENT DOCUMENTS 6,310,191 B1    10/2001 Collins et al.
6,492,161 B1 *  12/2002 Hjorleifsdottir ......... C12N 7/00
                                                           435/235.1
(Continued)

FOREIGN PATENT DOCUMENTS

DE    102010013834    12/2010
EP    1 384 779       1/2004
(Continued)

OTHER PUBLICATIONS

Ackermann, "Classification of Bacteriophages", Chapter 2 of "The Bacteriophages", 2006, Oxford University Press, vol. 2, p. 8-16. (Year: 2006).*

(Continued)

*Primary Examiner* — Gary B Nickol
*Assistant Examiner* — Amelia Nicole Dickens
(74) *Attorney, Agent, or Firm* — Robin L. Teskin; Baker, Donelson, Bearman, Caldwell & Berkowitz PC

(57) ABSTRACT

A modified bacteriophage capable of infecting a plurality of different target bacteria, which bacteriophage includes a toxin gene encoding a toxin protein which is toxic to the target bacteria; wherein the bacteriophage is lytic; and (Continued)

Figure 1A:
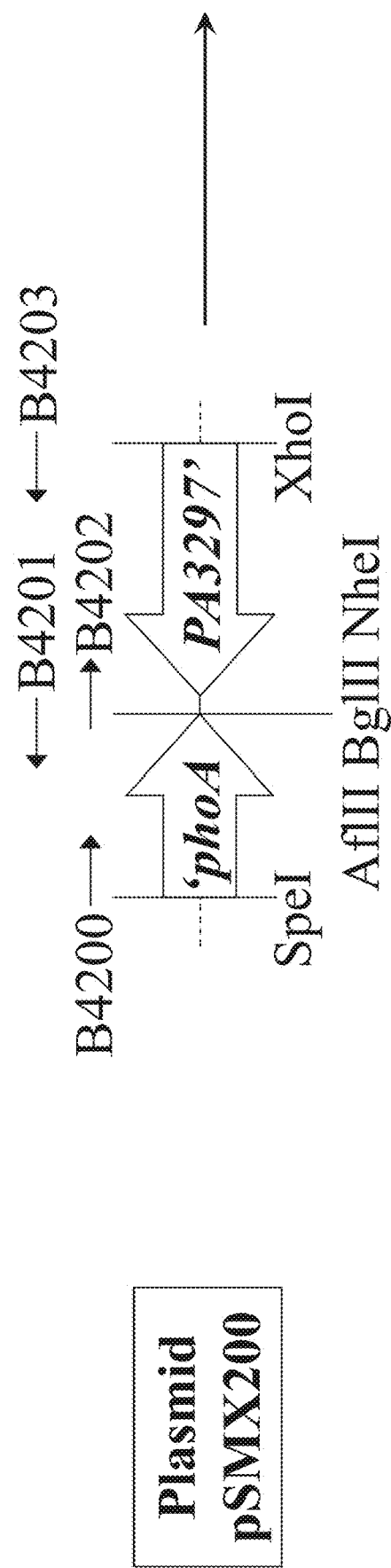

wherein the bacteriophage expresses host range determinant proteins which have a plurality of bacterial host specificities.

11 Claims, 45 Drawing Sheets

Specification includes a Sequence Listing.

(51) Int. Cl.
*A61K 39/07* (2006.01)
*A61K 39/104* (2006.01)

(52) U.S. Cl.
CPC .............. *C12N 2795/00021* (2013.01); *C12N 2795/00031* (2013.01); *C12N 2795/00032* (2013.01); *C12N 2795/00043* (2013.01); *C12N 2795/00045* (2013.01); *C12N 2795/10121* (2013.01); *C12N 2795/10131* (2013.01); *C12N 2795/10132* (2013.01)

(58) Field of Classification Search
CPC ........... C12N 2795/00043; C12N 2795/00045; C12N 2795/10121; C12N 2795/10131; C12N 2795/10132; C12N 2795/00; C12N 2795/101; A61K 35/76; A61K 39/02; A61K 39/07; A61K 39/104
See application file for complete search history.

(56) References Cited

U.S. PATENT DOCUMENTS

| | | | | |
|---|---|---|---|---|
| 7,807,149 | B2* | 10/2010 | Soothill | A61P 27/02 424/170.1 |
| 2004/0097705 | A1* | 5/2004 | Fairhead | A61P 31/04 530/350 |
| 2015/0064770 | A1* | 3/2015 | Lu | C12N 7/00 435/235.1 |
| 2017/0304378 | A1* | 10/2017 | Fairhead | A61K 35/76 |
| 2017/0304379 | A1* | 10/2017 | Fairhead | A61K 35/76 |
| 2017/0306298 | A1* | 10/2017 | Fairhead | A61K 35/74 |
| 2017/0313991 | A1* | 11/2017 | Fairhead | A61P 31/04 |

FOREIGN PATENT DOCUMENTS

| | | |
|---|---|---|
| GB | 2451750 | 2/2009 |
| JP | 2010535482 | 11/2010 |
| WO | 1998/033901 | 8/1998 |
| WO | 2002/007742 | 1/2002 |
| WO | 2002/040678 | 5/2002 |
| WO | 2004/113375 | 12/2004 |
| WO | 2009/019293 | 2/2009 |
| WO | 2010141135 | 12/2010 |
| WO | 2016/055584 | 4/2016 |
| WO | 2016/055585 | 4/2016 |
| WO | 2016/055586 | 4/2016 |
| WO | 2016/055587 | 4/2016 |

OTHER PUBLICATIONS

Veesler et al. "A Common Evolutionary Origin for Tailed-Bacteriophage Functional Modules and Bacterial Machineries", Sep. 2011, Microbiology and Molecular Biology Reviews, vol. 75, No. 3, p. 423-433. (Year: 2011).*
Garbe et al. "Characterization of JG024, a pseudomonas aeruginosa PB1-like broad host range phage under simulated infection conditions", 2010, BMC Microbiology, 10:301, p. 1-10. (Year: 2010).*
Hawkins et al. "Topical treatment of Pseudomonas aeruginosa otitis of dogs with a bacteriophage mixture: A before/after clinical trial", 2010, Veterinary Medicine, vol. 146, p. 309-313. (Year: 2010).*
Ackermann, "Tailed Bacteriophages: The Order Caudovirales", 1999, Advances in Virus Research, vol. 51, p. 135-201. (Year: 1999).*
Quing et al. "Outbreak of PER-1 and diversity of b-lactamases among ceftazidime-resistant Pseudomonas aeruginosa clinical isolates", 2014, Journal of Medical Microbiology, vol. 63, p. 386-392. (Year: 2014).*
Pires et al. "Genetically Engineered Phages: a Review of Advances over the Last Decade", Jun. 1, 2016, Microbiology and Molecular Biology Reviews, vol. 80 No. 3, p. 523-543. (Year: 2016).*
Lin TY, et al. "A T3 and T7 recombinant phage acquires efficient adsorption and a broader host range," PLoS One. 2012;7(2):e30954.
Le S, et al. "Mapping the tail fiber as the receptor binding protein responsible for differential host specificity of Pseudomonas aeruginosa bacteriophages PaP1 and JG004," PLoS One. Jul. 9, 2013;8(7):e68562.
Yoichi M, et al. "Alteration of tail fiber protein gp38 enables T2 phage to infect *Escherichia coli* O157:H7," J Biotechnol. Jan. 12, 2005;115(1):101-7.
Yu P, et al. "Isolation of Polyvalent Bacteriophages by Sequential Multiple-Host Approaches," Appl Environ Microbiol. Nov. 20, 2015;82(3):808-15.
Pitts K. et al.: "SASPject: Efficacy of SASPject against Pseudomonas aeruginosa ATCC 27853 in a Mouse Lung Model", ICAAC 2014 54th Interscience Conference on Antimicrobial Agents and Chemotherapy—Abstract, F-1551, Sep. 8, 2014 (Sep. 8, 2014), XP002752295.

* cited by examiner

Figure 9

>codon_optimised_SASP-C
ATGGCCAACTACCAGAACGCGAGCAACCGCAACAGCAGCAAC
AAGCTGGTCGCGCGGGCGCCCAGGCGCCATCGACCAGATG
AAGTTCGAGATCGCGAGCGAGTTCGGCGAGTTCGGCCCG
GACGCCACGCCCGTGCCAACGGCTCGGTCGGGCGAAATC
ACCAAGCGCCTGGTGCAGCTGGCGGAACAGAACCTGGGCGGC
AAGTACTGA (SEQ. ID. 59)

Figure 13A

```
SPM-1    MITPELIFSPFAAQGDKDFIPQTSSTGFANLRDGYTPDYEISLASNNPQAKAVERRIQRQ  60
F8       MITPELIFSPFAAQGDKDFIPQTSSTGFANLRDGYTPDYEISLASNNPQAKAVERRIQRQ  60
PB1      MITPELIFSPFAAQGDKDFIPQTSSTGFANLRDGYTPDYEISLASNNPQAKAVERRIQRQ  60
C36      MITPELIFSPFAAQGDKDFIPQTSSTGFANLRDGYTPDYEISLASNNPQAKAVERRIQRQ  60
LBL3     MITPELIFSPFAAQGDKDFIPQTSSTGFANLRDGYTPDYEISLASNNPQAKAVERRIQRQ  60
Ph133    MITPELIFSPFAAQGDKDFIPQTSSTGFANLRDGYTPDYEISLASNNPQAKAVERRIQRQ  60
LMA2     MITPELIFSPFAAQGDKDFIPQTSSTGFANLRDGYTPDYEISLASNNPQAKVVERRIQRQ  60
KPP12    MITPELIFSPFAAQGDKDFIPQTSSTGFANLRDGYTPDYEISLASNNPQAKAVERRIQRQ  60
JG024    MITPELIFSPFAAQGDKDFIPQTSSTGFANLRDGYTPDYEISLASNNPQAKAVERRIQRQ  60
PTP92    MITPELIFSPFAAQGDKDFIPQTSSTGFANLRDGYTPDYEISLASNNPQAKAVERRIQRQ  60
NH-4     MITPELIFSPFAAQGDKDFIPQTSSTGFANLRDGYTPDYEISLASNNPQAKAVERRIQRQ  60
14-1     MITPELIFSPFAAQGDKDFIPQTSSTGFANLRDGYTPDYEISLASNNPQAKAVERRIQRQ  60
PTP47    MITPELIFSPFAAQGDKDFIPQTSSTGFANLRDGYTPDYEISLASNNPQAKAVERRIQRQ  60
SN       MITPELIFSPFAAQGDKDFIPQTSSTGFANLRDGYTPDYEISLASNNPQAKAVERRIQRQ  60
         ************************************************.********

SPM-1    LFFIATQNAQAWQPQMAPFWFQGMPGGYEQNAEVVRVGNDGIMRPYRSMVNANASDPLSS  120
F8       LFFIATQNAQAWQPQMAPFWFQGMPGGYEQNAEVVRVGNDGIMRPYRSMVNANASDPLSS  120
PB1      LFFIATQNAQAWQPQMAPFWFQGMPGGYEQNAEVVRVGNDGIMRPYRSMVNANASDPLSS  120
C36      LFFIATQNAQAWQPQMAPFWFQGMPGGYEQNAEVVRVGNDGIMRPYRSMVNANASDPLSS  120
LBL3     LFFIATQNAQAWQPQMAPFWFQGMPGGYEQNAEVVRVGNDGIMRPYRSMVNANASDPLSS  120
Ph133    LFFIATQNAQAWQPQMAPFWFQGMPGGYEQNAEVVRVGNDGIMRPYRSMVNANAIDPLSS  120
LMA2     LFFIATQNAQAWQPQMAPFWFQGMPGGYEQNAEVVRVGNDGIMRPYRSMVNANASDPLSS  120
KPP12    LFFIATQNAQAWQPQMAPFWFQGMPGGYEQNAEVVRVGNDGIMRPYRSMVNANASDPLSS  120
JG024    LFFIATQNAQAWQPQMAPFWFQGMPGGYEQNAEVVRVGNDGIMRPYRSMVNANASDPLSS  120
PTP92    LFFIATQNAQAWQPQMAPFWFQGMPGGYEQNAEVVRVGNDGIMRPYRSMVNANASDPLSS  120
NH-4     LFFIATQNAQAWQPQMAPFWFQGMPGGYERNAEVVRVGNDGIMRPYRSMVNANASDPLSS  120
14-1     LFFIATQNAQAWQPQMAPFWFQGMPGGYEQNAEVVRVGNDGIMRPYRSMVNANASDPLSS  120
PTP47    LFFIATQNAQAWQPQMAPFWFQDMPGGYEQNAEVVRVGNDGIMRPYRSMVNANASDPLSS  120
SN       LFFIATQNAQAWQPQMAPFWFQGMPGGYEQNAEVVRVGNDGIMRPYRSMVNANASDPLSS  120
         *********************.******:***********************.*****

SPM-1    TTWEEQPAWSVMRSNIPMPAGGSGLSSGGEVITTGRNFNDLLNGTWEFFSDSVVASQNA  180
F8       TTWEEQPAWSVMRSNIPMPAGGSGLSSGGEVITTGRNFNDLLNGTWEFFSDSVVAASQNA 180
PB1      TTWEEQPAWSVMRSSIPMPAGGPGLSSGGEVITTGRNFNDLLNGTWEFFSDSVVVASQNA 180
C36      TTWEEQPAWSVMRSSIPMPAGGPGLSSGGEVITTGRNFNDLLNGTWEFFSDSVVVASQNA 180
LBL3     TTWEEQPAWSVMRSSIPMPAGGPGLSSGGEVITTGRNFNDLLNGTWEFFSDSVVIASQNA 180
Ph133    TTWEEQPAWSVMRSNIPMPAGGPGLSSGGEVITTGRNFNDLLNGTWEFFSDSVVVASQNA 180
LMA2     TTWEEQPAWSVMRSNIPMPAGGPGLSSGGEVITTGRNFNDLLNGTWEFFSDSVVIASQNA 180
KPP12    TTWEEQPAWSAMRSNIPMPAGGPGLSSGGEVITTGRNFNDLLNGTWEFFSDSVVIASQNA 180
JG024    TTWEEQPAWSVMRTNIPMPAGGPGLSSGGEVITTGRNFNELLNGTWEFFDAIVVASQNA  180
PTP92    TTWEEQPAWSVMRTNIPMPAGGPGLSSGGEVITTGRNFNELLNGTWEFFDAIVVASQNA  180
NH-4     TTWEEQPAWSVMRTNIPMPAGGPGLSSGGEVITTGRNFNELLNGTWEFFDAIVVASQNA  180
14-1     TTWEEQPAWSVMRSSIPMPAGGPGLSSGGEVITTGRNFNDLLNGTWEFFSDSVVIASQNA 180
PTP47    TTWEEQPAWSAMRSNIPMPAGGPGLSSGGEVITTGRNFNDLLNGTWEFFSDSVVIASQNA 180
SN       TTWEEQPAWSVMRSNIPMPAGGPGLSSGGEVITTGRNFNDLLNGTWEFFSDSVVVASQNA 180
         **********.**:.******.*********************:*********::*****
```

Figure 13B

```
SPM-1   PVYPASAGAAAGMLEAKSWVSGANTFCVQRYTDRVGNVAVPGLNAGAWTNWMYAVNVMAL 240
F8      PVYPASAGAAAGMLEAKSWVSGANTFCVQRYTDRVGNVAVPGLNAGAWTNWMYAVNVMAL 240
PB1     PVYPASAGAAAGMLEAKSWISGSNTFCVQRYTDRVGNVAVPGLNAGAWTNWMYAVNVMAL 240
C36     PVYPASAGAAAGMLEAKSWISGSNTFCVQRYTDRVGNVAVPGLNAGAWTNWMYAVNVMAL 240
LBL3    PVYPASAGAAAGMLEAKSWVSGANTFCVQRYTDRVGNVAVPGLNAGAWTNWMYAVNVMAL 240
Phi33   PVYPASAGAAAGMLEAKSWVSGANTFCVQRYTDRVGNVAVPGLNAGAWTNWMYAVNVMAL 240
LMA2    PVYPASAGAAAGMLEAKSWVSGANTFCVQRYTDRVGNVAVPGLNAGAWTNWMYAVNVMAL 240
KPP12   PVYPASAGAAAGMLEAKSWVSGANTFCVQRYTDRVGNVALPGLNAGAWTNWMYAVNVMAL 240
JG024   PVYPASAGAAAGMLEAKSWVSGSNTFCVQRYTDRVGNVAVPGLNAGAWTNWMYAVNVMAL 240
PTP92   PVYPASAGAAAGMLEAKSWVSGSNTFCVQRYTDRVGNVAVPGLNAGAWTNWMYAVNVMAL 240
NH-4    PVYPASAGAAAGMLEAKSWVSGSNTFCVQRYTDRVGNVAVPGLNAGAWTNWMYAVNVMAL 240
14-1    PVYPASAGAAAGMLEAKSWISRSNTFCVQRYTDRVGNVAVPGLNAGEWTNWMYAVNVMAL 240
PTP47   PVYPASAGAAAGMLEAKSWVSGANTFCVQRYTDRVGNVAVPGLNAGAWTNWMYAVNVMAL 240
SN      PVYPASAGAAAGMLEAKSWVSGANTFCVQRYTDRVGNVAVPGLNAGAWTNWMYAVNVMAL 240
        ****************:* .*****************:****** **************

SPM-1   QQGRVTYGVAAGSANAYTLTLVFQLQGGLVDGMVLRVKFNAMNTGASTINVSGFGSKAIV 300
F8      QQGRVTYGVAAGSANAYTLTLVFQLQGGLVDGMVLRVKFNAMNTGASTINVSGFGSKAIV 300
PB1     QQGRVTYGVAAGSANAYTLTLVFQLQGGLVDGMILRVKFNTVNTGASTINVSGFGAKAIV 300
C36     QQGRVTYGVAAGPANAYTLTLVFQLQGGLVDGMILRVKFNTVNTGASTINVSGFGAKAIV 300
LBL3    QQGRVTYGVAAGSANAYTLTLVFQLQGGLVDGMILRVKFNTMNTGASTINVSGFGAKAIV 300
Phi33   QQGRVTYGVAAGSANAYTLTLVFQLQGGLVDGMILRVKFNTMNTGASTINVSGLGAKAIV 300
LMA2    QQGRVTYGVAAGSANAYTLTLVFQLQGGLVDGMILRVKFNTMNTGATTINVSGLGAKAIV 300
KPP12   QQGRVTYGVAAGSANAYTLTLVFQLQGGLVDGMILRVKFNTMNTGASTINVSGLGAKAIV 300
JG024   QHGRVTYGTAAGPANAYTLTLVFQIQGGLVDGMILRVKFNTMNTGATTINVSGLGAKAIV 300
PTP92   QHGRVTYGTAAGPANAYTLTLVFQIQGGLVDGMILRVKFNTMNTGATTINVSGLGAKAIV 300
NH-4    QHGRVTYGTAAGPANAYTLTLVFQIQGGLVDGMILRVKFNTMNTGATTINVSGLGAKAIV 300
14-1    QQGRVTYGVAAGPANAYTLTLVFQLQGGLVDGMILRVKFNTVNTGASTINVSGLGAKAIV 300
PTP47   QQGRVTYGVAAGSANAYTLTLVFQLQGGLVDGMILRVKFNTMNTGATTINVSGLGAKAIV 300
SN      QQGRVTYGVAAGSANAYTLTLVFQLQGGLVDGMILRVKFNTMNTGASTINVSGLGAKAIV 300
        *:****:.***.************:*********:*****:;****;******.*;****

SPM-1   GAANFPLTGGELGQGLIAELVFDATGDRWPILAGAPRIQVGNADQDYQAPSWKQVKDYVA 360
F8      GAANFPLTGGELGQGLIAELVFDATGDRWPILAGAPRIQVGNADQDYQAPSWKQVKDYVA 360
PB1     GAANFPLTGGELGQGLIAELVFDATGDRWPILAGAPRIQVGNADQDYQAPSWKQVKDYVA 360
C36     GAANFPLTGGELGQGLIAELVFDATGDRWPILAGAPRIQVGNADQDYQAPSWKQVKDYVA 360
LBL3    GAANFPLTGGELGQGLIAELVFDATGDRWPILAGAPRIQVGNADQDYQAPSWKQVKDYVA 360
Phi33   GAANFPLTGGELGQGLIAELVFDAAGDRWPILAGAPRIQVGNADQDYQAPSWKQVKDYVA 360
LMA2    GAANFPLTGGELGQGLIAELVFDAAGDRWRILAGAPRIQVGNADQDYQAPSWKQVKDYVA 360
KPP12   GAANFPLTGGELGQGLIAELVFDAAGDRWRILAGAPRIQVGNADQDYQAPSWKQVKDYVA 360
JG024   GAANFPLTGGELGQGLIAELVFDAAGDRWRILAGAPRIQVGNADQDYQAPSWKQVKDYVE 360
PTP92   GAANFPLTGGELGQGLIAELVFDAAGDRWRILAGAPRIQVGNADQDYQAPSWKQVKDYVE 360
NH-4    GAANFPLTGGELGQGLIAELVFDAAGDRWRILAGAPRIQVGNADQDYQAPSWKQVKDYVA 360
14-1    GAANFPLTGGELGQGLIAELVFDAAGDRWRILAGAPRIQVGNADQDYQAPSWKQVKDYVA 360
PTP47   GAANFPLTGGELGQGLIAELVFDAAGDRWRILAGAPRIQVGNADQDYQAPSWKQVKDYVA 360
SN      GAANFPLTGGELGQGLIAELVFDAAGDRWRILAGAPRIQVGNADQDYQAPSWKQVKDYVA 360
        ************************:*****:***********************:****

SPM-1   SQKLTEVDWADVVNKPNVAIQDTTPWFANLELSDAPPFIDFHFNNNRAKDFDYRFISEAD 420
F8      SQKLTEVDWADVVNKPNVAIQDTTPWFANLELSDAPPFIDFHFNNNRAKDFDYRFISEAD 420
PB1     SQKLTEVDWADVVNKPNVAIQDTTPWFANLELSDAPPFIDFHFNNNRAKDFDYRFISEAD 420
C36     SQKLTEVDWADVVNKPNVAIQDTTPWFANLELSDAPPFIDFHFNNNRAKDFDYRFISEAD 420
LBL3    SQKLTEVDWADVVNKPNVAIQDTTPWFANLELSDAPPFIDFHFNNNRAKDFDYRFISEAD 420
Phi33   SQKLTEVDWADVVNKPNVAIQDTTPWFANLELSDAPPFIDFHFNSNRAKDFDYRLISEAD 420
LMA2    SQKLTEVDWADVVNKPNVAIQDTTPWFANLELSDAPPFIDFHFNSNRAKDFDYRLISEAD 420
KPP12   SQKLTEVDWADVVNKPNVAIQDTTPWFANLELSDAPPFIDFHFNNNRAKDFDYRFISEAD 420
JG024   SQKLTEVDWTDVVNKPNVAIQDTTPWFANLELSDAPPFIDFHFNSNRAKDFDYRLISEAD 420
PTP92   SQKLTEVDWTDVVNKPNVAIQDTTPWFANLELSDAPPFIDFHFNSNRAKDFDYRLISEAD 420
NH-4    SQKLTEVDWTDVVNKPNVAIQDTTPWFANLELSDAPPFIDFHFNSNRAKDFDYRLISEAD 420
14-1    SQKLTEVDWADVVNKPNVAIQDTTPWFANLELSDAPPFIDFHFNSNRAKDFDYRLISEAD 420
PTP47   SQKLTEVDWADVVNKPNVAIQDTTPWFANLELSDAPPFIDFHFNSNRAKDFDYRLISEAD 420
SN      SQKLTEVDWADVVNKPNVAIQDTTPWFANLELSDAPPFIDFHFNSNRAKDFDYRLISEAD 420
        *********:***********************************,*******:*****

SPM-1   GSMAFYSPQGSAGPTQDILFSPSNVTFLQPRLDVAKNLAYIANSGPLWQNTTADQPGWKF 480
F8      GSMAFYSPQGSAGPTQDILFSPSNVTFLQPRLDVAKNLAYIANSGPLWQNTTADQPGWKF 480
```

Figure 13C

```
PB1    GSMAFYSRQGSAGPTQDILFSRSNVTFLQPRLDVAKNLAYIANSGPLWQNTTADQPGWKF 480
C36    GSMAFYSRQGSAGPTQDILFSRSNVTFLQPRLDVAKNLAYIANSGPLWQNTTADQPGWKF 480
LBL3   GSMAFYSRQGSAGPTQDILFSRSNVTFLQPRLDVAKNLAYIANSGPLWQNTTADQPGWKF 480
Ph133  GSLAFYSRQGSAGPTQDILFNRNSVTFFQPRLDVAKNLAYIANSGPLWQNTTADQPGWKF 480
LMA2   GSLAFYSRQGSAGPTQDILFNRNSVTFFQPRLDVAKNLAYIANSGPLWQNTTADQPGWKF 480
KPP12  GSMAFYSRQGSAGPTQDILFSRSNVTFLQPRLDVAKNLAYIANSGSLWQNTTADQPGWKF 480
JG024  GSLAFYSRQGSAGPTQDILFNPNSVTFFQPRLDVAKNLAYIANSGPLWQNTTADQPGWKF 480
PTP92  GSLAFYSRQGSAGPTQDILFNRNSVTFFQPRLDVAKNLAYIANSGPLWQNTTADQPGWKF 480
NH-4   GSLAFYSRQGSAGPTQDILFNRNSVTFFQPRLDVAKNLAYIANSGPLWQNTTADQPGWKF 480
14-1   GSLAFYSRQGSAGPTQDILFNRRSVTFFQPRLDVAKNLAYIANSGPLWQNTTADQPGWKF 480
PTP47  GSLAFYSRQGSAGPTQDILFNRRSVTFFQPRLDVAKNLAYIANSGPLWQNTTADQPGWKF 480
SN     GSLAFYSRQGSAGPTQDILFNRNSVTFFQPRLDVAKNLAYIANSGSLWQNTTADQPGWKF 480
         *:***********:**.*..***:*********************:*************

SPM-1  TFAQGVDANNNAVIAVNFTNPDGSYRSQIMRWDWASTNVIFNNRPLFAGQYVPWDSGNFD 540
F8     TFAQGVDANNNAVIAVNTTNPDGSYRSQIMRWDWASTNVIFNNRPLFAGQYVPWDSGNFD 540
PB1    TFAQGVDANNNAVIAVNTTNPDGSYRSQVMRWDWASTNVIFNNRPLFAGQYVPWDSGNFD 540
C36    TFAQGVDANNNAVIAVNTTNPDGSYRSQIMRWDWASTNVIFNNRPLFAGQYVPWDSGNFD 540
LBL3   TFAQGVDANNNAVIAVNTTNPDGSYRSQIMRWDWASTNVIFNNRPLFAGQYVPWDSGNFD 540
Ph133  TFAQGVDANNNAVIAVNTTNPDGSYRSQIMRWDWASTNVIFNNRPLFAGQYVPWDSGNFD 540
LMA2   TFAQGVDANNNAVIAVNTTNPDGSYRSQVMRWDWASTNVIFNNRPLFAGQYTPWDSGNFD 540
KPP12  TFAQGVDANNNAVIAVNTTNPDGSYRSQIMRWDWASTNVIFNNRPLFAGQYVPWDSGNFD 540
JG024  TFAQGVDANNNAVIAVNTTNPDGSYRSQVMRWDWASTNVIFNNRPLFAGQYTPWDSGNFD 540
PTP92  TFAQGVDANNNAVIAVNTTNPDGSYRSQVMRWDWASTNVIFNNRPLFAGQYTPWDSGNFD 540
NH-4   TFAQGVDANNNAVIAVNTTNPDGSYRSQVMRWDWASTNVIFNNRPLFAGQYTPWDSGNFD 540
14-1   TFAQGVDANNNAVIAVNTTNPDGSYRSQVMRWDWASTNVIFNDRPLFAGQYTPWDSGNFD 540
PTP47  TFAQGVDANNNAVIAVNTTNPDGSYRSQVMRWDWASTNVIFNNRPLFAGQYTPWDSGNFD 540
SN     TFAQGVDANNNAVIAVNTTNPDGSYRSQVMRWDWASTNVIFNNRPLFAGQYTPWDSGNFD 540
         ****************;****************;***********;*********

SPM-1  PATKLTVGTNNNISGPTGIRNFTSNTGRMNTWGSSSTTASYGNAALQIFGRGGEPAAIY 600
F8     PATKLTVGTNNNISGPTGIRNTTSNTGRMNTWGSSSTTASYGNAALQIFGRGGEPAAIY 600
PB1    PATKLTVGTNNNISGPTGIRNTTSNTGRMNTWGSSSTTASYGNAALQIFGRGGEPAAIY 600
C36    PATKLTVGTNNNISGPTGIRNTTSNTGRMNTWGSSSTTASYGNAAVQIFGRGDEPAAIY 600
LBL3   PATKLTVGTTNNISRPTGIRNTTSNTGRMNTWGSSSTTASYGNAALQIFGRGGGEPAAIY 600
Ph133  PSTKLTVNATNQIAGPTGIRNTNGNTGNMNTWGSGSTTASYGNAALQIFGKGGGEPAALY 600
LMA2   PSTKLTVNATNQIAGPTGIRNTNGNTGNMNTWGSGSTTASYGNAALQIFGKGGGEPAALY 600
KPP12  PSTKLTVNATNQIAGPTGIRNTNGNTGNMNTWGSSSTTASYGNAALQIFGKGGGEPAALY 600
JG024  PSTKLTVSATNQISGPTGIRNTNGNTGNMNTWGSGSTTASYGNAAIQIFGKGGGEPAAIY 600
PTP92  PSTKLTVSATNQISGPTGIRNTNGNTGNMNTWGSGSTTASYGNAAIQIFGKGGGEPAAIY 600
NH-4   PSTKLTVSATNQIAGPTGIRNTNGNTGNMNTWGSGSTTASYGNAAIQIFGKGGGEPAAIY 600
14-1   PSTKLTVSATNQIAGPTGIRNTNGNTGNMNTWGSGSTTASYGNAAIQIFGKGGGEPAAIY 600
PTP47  PSTKLTVSATNQIAGPTGIRNTNGNTGNMNTWGSGSTTASYGNAAIKIFGKGGGEPAAIY 600
SN     PSTKLTVRATNQIAGPTGIQNTNGNTGNMNTWGSGSTTASYGNAAIQIFGKGGGEPAAIY 600
         *:****  :**:*; ****:*  ..:*******.**********;:** .*:******;*

SPM-1  FDNSQTGWYLGMDKDGQLKRAGWSLGNN................................ 660
F8     FDNSQTGWYLGMDKDGQLKRAGWSLGNN................................ 660
PB1    FDNSQTGWYLGMDKDGQLKRAGWSLGNN................................ 660
C36    FDNSQTGWYLGMDKDGQLKRAGWSLGNN................................ 660
LBL3   FDNSQTGWYLGMDKDGQLKRAGWSLGNN................................ 660
Ph133  FDNSQTGWYLGMDKDGQLKRAGWSLGNN................................ 660
LMA2   FDNSQTGWYLGMDKDGQLKRAGWSLGNN................................ 660
KPP12  FDNSQTGWYLGMDKDGQLKRAGWSLGNN................................ 660
JG024  FDNSQTGWYLGMDKDGQLKRAGWSLGNN................................ 660
PTP92  FDNSQTGWYLGMDKDGQLKRAGWSLGNN................................ 660
NH-4   FDNSQTGWYLGMDKDGQLKRAGWSLGNN................................ 660
14-1   FDNSQTGWYLGMDKDGRLKRAGWSLGNN................................ 660
PTP47  FDNSQTGWYLGMDKDGQLKRAGWSLGNN................................ 660
SN     FDNSQTGWYLGMDKDGQLKRAGWSLGNN................................ 660
         ****************:*********** ***  *;* *;,.*;** .  *** *

SPM-1  ............................................................ 718
F8     ............................................................ 718
PB1    ............................................................ 718
C36    ............................................................ 718
LBL3   ............................................................ 718
Ph133  ............................................................ 718
```

Figure 13D

The figure shows a multiple sequence alignment of protein sequences from phages SPM-1, F8, PB1, C36, LBL3, Phi33, LMA2, KPP12, JG024, PTP92, NH-4, 14-1, PTP47, and SN, with residue position numbers along the right margin (718/719 through 956/958).

Figure 13E

```
PTP92      AVLDTCAPAASIAPGTIMDG...YKG.ASPTGTWR.MG.VYNP...NGDSAS  956
NH-4       AVLDTCAPAASIAPGTIMDG...YKG.ASPTGTWR.MG.VYNP...NGDSAS  956
14-1       AVLDYAAPIATVRPSVVDGS...GSCAAMYNSGQRTAGTWRCMGCVYNPSANTPDSAS 956
PTP47      AVLDYAAPIATVRPSVVDGS...GSCAAMYNSGQRTAGTWRCMGCVYNPSANTPDSAS 956
SN         AVLDYAAPIATVRPSVVDGS...GSCAAMYNSGQRTAGTWRCMGCVYNPSANTPDSAS 956
               ** *  *** ::: **.::*.* *:***   : :.*.  *:********: ***.    ***:
```

| | | | |
|---|---|---|---|
| SPM-1 | LPQRVE | 964 | (SEQ ID NO: 45) |
| F8    | LPQRVE | 964 | (SEQ ID NO: 46) |
| FB1   | LPQRVE | 964 | (SEQ ID NO: 47) |
| C36   | LPQRVE | 964 | (SEQ ID NO: 48) |
| LBL3  | LPQRVE | 964 | (SEQ ID NO: 49) |
| Phi33 | LPQRVE | 964 | (SEQ ID NO: 50) |
| LMA2  | LPQRVE | 964 | (SEQ ID NO: 51) |
| KPP12 | LPQRVE | 963 | (SEQ ID NO: 52) |
| JG024 | LPQRVE | 962 | (SEQ ID NO: 53) |
| PTP92 | LPQRVE | 962 | (SEQ ID NO: 54) |
| NH-4  | LPQRVE | 962 | (SEQ ID NO: 55) |
| 14-1  | LPQRVE | 962 | (SEQ ID NO: 56) |
| PTP47 | LPQRVE | 962 | (SEQ ID NO: 57) |
| SN    | LPQRVE | 962 | (SEQ ID NO: 58) |

(A)

(B)

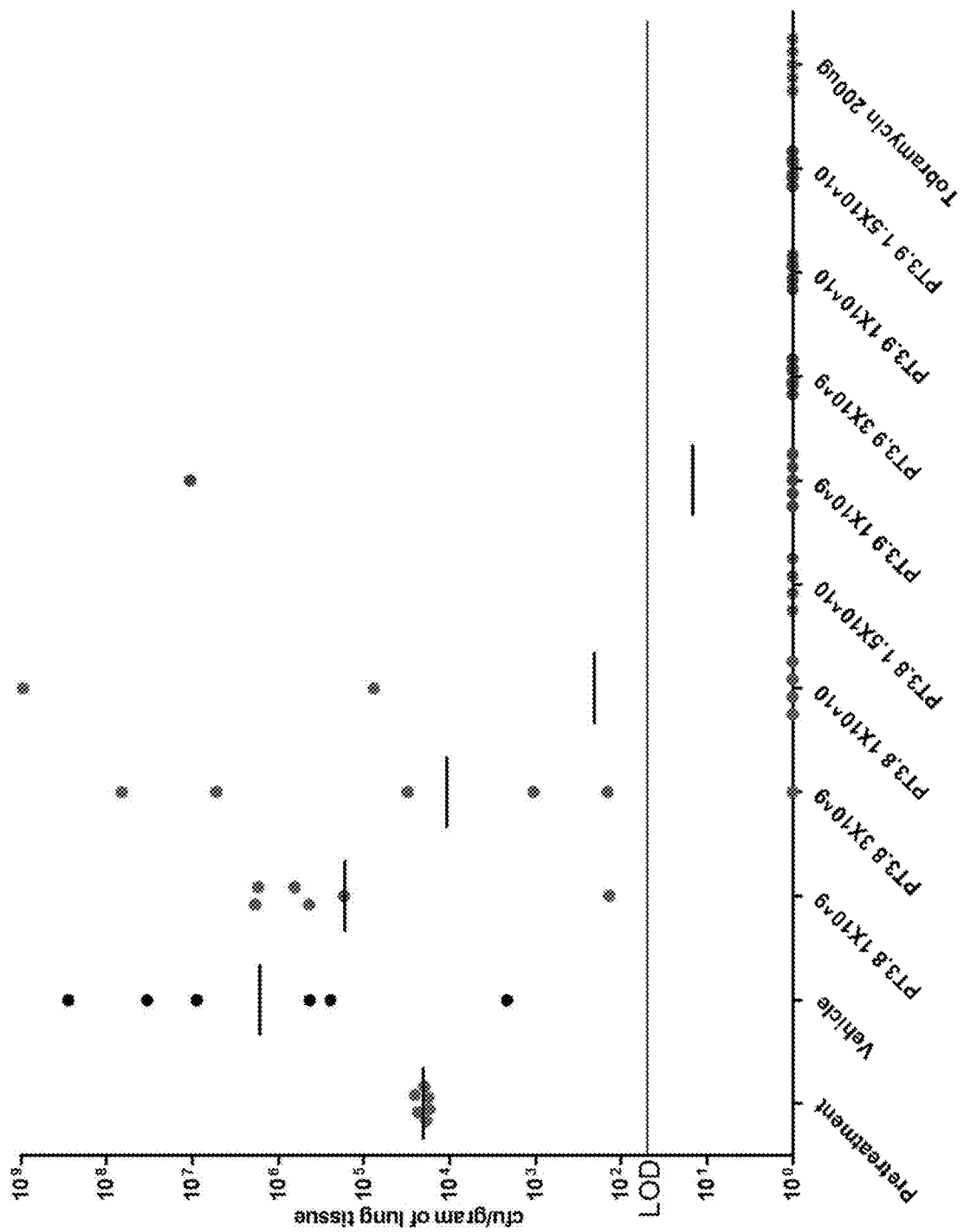

SEQUENCE LISTING

```
<160> NUMBER OF SEQ ID NOS: 59

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
gtgatcacac ccgaactg                                                 18

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
cgatgaagaa gagttggttt tg                                            22

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
acgccggact acgaaatcag                                               20

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
tccggagacg ttgatggt                                                 18

<210> SEQ ID NO 5
<211> LENGTH: 21
```

<212> TYPE: DNA
<213> ORGANISM: Artificial Sequence
<220> FEATURE:
<223> OTHER INFORMATION: primer

<400> SEQUENCE: 5
cctttcatcg atttccactt c                                         21

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ttcgtggacg cccagtccca                                           20

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
gataactagt cctggtccac cggggtcaag                                30

<210> SEQ ID NO 8
<211> LENGTH: 36
<212> TYPE: DNA
<213> ORGANISM: Artificial Sequence
<220> FEATURE:
<223> OTHER INFORMATION: primer

<400> SEQUENCE: 8
gctcagatct tccttaagtc agtcgcgcag gttcag                         36

<210> SEQ ID NO 9
<211> LENGTH: 37
<212> TYPE: DNA
<213> ORGANISM: Artificial Sequence
<220> FEATURE:
<223> OTHER INFORMATION: primer

<400> SEQUENCE: 9
aggaagatct gagctagctc ggaccagaac gaaaaag                        37

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
gatactcgag gcggatgaac attgaggtg                                 29

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
gataagatct gagcgcaacg caattaatgt g    31

<210> SEQ ID NO 12
<211> LENGTH: 64
<212> TYPE: DNA
<213> ORGANISM: Artificial Sequence
<220> FEATURE:
<223> OTHER INFORMATION: primer

<400> SEQUENCE: 12
gatagctagc agtcaaaagc ctccggtcgg aggcttttga ctttattttt gacaccagac    60
caac    64

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
gatagctagc atggttttca cgaccatg    28

<210> SEQ ID NO 14
<211> LENGTH: 50
<212> TYPE: DNA
<213> ORGANISM: Artificial Sequence
<220> FEATURE:
<223> OTHER INFORMATION: primer

<400> SEQUENCE: 14
gatagctagc gaggtaccga cctaggtttt ccagcgagtg acgtaaaatg    50

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
gatacctagg ttagcgccat tcgccattc    29

<210> SEQ ID NO 16
<211> LENGTH: 42
<212> TYPE: DNA
<213> ORGANISM: Artificial Sequence
<220> FEATURE:
<223> OTHER INFORMATION: primer

<400> SEQUENCE: 16
ctattccagc gggtaacgta aaatgaccat gattacggat tc    42

<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
gaatccgtaa tcatggtcat tttacgttac ccgctggaat ag    42

<210> SEQ ID NO 18
<211> LENGTH: 43

```
<212> TYPE: DNA
<213> ORGANISM: Artificial Sequence
<220> FEATURE:
<223> OTHER INFORMATION: primer

<400> SEQUENCE: 18
caagcgggcc ggctggtctc tcggcaataa ctcctatgtg atc         43

<210> SEQ ID NO 19
<211> LENGTH: 43
<212> TYPE: DNA
<213> ORGANISM: Artificial Sequence
<220> FEATURE:
<223> OTHER INFORMATION: primer

<400> SEQUENCE: 19
gatcacatag gagttattgc cgagagacca gccggcccgc ttg         43

<210> SEQ ID NO 20
<211> LENGTH: 28
<212> TYPE: DNA
<213> ORGANISM: Artificial Sequence
<220> FEATURE:
<223> OTHER INFORMATION: primer

<400> SEQUENCE: 20
gataggtacc gcgaccggtc tgtacttc                          28

<210> SEQ ID NO 21
<211> LENGTH: 42
<212> TYPE: DNA
<213> ORGANISM: Artificial Sequence
<220> FEATURE:
<223> OTHER INFORMATION: primer

<400> SEQUENCE: 21
cttttccagc gagtgacgta aaatgaccat gattacggat tc          42

<210> SEQ ID NO 22
<211> LENGTH: 42
<212> TYPE: DNA
<213> ORGANISM: Artificial Sequence
<220> FEATURE:
<223> OTHER INFORMATION: primer

<400> SEQUENCE: 22
gaatccgtaa tcatggtcat tttacgtcac tcgctggaaa ag          42

<210> SEQ ID NO 23
<211> LENGTH: 43
<212> TYPE: DNA
<213> ORGANISM: Artificial Sequence
<220> FEATURE:
<223> OTHER INFORMATION: primer

<400> SEQUENCE: 23
caagcgggcc ggctggtctc tcggcaataa ctcctatgtg atc         43

<210> SEQ ID NO 24
<211> LENGTH: 43
<212> TYPE: DNA
<213> ORGANISM: Artificial Sequence
<220> FEATURE:
<223> OTHER INFORMATION: primer

<400> SEQUENCE: 24
```
gatcacatag gagttattgc cgagagacca gccggcccgc ttg             43

<210> SEQ ID NO 25
<211> LENGTH: 42
<212> TYPE: DNA
<213> ORGANISM: Artificial Sequence
<220> FEATURE:
<223> OTHER INFORMATION: primer

<400> SEQUENCE: 25
ctattccagc gggtaacgta aaatgaaatg gacgcggatc ag             42

<210> SEQ ID NO 26
<211> LENGTH: 42
<212> TYPE: DNA
<213> ORGANISM: Artificial Sequence
<220> FEATURE:
<223> OTHER INFORMATION: primer

<400> SEQUENCE: 26
ctgatccgcg tccatttcat ttacgttac ccgctggaat ag              42

<210> SEQ ID NO 27
<211> LENGTH: 31
<212> TYPE: DNA
<213> ORGANISM: Artificial Sequence
<220> FEATURE:
<223> OTHER INFORMATION: primer

<400> SEQUENCE: 27
gatagctagc ggcaataact cctatgtgat c                         31

<210> SEQ ID NO 28
<211> LENGTH: 42
<212> TYPE: DNA
<213> ORGANISM: Artificial Sequence
<220> FEATURE:
<223> OTHER INFORMATION: primer

<400> SEQUENCE: 28
cttttccagc gagtgacgta aaatgaaatg gacgcggatc ag             42

<210> SEQ ID NO 29
<211> LENGTH: 42
<212> TYPE: DNA
<213> ORGANISM: Artificial Sequence
<220> FEATURE:
<223> OTHER INFORMATION: primer

<400> SEQUENCE: 29
ctgatccgcg tccatttcat tttacgtcac tcgctggaaa ag             42

<210> SEQ ID NO 30
<211> LENGTH: 31
<212> TYPE: DNA
<213> ORGANISM: Artificial Sequence
<220> FEATURE:
<223> OTHER INFORMATION: primer

<400> SEQUENCE: 30
gatagctagc ggcaataact cctatgtgat c                         31

<210> SEQ ID NO 31
<211> LENGTH: 28
<212> TYPE: DNA
<213> ORGANISM: Artificial Sequence

```
<220> FEATURE:
<223> OTHER INFORMATION: primer

<400> SEQUENCE: 31
gatagctagc tttctcgttt taatgtcg                                      28

<210> SEQ ID NO 32
<211> LENGTH: 37
<212> TYPE: DNA
<213> ORGANISM: Artificial Sequence
<220> FEATURE:
<223> OTHER INFORMATION: primer

<400> SEQUENCE: 32
gatacctagg tgctcgagta ttcgcccaaa agaaaag                            37

<210> SEQ ID NO 33
<211> LENGTH: 29
<212> TYPE: DNA
<213> ORGANISM: Artificial Sequence
<220> FEATURE:
<223> OTHER INFORMATION: primer

<400> SEQUENCE: 33
gatacctagg tcaggagcct tgattgatc                                     29

<210> SEQ ID NO 34
<211> LENGTH: 29
<212> TYPE: DNA
<213> ORGANISM: Artificial Sequence
<220> FEATURE:
<223> OTHER INFORMATION: primer

<400> SEQUENCE: 34
gatacctagg tcaggagcct tgattgatc                                     29

<210> SEQ ID NO 35
<211> LENGTH: 65
<212> TYPE: DNA
<213> ORGANISM: Artificial Sequence
<220> FEATURE:
<223> OTHER INFORMATION: primer

<400> SEQUENCE: 35
gatactcgag gatctagtca aaagcctccg accggaggct tttgacttta gtacttgccg   60
cctag                                                               65

<210> SEQ ID NO 36
<211> LENGTH: 29
<212> TYPE: DNA
<213> ORGANISM: Artificial Sequence
<220> FEATURE:
<223> OTHER INFORMATION: primer

<400> SEQUENCE: 36
gataccatgg caaattatca aaacgcatc                                     29

<210> SEQ ID NO 37
<211> LENGTH: 28
<212> TYPE: DNA
<213> ORGANISM: Artificial Sequence
<220> FEATURE:
<223> OTHER INFORMATION: primer

<400> SEQUENCE: 37
```

```
gataccatgg tagttcctcg ataagtcg                                      28
```

<210> SEQ ID NO 38
<211> LENGTH: 39
<212> TYPE: DNA
<213> ORGANISM: Artificial Sequence
<220> FEATURE:
<223> OTHER INFORMATION: primer

<400> SEQUENCE: 38

```
gatacctagg cctagggatc tgaccgaccg atctactcc                          39
```

<210> SEQ ID NO 39
<211> LENGTH: 29
<212> TYPE: DNA
<213> ORGANISM: Artificial Sequence
<220> FEATURE:
<223> OTHER INFORMATION: primer

<400> SEQUENCE: 39

```
gatactcgag ttagcgccat tcgccattc                                     29
```

<210> SEQ ID NO 40
<211> LENGTH: 29
<212> TYPE: DNA
<213> ORGANISM: Artificial Sequence
<220> FEATURE:
<223> OTHER INFORMATION: primer

<400> SEQUENCE: 40

```
gatactcgag gcgcaacgca attaatgtg                                     29
```

<210> SEQ ID NO 41
<211> LENGTH: 60
<212> TYPE: DNA
<213> ORGANISM: Artificial Sequence
<220> FEATURE:
<223> OTHER INFORMATION: primer

<400> SEQUENCE: 41

```
gatactcgag agtcaaaagc ctccgaccgg aggcttttga cttcagtact tgccgcccag   60
```

<210> SEQ ID NO 42
<211> LENGTH: 40
<212> TYPE: DNA
<213> ORGANISM: Artificial Sequence
<220> FEATURE:
<223> OTHER INFORMATION: primer

<400> SEQUENCE: 42

```
gattgggaga tacgagaacc atggccaact accagaacgc                         40
```

<210> SEQ ID NO 43
<211> LENGTH: 40
<212> TYPE: DNA
<213> ORGANISM: Artificial Sequence
<220> FEATURE:
<223> OTHER INFORMATION: primer

<400> SEQUENCE: 43

```
gcgttctggt agttggccat ggttctcgta tctcccaatc                         40
```

<210> SEQ ID NO 44
<211> LENGTH: 28
<212> TYPE: DNA
<213> ORGANISM: Artificial Sequence

```
<220> FEATURE:
<223> OTHER INFORMATION: primer

<400> SEQUENCE: 44
gatacctagg aacgacgaag gcctggtg                                            28

<210> SEQ ID NO 45
<211> LENGTH: 964
<212> TYPE: PRT
<213> ORGANISM: bacteriophage SPM-1

<400> SEQUENCE: 45
```

| Met | Ile | Thr | Pro | Glu | Leu | Ile | Pro | Ser | Pro | Phe | Ala | Ala | Gln | Gly | Asp |
|---|---|---|---|---|---|---|---|---|---|---|---|---|---|---|---|
| 1 | | | | 5 | | | | | 10 | | | | | 15 | |

| Lys | Asp | Pro | Ile | Pro | Gln | Thr | Ser | Ser | Thr | Gly | Phe | Ala | Asn | Leu | Arg |
|---|---|---|---|---|---|---|---|---|---|---|---|---|---|---|---|
| | | | 20 | | | | | 25 | | | | | 30 | | |

| Asp | Gly | Tyr | Thr | Pro | Asp | Tyr | Glu | Ile | Ser | Leu | Ala | Ser | Asn | Asn | Pro |
|---|---|---|---|---|---|---|---|---|---|---|---|---|---|---|---|
| | | | 35 | | | | | 40 | | | | | 45 | | |

| Gln | Ala | Lys | Ala | Val | Glu | Arg | Lys | Ile | Gln | Asn | Gln | Leu | Phe | Phe | Ile |
|---|---|---|---|---|---|---|---|---|---|---|---|---|---|---|---|
| | 50 | | | | | 55 | | | | | 60 | | | | |

| Ala | Thr | Gln | Asn | Ala | Gln | Ala | Trp | Gln | Arg | Gln | Met | Ala | Pro | Pro | Trp |
|---|---|---|---|---|---|---|---|---|---|---|---|---|---|---|---|
| 65 | | | | | 70 | | | | | 75 | | | | | 80 |

| Phe | Gln | Gly | Met | Pro | Gly | Gly | Tyr | Glu | Gln | Asn | Ala | Glu | Val | Val | Arg |
|---|---|---|---|---|---|---|---|---|---|---|---|---|---|---|---|
| | | | | 85 | | | | | 90 | | | | | 95 | |

| Val | Gly | Asn | Asp | Gly | Ile | Met | Arg | Arg | Tyr | Arg | Ser | Met | Val | Asn | Ala |
|---|---|---|---|---|---|---|---|---|---|---|---|---|---|---|---|
| | | | 100 | | | | | 105 | | | | | 110 | | |

| Asn | Ala | Ser | Asp | Pro | Leu | Ser | Ser | Thr | Thr | Trp | Glu | Glu | Gln | Pro | Ala |
|---|---|---|---|---|---|---|---|---|---|---|---|---|---|---|---|
| | | 115 | | | | | 120 | | | | | 125 | | | |

| Trp | Ser | Val | Met | Arg | Ser | Asn | Ile | Pro | Met | Pro | Ala | Gly | Gly | Ser | Gly |
|---|---|---|---|---|---|---|---|---|---|---|---|---|---|---|---|
| | 130 | | | | | 135 | | | | | 140 | | | | |

| Leu | Ser | Ser | Gly | Gly | Glu | Val | Ile | Thr | Thr | Gly | Arg | Asn | Phe | Asn | Asp |
|---|---|---|---|---|---|---|---|---|---|---|---|---|---|---|---|
| 145 | | | | | 150 | | | | | 155 | | | | | 160 |

| Leu | Leu | Asn | Gly | Thr | Trp | Glu | Phe | Phe | Ser | Asp | Ser | Val | Val | Val | Ala |
|---|---|---|---|---|---|---|---|---|---|---|---|---|---|---|---|
| | | | | 165 | | | | | 170 | | | | | 175 | |

| Ser | Gln | Asn | Ala | Pro | Val | Tyr | Pro | Ala | Ser | Ala | Gly | Ala | Ala | Ala | Gly |
|---|---|---|---|---|---|---|---|---|---|---|---|---|---|---|---|
| | | | 180 | | | | | 185 | | | | | 190 | | |

| Met | Leu | Glu | Ala | Lys | Ser | Trp | Val | Ser | Gly | Ala | Asn | Thr | Phe | Cys | Val |
|---|---|---|---|---|---|---|---|---|---|---|---|---|---|---|---|
| | | 195 | | | | | 200 | | | | | 205 | | | |

| Gln | Arg | Tyr | Thr | Asp | Arg | Val | Gly | Asn | Val | Ala | Val | Arg | Gly | Leu | Asn |
|---|---|---|---|---|---|---|---|---|---|---|---|---|---|---|---|
| | 210 | | | | | 215 | | | | | 220 | | | | |

| Ala | Gly | Ala | Trp | Thr | Asn | Trp | Met | Tyr | Ala | Val | Asn | Val | Met | Ala | Leu |
|---|---|---|---|---|---|---|---|---|---|---|---|---|---|---|---|
| 225 | | | | | 230 | | | | | 235 | | | | | 240 |

| Gln | Gln | Gly | Arg | Val | Thr | Tyr | Gly | Val | Ala | Ala | Gly | Ser | Ala | Asn | Ala |
|---|---|---|---|---|---|---|---|---|---|---|---|---|---|---|---|
| | | | | 245 | | | | | 250 | | | | | 255 | |

| Tyr | Thr | Leu | Thr | Leu | Val | Pro | Gln | Leu | Gln | Gly | Gly | Leu | Val | Asp | Gly |
|---|---|---|---|---|---|---|---|---|---|---|---|---|---|---|---|
| | | | 260 | | | | | 265 | | | | | 270 | | |

| Met | Val | Leu | Arg | Val | Lys | Phe | Asn | Ala | Met | Asn | Thr | Gly | Ala | Ser | Thr |
|---|---|---|---|---|---|---|---|---|---|---|---|---|---|---|---|
| | | 275 | | | | | 280 | | | | | 285 | | | |

| Ile | Asn | Val | Ser | Gly | Phe | Gly | Ser | Lys | Ala | Ile | Val | Gly | Ala | Ala | Asn |
|---|---|---|---|---|---|---|---|---|---|---|---|---|---|---|---|
| | 290 | | | | | 295 | | | | | 300 | | | | |

| Phe | Pro | Leu | Thr | Gly | Gly | Glu | Leu | Gly | Gln | Gly | Leu | Ile | Ala | Glu | Leu |
|---|---|---|---|---|---|---|---|---|---|---|---|---|---|---|---|
| 305 | | | | | 310 | | | | | 315 | | | | | 320 |

| Val | Phe | Asp | Ala | Thr | Gly | Asp | Arg | Trp | Arg | Ile | Leu | Ala | Gly | Ala | Pro |
|---|---|---|---|---|---|---|---|---|---|---|---|---|---|---|---|
| | | | | 325 | | | | | 330 | | | | | 335 | |

| Arg | Ile | Gln | Val | Gly | Asn | Ala | Asp | Gln | Asp | Tyr | Gln | Ala | Pro | Ser | Trp |

```
            340                 345                 350
Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
370                 375                 380

Pro Trp Phe Ala Asn Leu Glu Leu Ser Asp Ala Arg Pro Phe Ile Asp
385                 390                 395                 400

Phe His Phe Asn Asn Arg Ala Lys Asp Phe Asp Tyr Arg Phe Ile
                    405                 410                 415

Ser Glu Ala Asp Gly Ser Met Ala Phe Tyr Ser Arg Gln Gly Ser Ala
                420                 425                 430

Gly Pro Thr Gln Asp Ile Leu Phe Ser Arg Ser Asn Val Thr Phe Leu
            435                 440                 445

Gln Pro Arg Leu Asp Val Ala Lys Asn Leu Ala Tyr Ile Ala Asn Ser
        450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                    485                 490                 495

Asn Thr Thr Asn Pro Asp Gly Ser Tyr Arg Ser Gln Ile Met Arg Trp
                500                 505                 510

Asp Trp Ala Ser Thr Asn Val Ile Phe Asn Asn Arg Pro Leu Phe Ala
            515                 520                 525

Gly Gln Tyr Val Pro Trp Asp Ser Gly Asn Phe Asp Pro Ala Thr Lys
        530                 535                 540

Leu Thr Val Gly Thr Thr Asn Asn Ile Ser Gly Pro Thr Gly Ile Arg
545                 550                 555                 560

Asn Thr Thr Ser Asn Thr Gly Asn Met Asn Thr Trp Gly Ser Ser Ser
                    565                 570                 575

Thr Thr Ala Ser Tyr Gly Asn Ala Ala Leu Gln Ile Phe Gly Arg Gly
                580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
        610                 615                 620

Leu Gly Asn Asn Ser Tyr Val Val Thr Asp Glu Ser Asn Ile Arg Asn
625                 630                 635                 640

His Val Asn Gly Met Ser Gly Ala Pro Val Trp Gly Gly Gln Trp Phe
                    645                 650                 655

Trp Gly Glu Trp Asn Phe Asn Pro Asn Thr Lys Leu Thr Ile Lys Ala
                660                 665                 670

Gly Thr Gln Glu Thr Ser Ser Thr Ala Ile Phe Ser Gly Thr Leu Pro
            675                 680                 685

Phe Ala Pro Ile Ala Ser Leu Ser Asp Tyr Ser Gln Ala Pro Leu Thr
        690                 695                 700

Ile Tyr Asn Ser Pro Thr Gly Pro Ser Ala Lys Pro Ala Val Ile Ala
705                 710                 715                 720

Phe Ile Arg Pro Gly Asn Trp Gly Ala Phe Gly Ile Asp Thr Asp
                    725                 730                 735

Asn Lys Leu Lys Trp Gly Gly Gly Ser Leu Gly Asn Asn Ser Arg Glu
                740                 745                 750

Ile Ala Asp Ser Ser Asn Ile Met Asn Leu Trp Ala Ser Asn Pro Thr
            755                 760                 765
```

```
Ala Pro Ser Trp Asn Gly Gln Thr Val Trp Arg Ser Gly Asn Phe Asp
        770                 775                 780

Pro Ala Thr Lys Val Asp Leu Asn Ala Ala Asn Ala Thr Asn Gly Ser
785                 790                 795                 800

Met Ile Phe Asn Arg Ile Ser Gly Thr Gly Ser Gly Ile Ala Ser Ser
                805                 810                 815

Gly Arg Val Gly Ala Ile Asn Leu Gln Asn Gly Ala His Ser Gly Gln
            820                 825                 830

Ala Ala Ala Val Thr Phe Glu Arg Gly Gly Ser Ile Phe Val Asn Phe
        835                 840                 845

Gly Leu Asp Thr Asp Asn Val Leu Lys Val Gly Gly Asn Leu Gly
    850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Val Gly Ser Tyr Gly
                885                 890                 895

Ile Phe Ala Val Leu Asp Asn Ala Ala Pro Ile Ala Thr Val Gln Pro
                900                 905                 910

Gly Val Val Val Asp Gly Ser Ile Leu Ile Tyr Ser Ser Cys Ala Ala
                915                 920                 925

Asn Tyr Asn Ser Gly Gln Lys Pro Ala Gly Thr Trp Arg Cys Met Gly
            930                 935                 940

Tyr Val Val Asn Arg Asp Ala Asn Thr Ala Asp Ser Ala Thr Leu Phe
945                 950                 955                 960

Gln Arg Val Thr

<210> SEQ ID NO 46
<211> LENGTH: 964
<212> TYPE: PRT
<213> ORGANISM: bacteriophage F8

<400> SEQUENCE: 46

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
                100                 105                 110

Asn Ala Ser Asp Pro Leu Ser Ser Thr Thr Trp Glu Glu Gln Pro Ala
            115                 120                 125

Trp Ser Val Met Arg Ser Asn Ile Pro Met Pro Ala Gly Gly Ser Gly
        130                 135                 140

Leu Ser Ser Gly Gly Glu Val Ile Thr Gly Arg Asn Phe Asn Asp
145                 150                 155                 160

Leu Leu Asn Gly Thr Trp Glu Phe Phe Ser Asp Ser Val Val Ala Ala
                165                 170                 175
```

```
Ser Gln Asn Ala Pro Val Tyr Pro Ser Ala Gly Ala Ala Gly
            180                 185                 190

Met Leu Glu Ala Lys Ser Trp Val Ser Gly Ala Asn Thr Phe Cys Val
            195                 200                 205

Gln Arg Tyr Thr Asp Arg Val Gly Asn Val Ala Val Arg Gly Leu Asn
210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
            245                 250                 255

Tyr Thr Leu Thr Leu Val Pro Gln Leu Gln Gly Gly Leu Val Asp Gly
            260                 265                 270

Met Val Leu Arg Val Lys Phe Asn Ala Met Asn Thr Gly Ala Ser Thr
            275                 280                 285

Ile Asn Val Ser Gly Phe Gly Ser Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
            420                 425                 430

Gly Pro Thr Gln Asp Ile Leu Phe Ser Arg Ser Asn Val Thr Phe Leu
            435                 440                 445

Gln Pro Arg Leu Asp Val Ala Lys Asn Leu Ala Tyr Ile Ala Asn Ser
450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
            485                 490                 495

Asn Thr Thr Asn Pro Asp Gly Ser Tyr Arg Ser Gln Ile Met Arg Trp
            500                 505                 510

Asp Trp Ala Ser Thr Asn Val Ile Phe Asn Asn Arg Pro Leu Phe Ala
            515                 520                 525

Gly Gln Tyr Val Pro Trp Asp Ser Gly Asn Phe Asp Pro Ala Thr Lys
            530                 535                 540

Leu Thr Val Gly Thr Thr Asn Asn Ile Ser Gly Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Leu Gln Ile Phe Gly Arg Gly
            580                 585                 590
```

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
610                 615                 620

Leu Gly Asn Asn Ser Tyr Val Val Thr Asp Glu Ser Asn Ile Arg Asn
625                 630                 635                 640

His Val Asn Gly Met Ser Gly Ala Pro Val Trp Gly Gln Trp Phe
            645                 650                 655

Trp Gly Glu Trp Asn Phe Asn Pro Thr Lys Leu Thr Ile Lys Ala
            660                 665                 670

Gly Thr Gln Glu Thr Ser Ser Thr Ala Ile Phe Ser Gly Thr Leu Pro
            675                 680                 685

Phe Ala Pro Ile Ala Ser Leu Ser Asp Tyr Ser Gln Ala Pro Leu Thr
690                 695                 700

Ile Tyr Asn Ser Pro Thr Gly Pro Ser Ala Lys Pro Ala Val Ile Ala
705                 710                 715                 720

Phe Ile Arg Pro Gly Asn Trp Gly Ala Phe Gly Ile Asp Thr Asp
            725                 730                 735

Asn Lys Leu Lys Trp Gly Gly Gly Ser Leu Gly Asn Asn Ser Arg Glu
            740                 745                 750

Ile Ala Asp Ser Ser Asn Ile Met Asn Leu Trp Ala Ser Asn Pro Thr
            755                 760                 765

Ala Pro Ser Trp Asn Gly Gln Thr Val Trp Arg Ser Gly Asn Phe Asp
            770                 775                 780

Pro Ala Thr Lys Val Asp Leu Asn Ala Ala Asn Ala Thr Asn Gly Ser
785                 790                 795                 800

Met Ile Phe Asn Arg Ile Ser Gly Thr Gly Ser Gly Ile Ala Ser Ser
            805                 810                 815

Gly Arg Val Gly Ala Ile Asn Leu Gln Asn Gly Ala His Ser Gly Gln
            820                 825                 830

Ala Ala Ala Val Thr Phe Glu Arg Gly Gly Ser Ile Phe Val Asn Phe
            835                 840                 845

Gly Leu Asp Thr Asp Asn Val Leu Lys Val Gly Gly Gly Asn Leu Gly
850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Val Gly Ser Tyr Gly
            885                 890                 895

Ile Phe Ala Val Leu Asp Asn Ala Ala Pro Ile Ala Thr Val Gln Pro
            900                 905                 910

Gly Val Val Val Asp Gly Ser Ile Leu Ile Tyr Ser Ser Cys Ala Ala
            915                 920                 925

Asn Tyr Asn Ser Gly Gln Lys Pro Ala Gly Thr Trp Arg Cys Met Gly
            930                 935                 940

Tyr Val Val Asn Arg Asp Ala Asn Thr Ala Asp Ser Ala Thr Leu Phe
945                 950                 955                 960

Gln Arg Val Thr

<210> SEQ ID NO 47
<211> LENGTH: 964
<212> TYPE: PRT
<213> ORGANISM: bacteriophage PB1

<400> SEQUENCE: 47

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
                35                  40                  45

Gln Ala Lys Ala Val Glu Arg Lys Ile Gln Asn Gln Leu Phe Phe Ile
50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
            115                 120                 125

Trp Ser Val Met Arg Ser Asn Ile Pro Met Pro Ala Gly Gly Pro Gly
        130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala
                165                 170                 175

Ser Gln Asn Ala Pro Val Tyr Pro Ala Ser Ala Gly Ala Ala Ala Gly
                180                 185                 190

Met Leu Glu Ala Lys Ser Trp Ile Ser Gly Ser Asn Thr Phe Cys Val
            195                 200                 205

Gln Arg Tyr Thr Asp Arg Val Gly Asn Val Ala Val Arg Gly Leu Asn
        210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Val Asn Thr Gly Ala Ser Thr
        275                 280                 285

Ile Asn Val Ser Gly Phe Gly Ala Lys Ala Ile Val Gly Ala Ala Asn
        290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
370                 375                 380

Pro Trp Phe Ala Asn Leu Glu Leu Ser Asp Ala Arg Pro Phe Ile Asp
385                 390                 395                 400

Phe His Phe Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
```

-continued

```
                420             425             430
Gly Pro Thr Gln Asp Ile Leu Phe Ser Arg Ser Asn Val Thr Phe Leu
            435                 440                 445
Gln Pro Arg Leu Asp Val Ala Lys Asn Leu Ala Tyr Ile Ala Asn Ser
450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
                485                 490                 495
Asn Thr Thr Asn Pro Asp Gly Ser Tyr Arg Ser Gln Val Met Arg Trp
            500                 505                 510
Asp Trp Ala Ser Thr Asn Val Ile Phe Asn Asn Arg Pro Leu Phe Ala
            515                 520                 525
Gly Gln Tyr Val Pro Trp Asp Ser Gly Asn Phe Asp Pro Ala Thr Lys
            530                 535                 540
Leu Thr Val Gly Thr Thr Asn Asn Ile Ser Gly Pro Thr Gly Ile Arg
545                 550                 555                 560
Asn Thr Thr Ser Asn Thr Gly Asn Met Asn Thr Trp Gly Ser Ser Ser
                565                 570                 575
Thr Thr Ala Ser Tyr Gly Asn Ala Ala Leu Gln Ile Phe Gly Arg Gly
                580                 585                 590
Gly Gly Glu Pro Ala Ala Ile Tyr Phe Asp Asn Ser Gln Thr Gly Trp
        595                 600                 605
Tyr Leu Gly Met Asp Lys Asp Gly Gln Leu Lys Arg Ala Gly Trp Ser
        610                 615                 620
Leu Gly Asn Asn Ser Tyr Val Val Thr Asp Glu Ser Asn Ile Arg Asn
625                 630                 635                 640
His Val Asn Gly Met Ser Gly Ala Pro Val Trp Gly Gln Trp Phe
                645                 650                 655
Trp Gly Glu Trp Asn Phe Asn Pro Asn Thr Lys Leu Thr Ile Lys Ala
                660                 665                 670
Gly Thr Gln Glu Thr Ser Ser Thr Ala Ile Phe Ser Gly Thr Leu Pro
            675                 680                 685
Phe Ala Pro Ile Ala Ser Leu Ser Asp Tyr Ser Gln Ala Pro Leu Thr
690                 695                 700
Ile Tyr Asn Ser Pro Thr Gly Pro Ser Ala Lys Pro Ala Val Ile Ala
705                 710                 715                 720
Phe Ile Arg Pro Gly Asn Trp Gly Ala Phe Phe Gly Ile Asp Thr Asp
                725                 730                 735
Asn Lys Leu Lys Trp Gly Gly Ser Leu Gly Asn Asn Ser Arg Glu
            740                 745                 750
Ile Ala Asp Ser Ser Asn Ile Met Asn Leu Trp Ala Ser Asn Pro Thr
            755                 760                 765
Ala Pro Ser Trp Asn Gly Gln Thr Val Trp Arg Ser Gly Asn Phe Asp
770                 775                 780
Pro Ala Thr Lys Val Asp Leu Asn Ala Ala Asn Ala Thr Asn Gly Asn
785                 790                 795                 800
Met Ile Phe Asn Arg Ile Ser Gly Thr Gly Ser Gly Ile Ala Ser Ser
                805                 810                 815
Gly Arg Val Gly Ala Ile Asn Leu Gln Asn Gly Ala His Ser Gly Gln
            820                 825                 830
Ala Ala Ala Val Thr Phe Glu Arg Gly Gly Ser Ile Phe Val Asn Phe
            835                 840                 845
```

-continued

```
Gly Leu Asp Thr Asp Asn Val Leu Lys Val Gly Gly Asn Leu Gly
    850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Gly Val Gly Ser Tyr Gly
                885                 890                 895

Ile Phe Ala Val Leu Asp Asn Ala Ala Pro Ile Ala Thr Val Gln Pro
            900                 905                 910

Gly Val Val Asp Gly Ser Ile Leu Ile Tyr Ser Ser Cys Ala Ala
                915                 920                 925

Asn Tyr Asn Ser Gly Gln Lys Pro Ala Gly Thr Trp Arg Cys Met Gly
    930                 935                 940

Tyr Val Val Asn Arg Asp Ala Asn Thr Pro Asp Ser Ala Thr Leu Phe
945                 950                 955                 960

Gln Arg Val Thr

<210> SEQ ID NO 48
<211> LENGTH: 964
<212> TYPE: PRT
<213> ORGANISM: bacteriophage C36

<400> SEQUENCE: 48

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Ser Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala
                165                 170                 175

Ser Gln Asn Ala Pro Val Tyr Pro Ala Ser Gly Ala Ala Ala Gly
            180                 185                 190

Met Leu Glu Ala Lys Ser Trp Ile Ser Gly Ser Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Pro Ala Asn Ala
                245                 250                 255
```

Tyr Thr Leu Thr Leu Val Pro Gln Leu Gln Gly Gly Leu Val Asp Gly
            260                 265                 270

Met Ile Leu Arg Val Lys Phe Asn Thr Val Asn Thr Gly Ala Ser Thr
        275                 280                 285

Ile Asn Val Ser Gly Phe Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
            420                 425                 430

Gly Pro Thr Gln Asp Ile Leu Phe Ser Arg Ser Asn Val Thr Phe Leu
        435                 440                 445

Gln Pro Arg Leu Asp Val Ala Lys Asn Leu Ala Tyr Ile Ala Asn Ser
    450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Ile Met Arg Trp
            500                 505                 510

Asp Trp Ala Ser Thr Asn Val Ile Phe Asn Asn Arg Pro Leu Phe Ala
        515                 520                 525

Gly Gln Tyr Val Pro Trp Asp Ser Gly Asn Phe Asp Pro Ala Thr Lys
    530                 535                 540

Leu Thr Val Gly Thr Thr Asn Asn Ile Ser Gly Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Val Gln Ile Phe Gly Arg Gly
            580                 585                 590

Asp Gly Glu Pro Ala Ala Ile Tyr Phe Asp Asn Ser Gln Thr Gly Trp
        595                 600                 605

Tyr Leu Gly Met Asp Lys Asp Gly Gln Leu Lys Arg Ala Gly Trp Ser
    610                 615                 620

Leu Gly Asn Asn Ser Tyr Val Val Thr Asp Glu Ser Asn Ile Arg Phe
625                 630                 635                 640

His Val Asn Ser Met Ala Gly Thr Pro Val Trp Gly Asn Glu Phe
                645                 650                 655

Trp Gly Pro Trp Asn Phe Asn Pro Asn Thr Lys Leu Thr Ile Lys Ala
        660                 665                 670

```
Gly Thr Gln Glu Thr Ser Ser Thr Ala Ile Phe Ser Gly Thr Met Pro
            675                 680                 685

Phe Ala Pro Ile Ala Ser Leu Ser Asp Tyr Ser Gln Ala Pro Leu Thr
        690                 695                 700

Ile Tyr Asn Ser Pro Thr Gly Pro Ser Ala Lys Pro Ala Val Ile Ala
705                 710                 715                 720

Phe Ile Arg Pro Gly Asn Trp Gly Ala Phe Gly Ile Asp Thr Asp
                725                 730                 735

Asn Lys Leu Lys Trp Gly Gly Ser Leu Gly Asn Ser Ser Arg Glu
                740                 745                 750

Ile Ala Asp Ser Ser Asn Ile Met Asn Leu Trp Ala Ala Asn Pro Thr
            755                 760                 765

Ala Pro Ser Trp Asn Gly Gln Thr Val Trp Arg Ser Gly Asn Phe Asp
        770                 775                 780

Pro Ala Thr Lys Val Asp Leu Asn Ala Ala Asn Ala Thr Asn Gly Asn
785                 790                 795                 800

Met Val Phe Asn Arg Ile Ser Gly Thr Gly Ser Gly Ile Ala Ser Ser
                805                 810                 815

Gly Arg Val Gly Ala Ile Asn Leu Gln Asn Gly Ala His Ser Gly Gln
            820                 825                 830

Ala Ala Ala Val Thr Phe Glu Arg Gly Gly Ser Ile Phe Val Asn Phe
        835                 840                 845

Gly Leu Asp Thr Asp Asn Val Leu Lys Val Gly Gly Asn Leu Gly
                850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Gly Val Gly Ser Tyr Gly
                885                 890                 895

Ile Phe Ala Val Leu Asp Asn Ala Ala Pro Ile Ala Thr Val Gln Pro
            900                 905                 910

Gly Val Val Val Asp Gly Ser Ile Leu Ile Tyr Ser Ser Cys Ser Ala
        915                 920                 925

Asn Tyr Asn Ser Gly Gln Arg Pro Ala Gly Thr Trp Arg Cys Met Gly
930                 935                 940

Tyr Val Val Asn Arg Asp Ala Asn Thr Pro Asp Ser Ala Thr Leu Phe
945                 950                 955                 960

Gln Arg Val Thr

<210> SEQ ID NO 49
<211> LENGTH: 964
<212> TYPE: PRT
<213> ORGANISM: bacteriohage LBL3

<400> SEQUENCE: 49

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
        50                  55                  60

Ala Thr Gln Asn Ala Gln Ala Trp Gln Arg Gln Met Ala Pro Pro Trp
65                  70                  75                  80
```

```
Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
        275                 280                 285

Ile Asn Val Ser Gly Phe Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
            420                 425                 430

Gly Pro Thr Gln Asp Ile Leu Phe Ser Arg Ser Asn Val Thr Phe Leu
        435                 440                 445

Gln Pro Arg Leu Asp Val Ala Lys Asn Leu Ala Tyr Ile Ala Asn Ser
    450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Ile Met Arg Trp
```

-continued

```
                500               505               510
Asp Trp Ala Ser Thr Asn Val Ile Phe Asn Asn Arg Pro Leu Phe Ala
            515                 520                 525

Gly Gln Tyr Val Pro Trp Asp Ser Gly Asn Phe Asp Pro Ala Thr Lys
        530                 535                 540

Leu Thr Val Gly Thr Thr Asn Asn Ile Ser Arg Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Leu Gln Ile Phe Gly Arg Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Gln Leu Lys Arg Ala Gly Trp Ser
    610                 615                 620

Leu Gly Asn Asn Ser Tyr Val Val Thr Asp Glu Ser Asn Ile Arg Phe
625                 630                 635                 640

His Val Asn Ser Met Ala Gly Thr Pro Val Trp Gly Gly Asn Glu Phe
                645                 650                 655

Trp Gly Pro Trp Asn Phe Asn Pro Asn Thr Lys Leu Thr Ile Lys Ala
            660                 665                 670

Gly Thr Gln Glu Thr Ser Ser Thr Ala Ile Phe Ser Gly Thr Met Pro
        675                 680                 685

Phe Ala Pro Ile Ala Ser Leu Ser Asp Tyr Ser Gln Ala Pro Leu Thr
    690                 695                 700

Val Tyr Asn Ser Pro Thr Gly Pro Ser Ala Lys Pro Ala Val Ile Ala
705                 710                 715                 720

Phe Ile Arg Pro Gly Asn Trp Gly Ala Phe Phe Gly Ile Asp Thr Asp
                725                 730                 735

Asn Lys Leu Lys Trp Gly Gly Gly Ser Leu Gly Asn Ser Ser Arg Glu
            740                 745                 750

Ile Ala Asp Ser Ser Asn Ile Met Asn Leu Trp Ala Ala Asn Pro Thr
        755                 760                 765

Ala Pro Thr Trp Asn Gly Gln Thr Ile Trp Arg Ser Gly Asn Phe Asp
    770                 775                 780

Pro Ala Thr Lys Val Asp Leu Asn Ala Ala Asn Ala Thr Asn Gly Asn
785                 790                 795                 800

Met Ile Phe Asn Arg Ile Ala Gly Thr Gly Ser Gly Ile Ala Ser Ser
                805                 810                 815

Asp Arg Val Gly Ala Ile Ser Leu Gln Asn Gly Ala Thr Ala Gly Ala
            820                 825                 830

Ala Ala Ala Val Thr Phe Glu Arg Gly Gly Phe Val Asn Phe
        835                 840                 845

Gly Leu Asp Thr Asp Asn Val Leu Lys Val Gly Gly Asn Leu Gly
    850                 855                 860

Ala Asn Ala Tyr Pro Val Ile His Ala Gly Asn Tyr Asn Tyr Ile
865                 870                 875                 880

Asn Gln Ala Leu Val Gln Val Gly Leu Gly Gly Val Gly Ser Tyr Gly
                885                 890                 895

Ile Phe Ala Val Leu Asp Tyr Ala Ala Pro Thr Ala Thr Val Gln Pro
            900                 905                 910

Gly Val Ile Val Asp Gly Ser Ile Leu Ile Tyr Ser Ser Cys Ser Ala
        915                 920                 925
```

His Tyr Asn Ser Gly Gln Arg Pro Ala Gly Thr Trp Arg Cys Met Gly
            930                 935                 940

Tyr Val Leu Asn Arg Asp Ala Arg Asp Pro Asp Ser Ala Thr Leu Phe
945                 950                 955                 960

Gln Arg Val Thr

<210> SEQ ID NO 50
<211> LENGTH: 964
<212> TYPE: PRT
<213> ORGANISM: bacteriohage Phi33

<400> SEQUENCE: 50

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ile Asp Pro Leu Ser Ser Thr Thr Trp Glu Glu Gln Pro Ala
        115                 120                 125

Trp Ser Val Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

```
Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                    405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
            435                 440                 445

Gln Pro Arg Leu Asp Val Ala Lys Asn Leu Ala Tyr Ile Ala Asn Ser
            450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                    485                 490                 495

Asn Thr Thr Asn Pro Asp Gly Ser Tyr Arg Ser Gln Ile Met Arg Trp
            500                 505                 510

Asp Trp Ala Ser Thr Asn Val Ile Phe Asn Asn Arg Pro Leu Phe Ala
            515                 520                 525

Gly Gln Tyr Val Pro Trp Asp Ser Gly Asn Phe Asp Pro Ser Thr Lys
            530                 535                 540

Leu Thr Val Asn Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
                    565                 570                 575

Thr Thr Ala Ser Tyr Gly Asn Ala Ala Leu Gln Ile Phe Gly Lys Gly
            580                 585                 590

Gly Gly Glu Pro Ala Ala Leu Tyr Phe Asp Asn Ser Gln Thr Gly Trp
            595                 600                 605

Tyr Leu Gly Met Asp Lys Asp Gly Gln Leu Lys Arg Ala Gly Trp Ser
            610                 615                 620

Leu Gly Asn Asn Ala Tyr Val Ile Thr Asp Glu Ser Asn Ile Arg Phe
625                 630                 635                 640

His Val Asn Ser Met Ala Gly Thr Pro Val Trp Gly Gly Asn Glu Phe
                    645                 650                 655

Trp Gly Pro Trp Asn Phe Asn Pro Asn Thr Lys Leu Thr Ile Lys Ala
            660                 665                 670

Gly Thr Gln Glu Thr Ser Ser Thr Ala Ile Phe Ser Gly Thr Met Pro
            675                 680                 685

Phe Ala Pro Ile Ala Ser Leu Ser Asp Tyr Ser Gln Ala Pro Leu Thr
            690                 695                 700

Val Tyr Asn Ala Pro Thr Gly Pro Ser Ala Lys Pro Ala Val Ile Ala
705                 710                 715                 720

Phe Ile Arg Pro Gly Asn Trp Gly Ala Phe Phe Gly Ile Asp Thr Asp
                    725                 730                 735

Asn Lys Leu Lys Trp Gly Gly Gly Ser Leu Gly Asn Ser Ser Arg Glu
            740                 745                 750
```

```
Ile Ala Asp Ser Ser Asn Ile Met Asn Leu Trp Ala Asn Pro Thr
            755                 760                 765
Ala Pro Ser Trp Asn Gly Gln Thr Ile Trp Arg Ser Gly Asn Phe Asp
770                 775                 780
Pro Ala Thr Lys Val Asp Leu Asn Ala Ala Asn Ala Thr Asn Gly Asn
785                 790                 795                 800
Met Ile Phe Asn Arg Ile Ala Gly Thr Gly Ser Gly Ile Ala Ser Ser
                805                 810                 815
Gly Arg Val Gly Ala Ile Asn Leu Gln Asn Gly Glu His Ser Gly Gln
            820                 825                 830
Ala Ala Ala Val Thr Phe Glu Arg Gly Gly Ser Ile Phe Val Asn Phe
            835                 840                 845
Gly Leu Asp Thr Asp Asn Val Leu Lys Val Gly Gly Asn Leu Gly
            850                 855                 860
Ala Asn Ala Tyr Pro Val Ile His Ala Gly Asn Tyr Asn Asn Tyr Ile
865                 870                 875                 880
Asn Gln Ala Leu Val Gln Val Gly Leu Glu Gly Val Gly Ser Tyr Gly
                885                 890                 895
Ile Phe Ala Val Leu Asp Asn Ala Ala Pro Thr Ala Thr Val Gln Pro
                900                 905                 910
Gly Val Val Asp Gly Ser Ile Leu Ile Tyr Ser Ser Cys Ala Ala
            915                 920                 925
Asn Tyr Asn Ser Gly Lys Arg Pro Ala Gly Thr Trp Arg Cys Met Gly
            930                 935                 940
Tyr Val Val Asn Arg Asp Ala Asn Thr Pro Asp Ser Ala Thr Leu Phe
945                 950                 955                 960
Gln Arg Val Thr

<210> SEQ ID NO 51
<211> LENGTH: 964
<212> TYPE: PRT
<213> ORGANISM: bacteriohage LMA2

<400> SEQUENCE: 51

Met Ile Thr Pro Glu Leu Ile Pro Ser Pro Phe Ala Ala Gln Gly Asp
1               5                   10                  15
Lys Asp Pro Ile Pro Gln Thr Ser Ser Thr Gly Phe Ala Asn Leu Arg
                20                  25                  30
Asp Gly Tyr Thr Pro Asp Tyr Glu Ile Ser Leu Ala Ser Asn Asn Pro
            35                  40                  45
Gln Ala Lys Val Val Glu Arg Lys Ile Gln Asn Gln Leu Phe Phe Ile
    50                  55                  60
Ala Thr Gln Asn Ala Gln Ala Trp Gln Arg Gln Met Ala Pro Pro Trp
65                  70                  75                  80
Phe Gln Gly Met Pro Gly Gly Tyr Glu Gln Asn Ala Glu Val Val Arg
                85                  90                  95
Val Gly Asn Asp Gly Ile Met Arg Arg Tyr Arg Ser Met Val Asn Ala
                100                 105                 110
Asn Ala Ser Asp Pro Leu Ser Ser Thr Thr Trp Glu Glu Gln Pro Ala
            115                 120                 125
Trp Ser Ala Met Arg Ser Asn Ile Pro Met Pro Ala Gly Gly Pro Gly
    130                 135                 140
Leu Ser Ser Gly Gly Glu Val Ile Thr Thr Gly Arg Asn Phe Asn Asp
145                 150                 155                 160
```

-continued

Leu Leu Asn Gly Thr Trp Glu Phe Phe Ser Asp Ser Val Val Ile Ala
              165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
            195                 200                 205

Gln Arg Tyr Thr Asp Arg Val Gly Asn Val Ala Val Arg Gly Leu Asn
            210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
            245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Thr Thr
            275                 280                 285

Ile Asn Val Ser Gly Leu Gly Ala Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
            325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
            405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
            435                 440                 445

Gln Pro Arg Leu Asp Val Ala Lys Asn Leu Ala Tyr Ile Ala Asn Ser
            450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
            485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
            530                 535                 540

Leu Thr Val Asn Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
            565                 570                 575

Thr Thr Ala Ser Tyr Gly Asn Ala Ala Ile Gln Ile Phe Gly Lys Gly

```
                580             585             590
Gly Gly Glu Pro Ala Ile Tyr Phe Asp Asn Ser Gln Thr Gly Trp
            595             600             605

Tyr Leu Gly Met Asp Lys Asp Gly Gln Leu Lys Arg Ala Gly Trp Ser
        610             615             620

Leu Gly Asn Asn Ser Tyr Val Ile Thr Asp Glu Leu Asn Ile Arg Asn
625             630             635             640

His Ile Asn Gly Met Ala Ala Arg Pro Val Trp Gly Gly Asn Glu Phe
            645             650             655

Trp Gly Pro Trp Asn Phe Asn Pro Asn Thr Lys Leu Thr Ile Lys Ala
        660             665             670

Gly Thr Gln Glu Thr Ser Ser Thr Ala Ile Tyr Ser Gly Thr Met Pro
        675             680             685

Phe Ala Pro Ile Ala Ser Leu Ser Asp Tyr Ser Gln Ala Pro Leu Thr
        690             695             700

Ile Tyr Asn Ala Pro Thr Gly Pro Ser Ala Lys Pro Ala Val Ile Ala
705             710             715             720

Phe Ile Arg Pro Gly Asn Trp Gly Ala Phe Phe Gly Leu Asp Thr Asp
            725             730             735

Asn Lys Leu Lys Trp Gly Gly Ser Leu Gly Asn Ser Ser Met Glu
        740             745             750

Ile Ala Asp Ser Ser Asn Ile Met Asn Leu Trp Ala Ala Asn Pro Thr
        755             760             765

Ala Pro Thr Trp Asn Gly Gln Thr Val Trp Arg Ser Gly Asn Phe Asp
770             775             780

Pro Ala Thr Lys Val Asp Leu Asn Ala Pro Asn Ala Thr Asn Gly Asn
785             790             795             800

Met Ile Phe Asn Arg Ile Ala Gly Thr Gly Ser Gly Ile Ala Ser Ser
            805             810             815

Gly Arg Val Gly Ala Ile Ser Leu Gln Asn Gly Ala Thr Ala Gly Ala
        820             825             830

Ala Ala Ala Val Thr Phe Glu Arg Gly Gly Gly Phe Phe Val Asn Phe
        835             840             845

Gly Leu Asp Thr Asp Asn Val Leu Lys Val Gly Gly Gly Asn Leu Gly
        850             855             860

Ala Asn Ala Tyr Pro Val Ile His Ala Gly Asn Tyr Asn Ser Tyr Ile
865             870             875             880

Asn Gln Ala Leu Val Gln Val Gly Leu Gly Gly Val Gly Ser Tyr Ala
            885             890             895

Ala Leu Ala Val Tyr Asp Thr Ser Ala Pro Ala Ser Ser Val Gly Pro
        900             905             910

Gly Thr Ile Leu Asp Gly Ser Val Leu Phe Tyr Ser Ser Phe Asn Ala
        915             920             925

Asn Phe Arg Ser Gly Thr Lys Pro Thr Gly Thr Trp Arg Cys Met Gly
        930             935             940

Tyr Ile Leu Asn Arg Asp Gly Thr Asn Pro Asp Ser Ala Thr Leu Phe
945             950             955             960

Gln Arg Val Thr

<210> SEQ ID NO 52
<211> LENGTH: 963
<212> TYPE: PRT
<213> ORGANISM: bacteriohage KPP12
```

-continued

<400> SEQUENCE: 52

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Ala Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Leu Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
                405                 410                 415
```

```
Ser Glu Ala Asp Gly Ser Met Ala Phe Tyr Ser Arg Gln Gly Ser Ala
            420                 425                 430

Gly Pro Thr Gln Asp Ile Leu Phe Ser Arg Ser Asn Val Thr Phe Leu
            435                 440                 445

Gln Pro Arg Leu Asp Val Ala Lys Asn Leu Ala Tyr Ile Ala Asn Ser
        450                 455                 460

Gly Ser Leu Trp Gln Asn Thr Thr Ala Asp Gln Pro Gly Trp Lys Phe
465                 470                 475                 480

Thr Phe Ala Gln Gly Val Asp Ala Asn Asn Asn Ala Val Ile Ala Val
                485                 490                 495

Asn Thr Thr Asn Pro Asp Gly Ser Tyr Arg Ser Gln Ile Met Arg Trp
                500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
        530                 535                 540

Leu Thr Val Asn Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Ser Ser
                565                 570                 575

Thr Thr Ala Ser Tyr Gly Asn Ala Ala Leu Gln Ile Phe Gly Lys Gly
                580                 585                 590

Gly Gly Glu Pro Ala Ala Leu Tyr Phe Asp Asn Ser Gln Thr Gly Trp
            595                 600                 605

Tyr Leu Gly Met Asp Lys Asp Gly Gln Leu Lys Arg Ala Gly Trp Ser
        610                 615                 620

Leu Gly Asn Asn Ala Tyr Val Ile Thr Asp Glu Ser Asn Ile Arg Phe
625                 630                 635                 640

His Val Asn Ser Met Ala Gly Thr Pro Val Trp Gly Asn Glu Phe
                645                 650                 655

Trp Gly Ser Trp Asn Phe Asn Pro Asn Thr Lys Leu Thr Ile Lys Ala
            660                 665                 670

Gly Thr Gln Glu Thr Ser Ser Thr Ala Ile Phe Ser Glu Thr Met Pro
        675                 680                 685

Phe Ala Pro Ile Ala Ser Leu Ser Asp Tyr Ser Gln Ala Pro Leu Thr
690                 695                 700

Ile Tyr Asn Ala Pro Thr Gly Pro Ser Ala Lys Pro Ala Val Ile Ala
705                 710                 715                 720

Phe Ile Arg Pro Gly Asn Trp Gly Ala Phe Phe Gly Leu Asp Thr Asp
            725                 730                 735

Asn Lys Leu Lys Trp Gly Gly Ser Leu Gly Asn Ser Ser Arg Glu
            740                 745                 750

Ile Ala Asp Ser Arg Asn Ile Met Asn Leu Trp Ala Ala Asn Pro Thr
        755                 760                 765

Ala Pro Thr Trp Asn Gly Gln Thr Val Trp Arg Ser Gly Asn Phe Asp
        770                 775                 780

Pro Ala Thr Lys Val Asp Leu Asn Ala Pro Asn Ala Thr Asn Gly Asn
785                 790                 795                 800

Met Ile Phe Asn Arg Ile Ala Gly Thr Gly Ser Gly Ile Ala Ser Ser
                805                 810                 815

Gly Arg Val Gly Ala Ile Ser Leu Gln Asn Gly Ala Thr Ala Gly Ala
            820                 825                 830
```

```
Ala Ala Ala Val Thr Phe Glu Arg Gly Gly Phe Phe Val Asn Phe Gly
            835                 840                 845

Leu Asp Thr Asp Asn Val Leu Lys Val Gly Gly Asn Leu Gly Ala
850                 855                 860

Asn Ala Tyr Pro Val Ile His Ala Gly Asn Tyr Asn Ser Tyr Ile Asn
865                 870                 875                 880

Gln Ala Leu Val Gln Val Gly Leu Gly Gly Val Gly Ser Tyr Ala Ala
                885                 890                 895

Leu Ala Val Tyr Asp Thr Ser Ala Pro Ala Ser Ser Val Gly Pro Gly
                900                 905                 910

Thr Ile Leu Asp Gly Ser Val Leu Phe Tyr Ser Ser Phe Asp Ala Asn
                915                 920                 925

Phe Arg Ser Gly Thr Lys Pro Thr Gly Thr Trp Arg Cys Met Gly Tyr
                930                 935                 940

Val Leu Asn Arg Asp Gly Thr Asn Pro Asp Ser Ala Ala Leu Phe Gln
945                 950                 955                 960

Arg Val Thr

<210> SEQ ID NO 53
<211> LENGTH: 962
<212> TYPE: PRT
<213> ORGANISM: bacriohage JG024

<400> SEQUENCE: 53

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
                35                  40                  45

Gln Ala Lys Ala Val Glu Arg Lys Ile Gln Asn Gln Leu Phe Phe Ile
50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
                100                 105                 110

Asn Ala Ser Asp Pro Leu Ser Ser Thr Thr Trp Glu Glu Pro Ala
                115                 120                 125

Trp Ser Val Met Arg Thr Asn Ile Pro Met Pro Ala Gly Gly Pro Gly
130                 135                 140

Leu Ser Ser Gly Gly Glu Val Ile Thr Thr Gly Arg Asn Phe Asn Glu
145                 150                 155                 160

Leu Leu Asn Gly Thr Trp Glu Phe Phe Ser Asp Ala Ile Val Val Ala
                165                 170                 175

Ser Gln Asn Ala Pro Val Tyr Pro Ala Ser Ala Gly Ala Ala Ala Gly
                180                 185                 190

Met Leu Glu Ala Lys Ser Trp Val Ser Gly Ser Asn Thr Phe Cys Val
                195                 200                 205

Gln Arg Tyr Thr Asp Arg Val Gly Asn Val Ala Val Arg Gly Leu Asn
                210                 215                 220

Ala Gly Ala Trp Thr Asn Trp Met Tyr Ala Val Asn Val Met Ala Leu
225                 230                 235                 240
```

-continued

```
Gln His Gly Arg Val Thr Tyr Gly Thr Ala Gly Pro Ala Asn Ala
            245                 250                 255
Tyr Thr Leu Thr Leu Val Pro Gln Ile Gln Gly Gly Leu Val Asp Gly
        260                 265                 270
Met Ile Leu Arg Val Lys Phe Asn Thr Met Asn Thr Gly Ala Thr Thr
        275                 280                 285
Ile Asn Val Ser Gly Leu Gly Ala Lys Ala Ile Val Gly Ala Ala Asn
    290                 295                 300
Phe Pro Leu Thr Gly Gly Glu Leu Gly Gln Gly Leu Ile Ala Glu Leu
305                 310                 315                 320
Val Phe Asp Ala Ala Gly Asp Arg Trp Arg Ile Leu Ala Gly Ala Pro
                325                 330                 335
Arg Ile Gln Val Gly Asn Ala Asp Gln Asp Tyr Gln Ala Pro Ser Trp
            340                 345                 350
Lys Gln Val Lys Asp Tyr Val Glu Ser Gln Lys Leu Thr Glu Val Asp
        355                 360                 365
Trp Thr Asp Val Val Asn Lys Pro Asn Val Ala Ile Gln Asp Thr Thr
    370                 375                 380
Pro Trp Phe Ala Asn Leu Glu Leu Ser Asp Ala Arg Pro Phe Ile Asp
385                 390                 395                 400
Phe His Phe Asn Ser Asn Arg Ala Lys Asp Phe Asp Tyr Arg Leu Ile
                405                 410                 415
Ser Glu Ala Asp Gly Ser Leu Ala Phe Tyr Ser Arg Gln Gly Ser Ala
            420                 425                 430
Gly Pro Thr Gln Asp Ile Leu Phe Asn Arg Asn Ser Val Thr Phe Phe
        435                 440                 445
Gln Pro Arg Leu Asp Val Ala Lys Asn Leu Ala Tyr Ile Ala Asn Ser
    450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
                485                 490                 495
Asn Thr Thr Asn Pro Asp Gly Ser Tyr Arg Ser Gln Val Met Arg Trp
            500                 505                 510
Asp Trp Ala Ser Thr Asn Val Ile Phe Asn Asn Arg Pro Leu Phe Ala
        515                 520                 525
Gly Gln Tyr Thr Pro Trp Asp Ser Gly Asn Phe Asp Pro Ser Thr Lys
    530                 535                 540
Leu Thr Val Ser Ala Thr Asn Gln Ile Ser Gly Pro Thr Gly Ile Arg
545                 550                 555                 560
Asn Thr Asn Gly Asn Thr Gly Asn Met Asn Thr Trp Gly Ser Gly Ser
                565                 570                 575
Thr Thr Ala Ser Tyr Gly Asn Ala Ala Ile Gln Ile Phe Gly Lys Gly
            580                 585                 590
Gly Gly Glu Pro Ala Ala Ile Tyr Phe Asp Asn Ser Gln Thr Gly Trp
        595                 600                 605
Tyr Leu Gly Met Asp Lys Asp Gly Gln Leu Lys Arg Ala Gly Trp Ser
    610                 615                 620
Leu Gly Asn Asn Ser Tyr Val Ile Thr Asp Glu Ser Asn Ile Arg Thr
625                 630                 635                 640
His Ile Asn Thr Met Ala Ala Arg Pro Ile Trp Gly Asn Val Glu Phe
                645                 650                 655
Trp Gly Pro Trp Asn Phe Asp Pro Asn Leu Lys Leu Thr Leu Asn Ala
```

```
                    660                 665                 670
Phe Asn Asp Ser Ser Tyr Thr Arg Met Thr Asn Ser Gly Ala Lys Asp
            675                 680                 685

Val Gly Ile Ala Ser Met Thr Ser Tyr Ala Asp Ala Ala Met Ser Phe
        690                 695                 700

Phe Asn Tyr Glu Ala Ser Asn Pro Thr Gly Pro Arg Ala Ala Val Ile
705                 710                 715                 720

Ser Phe Val Arg Asn Gly Ser Arg Gly Val Leu Phe Gly Leu Asp Ser
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
        770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Gly Thr Met Gly Gly Val
850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Ala Ile Leu
                885                 890                 895

Ala Val Leu Asp Thr Ser Ala Pro Ala Ala Ser Ile Ala Pro Gly Thr
            900                 905                 910

Ile Met Asp Ser Ser Lys Leu Phe Tyr Ser Ser Cys Asp Ser Thr Tyr
        915                 920                 925

Arg Ser Ser Ala Ser Pro Thr Gly Thr Trp Arg Cys Met Gly Tyr Val
        930                 935                 940

Tyr Asn Arg Asp Ser Thr Asn Gly Asp Ser Ala Ser Leu Phe Gln Arg
945                 950                 955                 960

Val Thr

<210> SEQ ID NO 54
<211> LENGTH: 962
<212> TYPE: PRT
<213> ORGANISM: bacteriohage PTP92

<400> SEQUENCE: 54

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
```

```
                65                  70                  75                  80
        Phe Gln Gly Met Pro Gly Gly Tyr Glu Gln Asn Ala Glu Val Val Arg
                            85                  90                  95

Val Gly Asn Asp Gly Ile Met Arg Arg Tyr Arg Ser Met Val Asn Ala
                           100                 105                 110

Asn Ala Ser Asp Pro Leu Ser Thr Thr Trp Glu Gln Pro Ala
                           115                 120                 125

Trp Ser Val Met Arg Thr Asn Ile Pro Met Pro Ala Gly Gly Pro Gly
                           130                 135                 140

Leu Ser Ser Gly Gly Glu Val Ile Thr Thr Gly Arg Asn Phe Asn Glu
        145                 150                 155                 160

Leu Leu Asn Gly Thr Trp Glu Phe Phe Ser Asp Ala Ile Val Val Ala
                           165                 170                 175

Ser Gln Asn Ala Pro Val Tyr Pro Ala Ser Ala Gly Ala Ala Ala Gly
                           180                 185                 190

Met Leu Glu Ala Lys Ser Trp Val Ser Gly Ser Asn Thr Phe Cys Val
                           195                 200                 205

Gln Arg Tyr Thr Asp Arg Val Gly Asn Val Ala Val Arg Gly Leu Asn
                           210                 215                 220

Ala Gly Ala Trp Thr Asn Trp Met Tyr Ala Val Asn Val Met Ala Leu
        225                 230                 235                 240

Gln His Gly Arg Val Thr Tyr Gly Thr Ala Ala Gly Pro Ala Asn Ala
                           245                 250                 255

Tyr Thr Leu Thr Leu Val Pro Gln Ile Gln Gly Gly Leu Val Asp Gly
                           260                 265                 270

Met Ile Leu Arg Val Lys Phe Asn Thr Met Asn Thr Gly Ala Thr Thr
                           275                 280                 285

Ile Asn Val Ser Gly Leu Gly Ala Lys Ala Ile Val Gly Ala Ala Asn
                           290                 295                 300

Phe Pro Leu Thr Gly Gly Glu Leu Gly Gln Gly Leu Ile Ala Glu Leu
        305                 310                 315                 320

Val Phe Asp Ala Ala Gly Asp Arg Trp Arg Ile Leu Ala Gly Ala Pro
                           325                 330                 335

Arg Ile Gln Val Gly Asn Ala Asp Gln Asp Tyr Gln Ala Pro Ser Trp
                           340                 345                 350

Lys Gln Val Lys Asp Tyr Val Glu Ser Gln Lys Leu Thr Glu Val Asp
                           355                 360                 365

Trp Thr Asp Val Val Asn Lys Pro Asn Val Ala Ile Gln Asp Thr Thr
        370                 375                 380

Pro Trp Phe Ala Asn Leu Glu Leu Ser Asp Ala Arg Pro Phe Ile Asp
        385                 390                 395                 400

Phe His Phe Asn Ser Asn Arg Ala Lys Asp Phe Asp Tyr Arg Leu Ile
                           405                 410                 415

Ser Glu Ala Asp Gly Ser Leu Ala Phe Tyr Ser Arg Gln Gly Ser Ala
                           420                 425                 430

Gly Pro Thr Gln Asp Ile Leu Phe Asn Arg Asn Ser Val Thr Phe Phe
                           435                 440                 445

Gln Pro Arg Leu Asp Val Ala Lys Asn Leu Ala Tyr Ile Ala Asn Ser
                           450                 455                 460

Gly Pro Leu Trp Gln Asn Thr Thr Ala Asp Gln Pro Gly Trp Lys Phe
        465                 470                 475                 480

Thr Phe Ala Gln Gly Val Asp Ala Asn Asn Asn Ala Val Ile Ala Val
                           485                 490                 495
```

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
        515                 520                 525

Gly Gln Tyr Thr Pro Trp Asp Ser Gly Asn Phe Asp Pro Ser Thr Lys
    530                 535                 540

Leu Thr Val Ser Ala Thr Asn Gln Ile Ser Gly Pro Thr Gly Ile Arg
545                 550                 555                 560

Asn Thr Asn Gly Asn Thr Gly Asn Met Asn Thr Trp Gly Ser Gly Ser
            565                 570                 575

Thr Thr Ala Ser Tyr Gly Asn Ala Ala Ile Gln Ile Phe Gly Lys Gly
        580                 585                 590

Gly Gly Glu Pro Ala Ala Ile Tyr Phe Asp Asn Ser Gln Thr Gly Trp
    595                 600                 605

Tyr Leu Gly Met Asp Lys Asp Gly Gln Leu Lys Arg Ala Gly Trp Ser
    610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
            645                 650                 655

Trp Gly Pro Trp Asn Phe Asp Pro Asn Leu Lys Leu Thr Leu Asn Ala
        660                 665                 670

Phe Asn Asp Ser Ser Tyr Thr Arg Met Thr Asn Ser Gly Ala Lys Asp
    675                 680                 685

Val Gly Ile Ala Ser Met Thr Ser Tyr Ala Asp Ala Ala Met Ser Phe
    690                 695                 700

Phe Asn Tyr Glu Ala Ser Asn Pro Thr Gly Pro Arg Ala Ala Val Ile
705                 710                 715                 720

Ser Phe Val Arg Asn Gly Ser Arg Gly Val Leu Phe Gly Leu Asp Ser
            725                 730                 735

Asp Asn Lys Leu Lys Trp Gly Gly Tyr Ser Leu Gly Ala Val Ala Phe
        740                 745                 750

Glu Ile Ala Asp Ser Asn Asn Leu Met Ser Leu Trp Ser Ser His Ala
    755                 760                 765

Ala Ala Pro Asn Trp Asn Gly Gln Thr Ile Trp Arg Ser Gly Asn Phe
    770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
            805                 810                 815

Val Gly Ala Leu Val Val Glu Asn Asn Ser Val Thr Asn Thr Ala Ala
        820                 825                 830

Ala Ile Thr Phe His Ser Pro Gln Lys Tyr Gln Val Asn Phe Gly Leu
    835                 840                 845

Asp Ala Asp Asn Val Val Lys Ile Gly Gly Gly Thr Met Gly Gly Val
    850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Ala Ile Leu
            885                 890                 895

Ala Val Leu Asp Thr Ser Ala Pro Ala Ala Ser Ile Ala Pro Gly Thr
        900                 905                 910

```
Ile Met Asp Ser Ser Lys Leu Phe Tyr Ser Ser Cys Asp Ser Thr Tyr
            915                 920                 925

Arg Ser Ser Ala Ser Pro Thr Gly Thr Trp Arg Cys Met Gly Tyr Val
            930                 935                 940

Tyr Asn Arg Asp Ser Thr Asn Gly Asp Ser Ala Ser Leu Phe Gln Arg
945                 950                 955                 960

Val Thr

<210> SEQ ID NO 55
<211> LENGTH: 962
<212> TYPE: PRT
<213> ORGANISM: bacteriohage NH-4

<400> SEQUENCE: 55

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Arg Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Thr Asn Ile Pro Met Pro Ala Gly Gly Pro Gly
130                 135                 140

Leu Ser Ser Gly Gly Glu Val Ile Thr Thr Gly Arg Asn Phe Asn Glu
145                 150                 155                 160

Leu Leu Asn Gly Thr Trp Glu Phe Phe Ser Asp Ala Ile Val Val Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ser Asn Thr Phe Cys Val
        195                 200                 205

Gln Arg Tyr Thr Asp Arg Val Gly Asn Val Ala Val Arg Gly Leu Asn
210                 215                 220

Ala Gly Ala Trp Thr Asn Trp Met Tyr Ala Val Asn Val Met Ala Leu
225                 230                 235                 240

Gln His Gly Arg Val Thr Tyr Gly Thr Ala Ala Gly Pro Ala Asn Ala
                245                 250                 255

Tyr Thr Leu Thr Leu Val Pro Gln Ile Gln Gly Gly Leu Val Asp Gly
            260                 265                 270

Met Ile Leu Arg Val Lys Phe Asn Thr Met Asn Thr Gly Ala Thr Thr
        275                 280                 285

Ile Asn Val Ser Gly Leu Gly Ala Lys Ala Ile Val Gly Ala Ala Asn
290                 295                 300

Phe Pro Leu Thr Gly Gly Glu Leu Gly Gln Gly Leu Ile Ala Glu Leu
305                 310                 315                 320
```

```
Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Thr Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
    450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
        515                 520                 525

Gly Gln Tyr Thr Pro Trp Asp Ser Gly Asn Phe Asp Pro Ser Thr Lys
    530                 535                 540

Leu Thr Val Ser Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Gln Leu Lys Arg Ala Gly Trp Ser
    610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asn Pro Asn Thr Lys Leu Thr Leu Gly Ser
            660                 665                 670

Phe Asn Asp Ser Gln His Thr Arg Met Val Asn Ser Ala Ala Lys Asp
        675                 680                 685

Val Gly Ile Ala Ser Met Thr Ser Tyr Ala Asp Ala Ala Met Ser Phe
    690                 695                 700

Phe Asn Tyr Glu Ala Ser Thr Pro Thr Gly Asn Arg Ala Ala Val Ile
705                 710                 715                 720

Ser Phe Val Arg Asn Gly Ala Arg Gly Val Leu Phe Gly Leu Asp Thr
                725                 730                 735

Asp Asn Lys Leu Lys Trp Gly Gly Tyr Ser Leu Gly Ala Val Ala Phe
```

```
                    740                 745                 750
Glu Ile Ala Asp Ser Asn Asn Leu Met Ser Leu Trp Ser Ser His Ala
                755                 760                 765

Ala Ala Pro Asn Trp Asn Gly Gln Thr Ile Trp Arg Ser Gly Asn Phe
        770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Thr Met Gly Gly Val
    850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Ala Ile Leu
                885                 890                 895

Ala Val Leu Asp Thr Ser Ala Pro Ala Ala Ser Ile Ala Pro Gly Thr
            900                 905                 910

Ile Met Asp Ser Ser Lys Leu Phe Tyr Ser Ser Cys Asp Ser Thr Tyr
        915                 920                 925

Arg Ser Ser Ala Arg Pro Thr Gly Thr Trp Arg Cys Met Gly Tyr Val
    930                 935                 940

Tyr Asn Arg Asp Ser Thr Asn Gly Asp Ser Ala Ser Leu Phe Gln Arg
945                 950                 955                 960

Val Thr

<210> SEQ ID NO 56
<211> LENGTH: 962
<212> TYPE: PRT
<213> ORGANISM: bacteriohage 14-1

<400> SEQUENCE: 56

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Thr Thr Trp Glu Gln Pro Ala
        115                 120                 125

Trp Ser Val Met Arg Ser Ile Pro Met Pro Ala Gly Gly Pro Gly
    130                 135                 140

Leu Ser Ser Gly Gly Glu Val Ile Thr Thr Gly Arg Asn Phe Asn Asp
```

```
            145                 150                 155                 160
Leu Leu Asn Gly Thr Trp Glu Phe Phe Ser Asp Ser Val Val Ile Ala
                165                 170                 175
Ser Gln Asn Ala Pro Val Tyr Pro Ala Ser Ala Gly Ala Ala Ala Gly
                180                 185                 190
Met Leu Glu Ala Lys Ser Trp Ile Ser Arg Ser Asn Thr Phe Cys Val
                195                 200                 205
Gln Arg Tyr Thr Asp Arg Val Gly Asn Val Ala Val Arg Gly Leu Asn
            210                 215                 220
Ala Gly Glu Trp Thr Asn Trp Met Tyr Ala Val Asn Val Met Ala Leu
225                 230                 235                 240
Gln Gln Gly Arg Val Thr Tyr Gly Val Ala Ala Gly Pro Ala Asn Ala
                245                 250                 255
Tyr Thr Leu Thr Leu Val Pro Gln Leu Gln Gly Gly Leu Val Asp Gly
                260                 265                 270
Met Ile Leu Arg Val Lys Phe Asn Thr Val Asn Thr Gly Ala Ser Thr
                275                 280                 285
Ile Asn Val Ser Gly Leu Gly Ala Lys Ala Ile Val Gly Ala Ala Asn
            290                 295                 300
Phe Pro Leu Thr Gly Gly Glu Leu Gly Gln Gly Leu Ile Ala Glu Leu
305                 310                 315                 320
Val Phe Asp Ala Ala Gly Asp Arg Trp Arg Ile Leu Ala Gly Ala Pro
                325                 330                 335
Arg Ile Gln Val Gly Asn Ala Asp Gln Asp Tyr Gln Ala Pro Ser Trp
                340                 345                 350
Lys Gln Val Lys Asp Tyr Val Ala Ser Gln Lys Leu Thr Glu Val Asp
                355                 360                 365
Trp Thr Asp Val Val Asn Lys Pro Asn Val Ala Ile Gln Asp Thr Thr
                370                 375                 380
Pro Trp Phe Ala Asn Leu Glu Leu Ser Asp Ala Arg Pro Phe Ile Asp
385                 390                 395                 400
Phe His Phe Asn Ser Asn Arg Ala Lys Asp Phe Asp Tyr Arg Leu Ile
                405                 410                 415
Ser Glu Ala Asp Gly Ser Leu Ala Phe Tyr Ser Arg Gln Gly Ser Ala
                420                 425                 430
Gly Pro Thr Gln Asp Ile Leu Phe Asn Arg Asn Ser Val Thr Phe Phe
                435                 440                 445
Gln Pro Arg Leu Asp Val Ala Lys Asn Leu Ala Tyr Ile Ala Asn Ser
            450                 455                 460
Gly Pro Ile Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
                485                 490                 495
Asn Thr Thr Asn Pro Asp Gly Ser Tyr Arg Ser Gln Val Met Arg Trp
                500                 505                 510
Asp Trp Ala Ser Thr Asn Val Ile Phe Asn Asp Arg Pro Leu Phe Ala
            515                 520                 525
Gly Gln Tyr Thr Pro Trp Asp Ser Gly Asn Phe Asp Pro Ser Thr Lys
                530                 535                 540
Leu Thr Val Ser Ala Thr Asn Gln Ile Ala Gly Pro Thr Gly Ile Arg
545                 550                 555                 560
Asn Thr Asn Gly Asn Thr Gly Asn Met Asn Thr Trp Gly Ser Gly Ser
                565                 570                 575
```

-continued

```
Thr Thr Ala Ser Tyr Gly Asn Ala Ala Ile Gln Ile Phe Gly Lys Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Arg Leu Lys Arg Ala Gly Trp Ser
    610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asp Pro Asn Leu Lys Leu Thr Leu Asn Ala
            660                 665                 670

Phe Asn Asp Ser Ser Tyr Thr Arg Met Thr Asn Ser Gly Ala Lys Asp
        675                 680                 685

Val Gly Ile Ala Ser Met Thr Ser Tyr Ala Asp Ala Ala Met Ser Phe
    690                 695                 700

Phe Asn Tyr Glu Ala Ser Asn Pro Thr Gly Pro Arg Ala Ala Val Ile
705                 710                 715                 720

Ser Phe Val Arg Asn Gly Ser Arg Gly Val Leu Phe Gly Leu Asp Ser
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
    770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Gly Thr Met Gly Gly Val
    850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Val Gly Ser Tyr Gly Ile Phe
                885                 890                 895

Ala Val Leu Asp Asn Ala Ala Pro Ile Ala Thr Val Gln Pro Gly Val
        900                 905                 910

Val Val Asp Gly Ser Ile Leu Ile Tyr Ser Ser Cys Ala Ala Asn Tyr
    915                 920                 925

Asn Ser Gly Gln Arg Pro Ala Gly Thr Trp Arg Cys Met Gly Tyr Val
930                 935                 940

Val Asn Arg Asp Ala Asn Thr Pro Asp Ser Ala Thr Leu Phe Gln Arg
945                 950                 955                 960

Val Thr

<210> SEQ ID NO 57
<211> LENGTH: 962
<212> TYPE: PRT
```

<213> ORGANISM: bacteriohage PTP47

<400> SEQUENCE: 57

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Asp Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Pro Ala
        115                 120                 125

Trp Ser Ala Met Arg Ser Asn Ile Pro Met Pro Ala Gly Gly Pro Gly
    130                 135                 140

Leu Ser Ser Gly Gly Glu Val Ile Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Ala Gly Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Thr Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400
```

```
Phe His Phe Asn Ser Asn Arg Ala Lys Asp Phe Asp Tyr Arg Leu Ile
                405                 410                 415
Ser Glu Ala Asp Gly Ser Leu Ala Phe Tyr Ser Arg Gln Gly Ser Ala
            420                 425                 430
Gly Pro Thr Gln Asp Ile Leu Phe Asn Arg Asn Ser Val Thr Phe Phe
        435                 440                 445
Gln Pro Arg Leu Asp Val Ala Lys Asn Leu Ala Tyr Ile Ala Asn Ser
    450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
                485                 490                 495
Asn Thr Thr Asn Pro Asp Gly Ser Tyr Arg Ser Gln Val Met Arg Trp
                500                 505                 510
Asp Trp Ala Ser Thr Asn Val Ile Phe Asn Asn Arg Pro Leu Phe Ala
            515                 520                 525
Gly Gln Tyr Thr Pro Trp Asp Ser Gly Asn Phe Asp Pro Ser Thr Lys
        530                 535                 540
Leu Thr Val Ser Ala Thr Asn Gln Ile Ala Gly Pro Thr Gly Ile Arg
545                 550                 555                 560
Asn Thr Asn Gly Asn Thr Gly Asn Met Asn Thr Trp Gly Ser Gly Ser
                565                 570                 575
Thr Thr Ala Ser Tyr Gly Asn Ala Ala Ile Arg Ile Phe Gly Lys Gly
                580                 585                 590
Gly Gly Glu Pro Ala Ala Ile Tyr Phe Asp Asn Ser Gln Thr Gly Trp
            595                 600                 605
Tyr Leu Gly Met Asp Lys Asp Gly Gln Leu Lys Arg Ala Gly Trp Ser
        610                 615                 620
Leu Gly Asn Asn Ser Tyr Val Ile Thr Asp Glu Ser Asn Ile Arg Thr
625                 630                 635                 640
His Ile Asn Thr Met Ala Ala Arg Pro Ile Trp Gly Asn Val Glu Phe
                645                 650                 655
Trp Gly Pro Trp Asn Phe Asn Pro Asn Thr Lys Leu Thr Leu Gly Ser
                660                 665                 670
Phe Asn Asp Gly Gln His Thr Arg Met Val Asn Ser Ala Ala Lys Asp
            675                 680                 685
Val Gly Ile Ala Ser Met Thr Ser Tyr Ala Asp Ala Ala Met Ser Phe
        690                 695                 700
Phe Asn Tyr Glu Ala Ser Thr Pro Thr Gly Asn Arg Ala Ala Val Ile
705                 710                 715                 720
Ser Phe Val Arg Asn Gly Ala Arg Gly Val Leu Phe Gly Leu Asp Thr
                725                 730                 735
Asp Asn Lys Leu Lys Trp Gly Gly Tyr Ser Leu Gly Ala Val Ala Phe
                740                 745                 750
Glu Ile Ala Asp Ser Asn Asn Leu Met Ser Leu Trp Ser Ser His Ala
            755                 760                 765
Ala Ala Pro Asn Trp Asn Gly Gln Thr Ile Trp Arg Ser Gly Asn Phe
        770                 775                 780
Asn Pro Asp Thr Lys Ala Thr Leu Ala Ala Arg Asn Thr Thr Ser Ser
785                 790                 795                 800
Pro Thr Ile Phe Ser Tyr Gly Ala Ser Gly Ile Ala Ser Thr Gly Gln
                805                 810                 815
Val Gly Ala Leu Val Val Glu Asn Asn Ser Val Thr Asn Thr Ala Ala
```

```
                    820                 825                 830
Ala Ile Thr Phe His Ser Pro Gln Lys Tyr His Val Asn Phe Gly Leu
                835                 840                 845

Asp Ala Asp Asn Val Val Lys Ile Gly Gly Gly Thr Met Gly Gly Val
850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Glu Val Gly Ser Tyr Gly Ile Phe
                885                 890                 895

Ala Val Leu Asp Tyr Ala Ala Pro Thr Ala Thr Val Arg Pro Gly Val
                900                 905                 910

Val Val Asp Gly Ser Ile Leu Ile Tyr Ser Ser Cys Ala Ala Asn Tyr
                915                 920                 925

Asn Ser Gly Gln Arg Pro Ala Gly Thr Trp Arg Cys Met Gly Tyr Val
                930                 935                 940

Val Asn Arg Asp Ala Asn Thr Pro Asp Ser Ala Thr Leu Phe Gln Arg
945                 950                 955                 960

Val Thr

<210> SEQ ID NO 58
<211> LENGTH: 962
<212> TYPE: PRT
<213> ORGANISM: bacteriohage SN

<400> SEQUENCE: 58

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
                100                 105                 110

Asn Ala Ser Asp Pro Leu Ser Ser Thr Thr Trp Glu Glu Gln Pro Ala
            115                 120                 125

Trp Ser Val Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ala Asn Thr Phe Cys Val
    195                 200                 205

Gln Arg Tyr Thr Asp Arg Val Gly Asn Val Ala Val Arg Gly Leu Asn
210                 215                 220

Ala Gly Ala Trp Thr Asn Trp Met Tyr Ala Val Asn Val Met Ala Leu
```

```
            225                 230                 235                 240
Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
                260                 265                 270

Met Ile Leu Arg Val Lys Phe Asn Thr Met Asn Thr Gly Ala Ser Thr
                275                 280                 285

Ile Asn Val Ser Gly Leu Gly Ala Lys Ala Ile Val Gly Ala Ala Asn
290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
                340                 345                 350

Lys Gln Val Lys Asp Tyr Val Ala Ser Gln Lys Leu Thr Glu Val Asp
                355                 360                 365

Trp Ala Asp Val Val Asn Lys Pro Asn Val Ala Ile Gln Asp Thr Thr
370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
                420                 425                 430

Gly Pro Thr Gln Asp Ile Leu Phe Asn Arg Asn Ser Val Thr Phe Phe
                435                 440                 445

Gln Pro Arg Leu Asp Val Ala Lys Asn Leu Ala Tyr Ile Ala Asn Ser
                450                 455                 460

Gly Ser Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
                500                 505                 510

Asp Trp Ala Ser Thr Asn Val Ile Phe Asn Asn Arg Pro Leu Phe Ala
                515                 520                 525

Gly Gln Tyr Thr Pro Trp Asp Ser Gly Asn Phe Asp Pro Ser Thr Lys
                530                 535                 540

Leu Thr Val Arg Ala Thr Asn Gln Ile Ala Gly Pro Thr Gly Ile Gln
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
                580                 585                 590

Gly Gly Glu Pro Ala Ala Ile Tyr Phe Asp Asn Ser Gln Thr Gly Trp
                595                 600                 605

Tyr Leu Gly Met Asp Lys Asp Gly Gln Leu Lys Arg Ala Gly Trp Ser
                610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Gly Val Glu Phe
                645                 650                 655
```

Trp Gly Pro Trp Asn Phe Asn Pro Asn Thr Lys Leu Thr Leu Gly Ser
            660                 665                 670

Phe Asn Asp Ser Gln His Thr Arg Met Val Asn Ser Ala Ala Lys Asp
        675                 680                 685

Val Gly Ile Ala Ser Met Thr Ser Tyr Ala Asp Ala Ala Met Ser Phe
690                 695                 700

Phe Asn Tyr Glu Ala Ser Thr Pro Thr Gly Asn Arg Ala Ala Val Ile
705                 710                 715                 720

Ser Phe Val Arg Asn Gly Ala Arg Gly Val Leu Phe Gly Leu Asp Thr
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Thr Met Gly Gly Val
850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Gly Ile Phe
                885                 890                 895

Ala Val Leu Asp Asn Ala Ala Pro Thr Ala Thr Val Gln Pro Gly Val
            900                 905                 910

Val Val Asp Gly Ser Ile Leu Ile Tyr Ser Ser Cys Ala Ala Asn Tyr
        915                 920                 925

Asn Ser Gly Gln Arg Pro Ala Gly Thr Trp Arg Cys Met Gly Tyr Val
930                 935                 940

Val Asn Arg Asp Ala Asn Thr Pro Asp Ser Ala Thr Leu Phe Gln Arg
945                 950                 955                 960

Val Thr

<210> SEQ ID NO 59
<211> LENGTH: 219
<212> TYPE: DNA
<213> ORGANISM: Artificial Sequence
<220> FEATURE:
<223> OTHER INFORMATION: codon optimised_SASP-C

<400> SEQUENCE: 59
atggccaact accagaacgc gagcaaccgc aacagcagca acaagctggt cgcgccgggc      60
gcccaggccg ccatcgacca gatgaagttc gagatcgcga gcgagttcgg cgtgaacctc     120
ggcccggacg ccaccgcccg tgccaacggc tcggtcggcg gcgaaatcac caagcgcctg     180
gtgcagctgg cggaacagaa cctgggcggc aagtactga                            219

ANTI-BACTERIAL COMPOSITIONS COMPARING LYTIC MODIFIED BACTERIOPHAGE ENGINEERED TO INFECT AND KILL DIFFERENT TARGET BACTERIA

The present invention relates to a modified bacteriophage, uses thereof, and compositions containing the modified bacteriophage.

RELATED APPLICATION INFORMATION

This application is U.S. National Phase Application submitted under 35 U.S.C. 371 based on International Application No. PCT/EP2017/058470 filed Apr. 7, 2017 (published as WO2017/174810 on Oct. 12, 2017) which claims the benefit of United Kingdom Patent Application 1606319.0 filed Apr. 8, 2016, each of which is hereby incorporated by reference in its entirety.

Sequence Listing Disclosure

This application includes as part of its disclosure a biological sequence listing which is a being concurrently submitted through EFS-Web. Said biological sequence listing is contained in a file named "114329700003601" which was created on Feb. 13, 2023, and has a size of 120,455 bytes, and is hereby incorporated by reference in its entirety.

BACKGROUND TO THE INVENTION

The World Health Organisation's 2014 report on global surveillance of antimicrobial resistance reveals that antibiotic resistance is a global problem that is jeopardising the ability to treat common infections in the community and hospitals. Without urgent action, the world is heading towards a post-antibiotic era, in which common infections and minor injuries, which have been treatable for decades, can once again kill (WHO, 2014). Antibiotic resistance complicates patients' recovery from even minor operations and is increasingly causing treatment failures. In fact, there are now strains of some genera of bacteria circulating globally which are resistant to all available antibiotics. Such strains commonly fall within the scope of the so-called ESKAPE pathogens—*Enterococcus faecium, Staphylococcus aureus, Klebsiella pneumoniae, Acinetobacter baumannii, Pseudomonas aeruginosa* and *Enterobacter* species (Boucher et al., 2009). The term ESKAPE pathogens was coined by Boucher et al., to emphasize that these bacteria currently cause a majority of hospital infections in the US and Europe and can effectively "escape" the majority, if not all, available antibiotics with panantibiotic-resistant infections now occurring. The death rate for patients with serious infections caused by common bacteria treated in hospitals is approximately twice that of patients with infections caused by the same non-resistant bacteria, e.g. people with methicillin-resistant *Staphylococcus aureus* (MRSA) infections are estimated to be 64% more likely to die than people with a non-resistant form of the infection (WHO, 2014). Of the Gram positive bacteria, methicillin resistant *S. aureus* continues to be a major cause of morbidity and mortality in hospitals in the US and Europe. However, in more recent years, several highly resistant Gram negative pathogens, including *Acinetobacter* species, multidrug resistant (MDR) *P. aeruginosa*, and carbapenem-resistant *Klebsiella* species and *Escherichia coli*, have emerged as major pathogens causing serious, and sometimes untreatable, infections. Advances in medicine mean that increasingly complex procedures take place: and these advances are leading to a growing number of elderly patients and patients undergoing surgery, transplantation, and chemotherapy all of which will produce an even greater number of immunocompromised individuals at risk of these infections (Walker et al., 2009). This phenomenon has led to a greater dependence on, and requirement for, effective antibiotics.

*P. aeruginosa* is one bacterium which is frequently multidrug resistant (MDR) having intrinsic resistance due to low permeability of its outer membrane limiting drugs getting into the cell, and a multitude of efflux pumps to expel any drugs that successfully manage to enter the cell. *P. aeruginosa* is also acquiring additional resistance mechanisms, including resistance to the "antibiotics of last resort" for Gram negatives, the carbapenems. *P. aeruginosa* causes approximately 10% of all hospital acquired infections and is the second leading cause of hospital-acquired pneumonia, which accounts for 50% of all hospital-acquired infection prescribing. *P. aeruginosa* infections in hospitals commonly require intravenous (IV) treatment with current standard of care for *P. aeruginosa* infections dictating that patients are treated with at least two antibiotics. Unfortunately, resistance frequently develops in patients during therapy. With so few new classes of antibiotic developed and approved for market within the last 30-40 years, there is a critical need for novel, safe and effective antibacterial agents.

As an alternative to conventional antibiotics, one family of proteins which demonstrate broad spectrum antibacterial activity inside bacteria comprises the α/β-type small acid-soluble spore proteins (known henceforth as SASP). Inside bacteria, SASP bind to the bacterial DNA: visualisation of this process, using cryoelectron microscopy, has shown that SspC, the most studied SASP, coats the DNA and forms protruding domains and modifies the DNA structure (Francesconi et al., 1988; Frenkiel-Krispin et al., 2004) from B-like (pitch 3.4 nm) towards A-like (3.18 nm; A-like DNA has a pitch of 2.8 nm). The protruding SspC motifs interact with adjacent DNA-SspC filaments packing the filaments into a tight assembly of nucleo-protein helices. In 2008, Lee et al. reported the crystal structure at 2.1 Å resolution of an α/β-type SASP bound to a 10-bp DNA duplex. In the complex, the α/β-type SASP adopt a helix-turn-helix motif, interact with DNA through minor groove contacts, bind to approximately 6 bp of DNA as a dimer and the DNA is in an A-B type conformation. In this way DNA replication is halted and, where bound, SASP prevent DNA transcription. SASP bind to DNA in a non-sequence specific manner (Nicholson et al., 1990) so that mutations in the bacterial DNA do not affect the binding of SASP. Sequences of α/β-type SASP may be found in appendix 1 of WO02/40678, including SASP-C from *Bacillus megaterium* which is the preferred α/β-type SASP.

WO02/40678 describes the use as an antimicrobial agent of bacteriophage modified to incorporate a SASP gene. In order to provide effective production of the modified bacteriophage in a bacterial host, WO02/40678 aims to avoid factors which may disrupt proliferation of the production host, such as expression of the SASP gene during production. To this end, the SASP gene was put under the control of an inducible promoter. In a preferred arrangement, at least one of the gene encoding products involved in the lytic process was inactivated.

WO2009019293 describes that effective production of bacteriophage may be achieved where the bacteriophage has been modified to delete a lysis gene and to carry a gene encoding a SASP under the control of a promoter which is controlled independently of the bacteriophage, and which is constitutive with no exogenous or in trans regulation necessary or provided. Such a modified bacteriophage is maintained as a prophage in a manufacturing host strain, and may be amplified by suitable induction methods to synthesise new phage within the manufacturing host strain. In this arrangement, the manufacturing host strain must be lysed by the addition of exogenous substances, e.g. lytic enzymes or chemicals, in order to release viable phage. An example of a suitable promoter is the fbaA promoter from *S. aureus* which is used to drive expression of the SASP-C gene from *Bacillus megaterium* and which, when present in multiple copies, for example following infection of target cells, drives toxic levels of SASP expression.

Bacteriophage vectors modified to contain a SASP gene have generally been named SASPject vectors. Once the SASP gene has been delivered to a target bacterium, SASP is produced inside those bacteria where it binds to bacterial DNA and changes the conformation of the DNA from B-like towards A-like. Production of sufficient SASP inside target bacterial cells causes a drop in viability of affected cells.

Bacteriophage have been used as medicines for the treatment of bacterial infections since the 1920s or 30s. Generally, bacteriophage are specific to their bacterial host. Some bacteriophage are temperate and others non-temperate. Temperate phage are able to infect the host cell and integrate into the host cell genome becoming a prophage which is generally harmless to the host cell in this state. Non-temperate or "lytic" phage are only able to replicate in a lytic lifestyle by making new bacteriophage progeny and ending in lysis of the host cell and release of mature phage particles. For useful medicines, the challenge is to provide bacteriophage compositions which can be used to treat infection from a variety of different bacteria in an effective way. It is commonly thought that this is achieved using the most potent bacteriophage compositions available: those with a broadened host range, possibly as a mixture or "cocktail" of bacteriophage (Carlton, 1999; Kutateladze and Adamia, 2010). Cocktails of wild type phage have been used to ensure sufficient spectrum of activity against clinical strains of bacteria (Burrowes and Harper, 2012). Such cocktails can consist of up to 20 different and unrelated phage (Abedon 2008). As an alternative to the cocktail approach, *E. coli* bacteriophage K1-5 has been isolated. This is a naturally-occurring obligately lytic phage which carries more than one host range determinant (HRD) allowing it to infect and replicate on both K1 and K5 strains of *E. coli* (Scholl et al, 2001). These phage are considered to be extra potent.

There remains a need to provide improved bacteriophage for use in treating bacterial infections in medicine as well as inhibiting or preventing bacterial cell growth in medical and non-medical situations.

SUMMARY OF THE INVENTION

In a first aspect, the present invention provides a modified bacteriophage capable of infecting a plurality of different target bacteria, which bacteriophage includes a toxin gene encoding a toxin protein which is toxic to the target bacteria; wherein the bacteriophage is lytic; and wherein the bacteriophage expresses host range determinant (HRD) proteins which have a plurality of bacterial host specificities. The bacterial host specificity of the HRD is advantageously within the same bacterial species.

It has surprisingly been found that a modified bacteriophage may be produced which is capable of infecting a variety of different target bacteria, and which is effective for use in medicine when engineered to carry a gene for a toxic protein. The modified bacteriophage is lethal to bacterial cells, and, despite being lytic, and thus requiring completion of the phage lifecycle to be released from cells, can be manufactured in a host cell through several rounds of infection and replication.

In one aspect, the HRD proteins which have a plurality of bacterial host specificities are hybrid HRD proteins each comprising an amino acid sequence from a plurality of different bacteriophages. Because the modified bacteriophage expresses a hybrid HRD protein this confers an enhanced host range on the phage. Bacteriophages according to the invention may be produced by genetic engineering, for example by selecting HRD from closely related phage. Having created such an extra-potent lytic phage, it can then be engineered to create a vector incorporating the toxin gene, which vector is capable of being manufactured in a host cell and effective as an antibacterial agent in vivo.

In another aspect, the HRD proteins expressed by the bacteriophage comprise a plurality of different HRDs, wherein each HRD has a different bacterial host specificity. In this aspect the HRDs can be homologous, heterologous, (hybrid) or a mixture of homologous and hybrid HRDs. The plurality of different HRDs confers upon the bacteriophage an enhanced host range. Such bacteriophage may be produced by genetic engineering, for example by selecting HRDs from phage which infect the same bacterial species. Having created such an extra-potent lytic phage, it can then be engineered to create a vector incorporating the toxin gene, which vector is capable of being manufactured in a host cell an effective as an antibacterial agent in vivo.

In a preferred arrangement, the toxin gene comprises an α/β small acid-soluble spore protein (SASP) gene encoding a SASP. In one aspect, the term 'SASP' as used in the specification refers to a protein with α/β-type SASP activity, that is, the ability to bind to DNA and modify its structure from its B-like form towards A-like form, and not only covers the proteins listed in appendix 1 of WO02/40678, but also any homologues thereof, as well as any other protein also having α/β-type SASP activity. In an alternative aspect, the term 'SASP' as used in the specification refers to any protein listed in appendix 1 of WO02/40678, or any homologue having at least 70%, 75%, 80%, 85%, 90%, 92%, 94%, 95%, 96%, 98% or 99% sequence identity with any one of the proteins. listed in appendix 1 of WO02/40678. In another alternative aspect, the term SASP' as used in the specification refers to any protein listed in appendix 1 of WO02/40678.

The SASP gene may be chosen from any one of the genes encoding the SASP disclosed in Appendix 1 of WO02/40678. In a preferred arrangement the SASP is SASP-C. The SASP-C may be from *Bacillus megaterium*.

It is preferred that the SASP gene is under the control of a constitutive promoter which is advantageously sufficiently strong to drive production of toxic levels of SASP when the modified bacteria phage is present in multiple copies in the target bacterium. Useful constitutive promoters include pdhA for pyruvate dehydrogenase E1 component alpha sub units, rpsB for the 30S ribosomal protein S2, pgi for glucose-6-phosphate isomerase and the fructose bisphosphate aldolase gene promoterfda. Preferred regulated promoters, active during infection, are lasB for elastase. These promoters are typically from *P. aeruginosa*. Promoters having a sequence showing at least 90% sequence identity to these promoter sequences may also be used.

The present invention is generally applicable to bacteriophage infecting a variety of different target bacteria. In one arrangement at least one of the target bacteria is *Pseudomonas*. Advantageously, the plurality of different target of bacteria is a plurality of different *Pseudomonas* bacteria. An important target is *Pseudomonas aeruginosa*.

It was previously considered that an obligate lytic phage would be unsuitable for use as a SASPject vector, since a requirement of a SASPject vector is that it is specifically not lytic for optimal therapeutic use. A non-lytic vector allows an increased time window for SASP expression, thereby increasing the efficacy of the treatment. In addition, prevention of rapid lysis upon treatment in vivo, was considered advantageous because it would limit the potential release of antibiotic resistance genes and toxic cell wall components which can lead to a dangerous inflammatory response.

The approach described in the present invention is advantageous as compared to the phage cocktail approach described previously. Mixtures of modified bacteriophage, such as SASPject vectors, are identical in structure and genome sequence, other than carrying a different HRD or hybrid HRD. One advantage is that control of the manufacturing process for the mix of SASPjects will be straightforward, which is an important aspect of a pharmaceutical preparation: the process will be materially the same for phage modified to carry a heterologous HRD as they share identical or near-identical biophysical properties. Another advantage is that the in vivo characteristics of the SASPject vectors are likely to be similar, e.g. pharmacokinetics/pharmacodynamics, as each vector is structurally the same or similar.

In one aspect of the present invention it has been found that phage can be created which are extra-potent obligately-lytic bacteriophage carrying HRDs which have a plurality of bacterial host specificities. Surprisingly, such phage can be used to make enhanced SASPject vectors which retain a lytic phenotype, and remain effective in vivo, and such phage can be manufactured to an adequate titre in a bacterial host. WO02/40678 and WO2009019293 have taught the creation of SASPject vectors from bacteriophage which have been modified to remove one or more lysis genes, and which reside as prophage in a host cell. Such SASPject vectors are manufactured by prophage induction and the cells are lysed by the exogenous addition of lysis agents, e.g. cell wall degrading enzymes or chemicals such as chloroform. As such, the cells do not need to remain viable until the end of the phage lifecycle, as the final lysis step is not reliant upon the synthesis and accumulation in the host cell of the modified phage's own lysis proteins. Given the toxic nature of the SASP protein, and the extra-potent nature of the modified phage described in the present invention, it was not anticipated that such phage would be suitable for modification to create SASPjects which could be manufactured via an obligate lytic lifecycle, requiring the phage to complete its lytic lifecycle in order to create viable SASPject vectors. However, it has been found that such SASPject vectors are capable of replication in host cells to an adequate titre. This allows the manufacture of SASPject vectors in a quantity suitable for effective in vivo use. Advantageously, SASPject vectors based upon such modified obligate lytic phage are capable of replication at the site of infection. This means that the dose required for a lytic SASPject can be lower than that required for a non-lytic SASPject when used in vivo. Lytic SASPject vectors according to the invention may be considered more potent than their non-lytic counterparts.

Phage suitable for such modification may be isolated by screening for phage capable of infecting a chosen bacterial species. For instance, phage may be isolated which infect *Pseudomonas aeruginosa*, by screening environmental sources for phage which are able to form plaques on representative *P. aeruginosa* strains (Gill and Hyman, 2010). Isolated phage may have their whole genomes sequenced and annotated. HRDs may be tail fibre proteins, which are commonly found to be proteins responsible for the initial recognition/binding to the host bacterium, for instance in phage T4, T5 and T7 (Rakhuba et al., 2010). Alternatively other HRD may be baseplate proteins. Phage genomes may be searched for potential HRD sequences by assessing the homology of all proteins in the phage genome to known sequences, using BLAST searches.

According to the present invention it is preferred that each HRD has a broad host range. This may be defined as the ability to infect >50% of a diverse collection or clinical isolates, totalling at least 35, preferably at least 40, more preferably at least 44, and most preferably >50 in number. Such isolates should be from a range of geographical locations, including Europe, the Americas, and Asia, should carry a diverse range of antibiotic resistance phenotypes, including multi-drug resistant (MDR) strains, and should be from a diverse range of infection sites, such as strains cultured from blood, lung and skin infections. Such isolates can be obtained from public strain collections such as the American Type Culture Collection (ATCC) and the National Collection of Type Cultures (NCTC). Generally, each tail fibre protein comprises a C-terminal receptor binding region for binding to the target bacteria and an N-terminal region linking the C-terminal receptor binding region to the body of the bacteriophage. Each of the C-terminal and N-terminal regions may be from different bacteriophage. In one arrangement, the N-terminal region comprises amino acids 1 to 628 of the tail fibre protein and the C-terminal region comprises the amino acids 629 to 964 of the tail fibre protein.

The C-terminal region may have no more than 96% amino acid sequence identity with the C-terminal region of bacteriophage Phi33 and may be from any one of the bacteriophage Phi33, LBL3, SPM-1, F8, PB1, KPP12, LMA2, SN, 14-1, JG024, NH-4, PTP47, C36, PTP92 and PTP93. Lower amino acid sequence identities in the C-terminal region are preferred. Advantageously the sequence identity is less than 90%, more advantageously less than 80%, preferably less than 70%, more preferably less than 60%, still more preferably less than 50%, particularly preferably less than 40%, more particularly preferably less than 30%. The N-terminal region may have at least 90% and advantageously at least 95% amino acid sequence identity with the N-terminal region of bacteriophage Phi33 and may be from any one of bacteriophage Phi33, LBL3, SPM-1, F8, PB1, KPP12, LMA2, SN, 14-1, JG024, NH-4, PTP47, C36, PTP92 and PTP93. The N-terminal region and the C-terminal region may be from the same bacteriophage to provide a homologous tail fibre protein. Alternatively, the N-terminal region and the C-terminal region may be from different bacteriophage tail fibre proteins to provide a heterologous tail fibre protein. In one arrangement where the phage tail fibre protein is homologous, each tail fibre protein is from a bacteriophage selected from Phi33, LBL3, SPM-1, F8, PB1, KPP12, LMA2, SN, 14-1, JG024, NH-4, PTP47, C36, PTP92 and PTP93.

It is advantageous to identify phage tail fibre proteins which share sequence identity of greater than 90% in the N-terminal region. For example several phage—Phi33, PTP47, PTP92 and C36—with a broad host range for *P.*

*aeruginosa* strains (all of these phage infect >60%, when analysed against 260 strains), have been isolated/identified and their genomes sequenced. Analysis of the genome sequences of Phi33, PTP47, PTP92 and C36 reveals that they contain genes encoding putative tail fibre proteins with a high level of sequence identity in the N-terminal region (>95% amino acid sequence identity), following a 2 sequence BLAST alignment, compared to the Phi33 tail fibre amino acids 1-628 (amino acid identity in parentheses): C36 (96%), PTP47 (98%), PTP92 (97%). BLAST searches have shown that these 4 phages are related to 10 other deposited phage genome sequences which, together, form the family of PB1-like phage: PB1, SPM1, F8, LBL3, KPP12, LMA2, SN, JG024, NH-4, 14-1 (Ceyssens et al., 2009). The homology of these putative tail fibre proteins was assessed. Following a 2 sequence BLAST alignment, compared to the Phi33 tail fibre protein (amino acid identity in parentheses): LBL3 (96%), SPM-1 (95%), F8 (95%), PB1 (95%), KPP12 (94%), LMA2 (94%), SN (87%), 14-1 (86%), JG024 (83%), NH-4 (83%), C36 (96%), PTP47 (86%), PTP92 (83%). An alignment of all 14 of the aforementioned phage tail fibre proteins is shown in FIG. 13.

Analysis of the annotated tail fibre protein sequences from these 14 phages reveals that the N-terminal region of the proteins—equivalent to Phi33 tail fibre amino acids 1-628—show an even higher level of sequence identity at the amino acid level than the sequence identity of these proteins over their entire length, in the range of 96-100% for all 14 proteins. Following a 2 sequence BLAST alignment, compared to the N-terminal amino acids 1-628 of the Phi33 tail fibre protein (amino acid identity in parentheses): LBL3 (96%), SPM-1 (96%), F8 (96%), PB1 (96%), KPP12 (98%), LMA2 (99%), SN (99%), 14-1 (97%), JG024 (97%), NH-4 (97%), PTP47 (98%), C36 (96%), PTP92 (97%). However, the C-terminal region of the protein—equivalent to Phi33 tail fibre amino acids 629-964—is not as conserved as the N-terminal region in some of the proteins, the range of sequence identity being typically 57-96%. Following a 2 sequence BLAST alignment, compared to the C-terminal 629-964 amino acids of the Phi33 tail fibre protein (amino acid identity in parentheses): LBL3 (94%), SPM-1 (93%), F8 (93%), PB1 (94%), KPP12 (87%), LMA2 (85%), SN (65%), 14-1 (65%), JG024 (57%), NH-4 (57%), PTP47 (64%), C36 (96%), PTP92 (57%). Analysis of phage tail fibres from other, well characterised, phage has shown that they possess an N-terminal tail base plate binding region and a C-terminal receptor binding region (Veesler and Cambillau, 2011). In experimental analysis of their bacterial strain host range, using plaque assay or growth inhibition tests, the phage Phi33, PTP47, PTP92 and C36 have overlapping but non-identical host range (Table 1). Taken together with the established evidence for the role of the C-terminal region of phage tail fibres being involved in bacterial host receptor binding, and the sequence variation in the C-terminal region of these 4 phage, and their similar but non-identical host range, it is postulated that the C-terminal variation is associated with host range in the phage assessed.

It is further provided, according to this invention, that the genes for a homologous tail fibre protein can be taken from one phage and added to another, replacing the resident tail fibre, based upon their high level of sequence identity in the N-terminal region. The N-terminal region is thought to be involved in the binding of the tail fibre to the phage tail (Veesler and Cambillau, 2011), allowing the formation of viable phage with the host range associated with donor phage's tail fibre. Hybrid tail fibre genes may be made, carrying the conserved N-terminal tail attachment region of the tail fibre from a recipient phage, together with the variable C-terminal receptor-binding region from a homologous donor phage tail fibre protein, using tail fibres genes such as those described herein. Such tail fibre hybrid genes could be used to replace the tail fibres of the phage. This provides an N-terminal region of the hybrid tail fibre (from the recipient phage) and allows the formation of viable phage with the host range associated with donor phage's tail fibre C-terminal receptor-binding region. Transplantation of engineered tail fibre hybrid genes into a recipient phage has been demonstrated in the present invention. Using standard molecular genetic techniques, Phi33 has been modified to carry heterologous tail fibre hybrids from the following phage: PTP92, PTP47, LBL3, SPM-1, F8, PB1, KPP12, LMA2, SN, 14-1, NH-4. All modified phage have been shown to be viable and able to plaque on *P. aeruginosa*. (The nomenclature of tail fibre hybrids is as follows: As an example, a hybrid gene such that the N-terminal tail attachment region of Phi33 is hybridised with the C-terminal receptor binding region of PTP47 is Phi33(N)PTP47(C).)

In one such modified phage, Phi33 was engineered such that its tail fibre gene carries the C-terminal receptor binding region of PTP92, creating PTP93 (Phi33(N)PTP92(C)). This was assessed in more detail, by testing the host range against 35 diverse *P. aeruginosa* clinical isolates. Comparing host range of the progenitor phage (Phi33), the tail fibre donor (PTP92) and the hybrid phage (PTP93), the host range of the PTP93 hybrid phage is equivalent to that of the tail fibre donor phage (PTP92) rather than Phi33, but it was surprisingly found that in some instances PTP93 possesses the host range of Phi33 on strains that PTP92 cannot infect, thus PTP93 inherits the host range of both phages (Table 2). PTP93 possesses a broader host range (92%) than either Phi33 (74%) or PTP92 (66%) (Table 2). PTP93 is an example of an obligately lytic bacteriophage which can be considered as "extra-potent" as it possesses a characteristic above and beyond those exhibited in their unmodified state. Such extra potent phage are suitable for further modification to make SASPject vectors.

Phi33, through assessment of sequence homology by one skilled in the art, can be placed in the group of PB1-like phage (Ceyssens et al., 2009), and may be considered a broad host range phage by the definition given earlier. Such a phage could be isolated by the methods described earlier. Phi33 is suitable for genetic modification to introduce a gene for SASP under the control of a promoter. Such a modified phage would be suitable for use in treating infections caused by susceptible *P. aeruginosa* bacteria, either on its own or in combination with other modified bacteriophage. In one arrangement, the invention may not extend to an isolated bacteriophage PTPX31 or PTPX32.

A preferred approach according to the present invention is to use one or more obligately lytic phage, each engineered to carry a SASP gene expressed from a constitutive promoter, each phage being genetically identical other than their tail fibre or tail fibre hybrid gene. Preferred obligately lytic phage for modification and for provision of tail fibre genes to create tail fibre genes or tail fibre hybrid genes are phages carrying tail fibre genes which encode predicted proteins that possess ≥90% amino acid sequence identity in their N-terminal regions compared to N-terminal regions of the tail fibre of other isolated or identified phage.

Another preferred approach according to the present invention is to use one or more obligately lytic phage engineered to express 2 or more HRDs (extra potent obligately lytic phage), each engineered to carry a SASP gene expressed from a constitutive promoter, each phage being genetically identical other than carrying different tail fibre genes, or tail fibre hybrid genes, Preferred obligately lytic phages for modification and for provision of tail fibre genes to create phages carrying multiple tail fibre genes or tail fibre hybrid genes are phages carrying tail fibre genes which encode predicted proteins that possess ≥90% amino acid sequence identity in their N-terminal regions compared to N-terminal regions of the tail fibre of other isolated or identified phage.

Preferred obligate lytic phage meeting these criteria are Phi33, PTP92, PTP47, LBL3, SPM-1, F8, PB1, KPP12, LMA2, SN, 14-1, NH-4, PTP93, JG024, PTP47 and C36. Such phage can be identified by a simple PCR assay, by subjecting plaques of isolated phage to PCR with primers specific to highly conserved regions in the N-terminal region of the tail genes. In such a way, suitable phage can be identified without whole genome sequencing. Phage PB1 can be obtained from a public strain collection. Phages need not be isolated or provided in order to generate tail fibre sequences as such sequences may be identified in DNA sequence databases, or other sources of DNA sequences, which may provide the information necessary in order to synthesise and clone, by standard methods, such sequences, or to create hybrid tail fibre sequences.

Particularly preferred phage for modification are PTP93, Phi33, PTP92, PTP47 and C36. Particularly preferred extra-potent obligate lytic phage are: Phi33, modified to carry the tail fibre hybrid Phi33(N)PTP92(C) in place of the resident tail fibre; Phi33 modified to carry the tail fibre hybrid Phi33(N)PTP47(C) in place of the resident tail fibre. In one aspect of the present invention, preferred extra-potent non-lytic SASPject derivatives of Phi33 include: Phi33, modified to carry the tail fibre hybrid Phi33(N)PTP92(C) in place of the resident tail fibre and carrying SASP-C from *Bacillus megaterium*, codon-optimised for expression in *P. aeruginosa*, under the control of the *P. aeruginosa* fructose bisphosphate aldolase (fda) gene promoter; Phi33 modified to carry the tail fibre hybrid Phi33(N)PTP47(C) in place of the resident tail fibre and carrying SASP-C from *Bacillus megaterium*, codon-optimised for expression in *P. aeruginosa*, under the control of the *P. aeruginosa* fructose bisphosphate aldolase (fda) gene; Phi33 modified to carry SASP-C from *Bacillus megaterium*, codon-optimised for expression in *P. aeruginosa*, under the control of the *P. aeruginosa* fructose bisphosphate aldolase (fda) gene promoter. In a particularly preferred aspect the present invention provides a mixture of SASPject comprising or consisting of the 3 aforementioned SASPjects formulated together.

A mixture of three modified bacteriophage, designated PT3.9, was constructed and its efficacy in killing *P. aeruginosa* tested. The mixture consists of: Phi33 carrying the Phi33(N)PTP92(C) tail fibre, modified to carry the fda-SASP-C(*P. aeruginosa* codon optimised sequence) (PTP388); Phi33 carrying the Phi33(N)PTP47(C) tail fibre, modified to carry thefda-SASP-C (*P. aeruginosa* codon optimised sequence) (PTP389); Phi33 carrying the Phi33 (N)Phi33(C) tail fibre, modified to carry the fda-SASP-C(*P. aeruginosa* codon optimised sequence) (PTP387).

Figure 14:
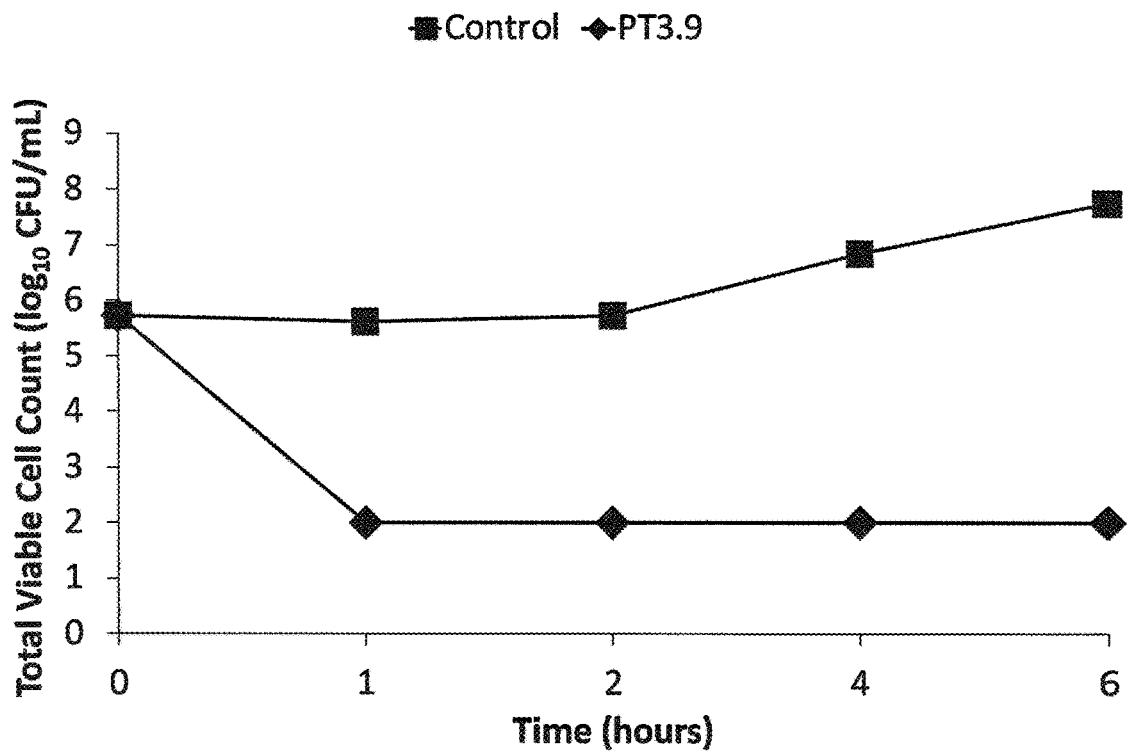
Figure 14:
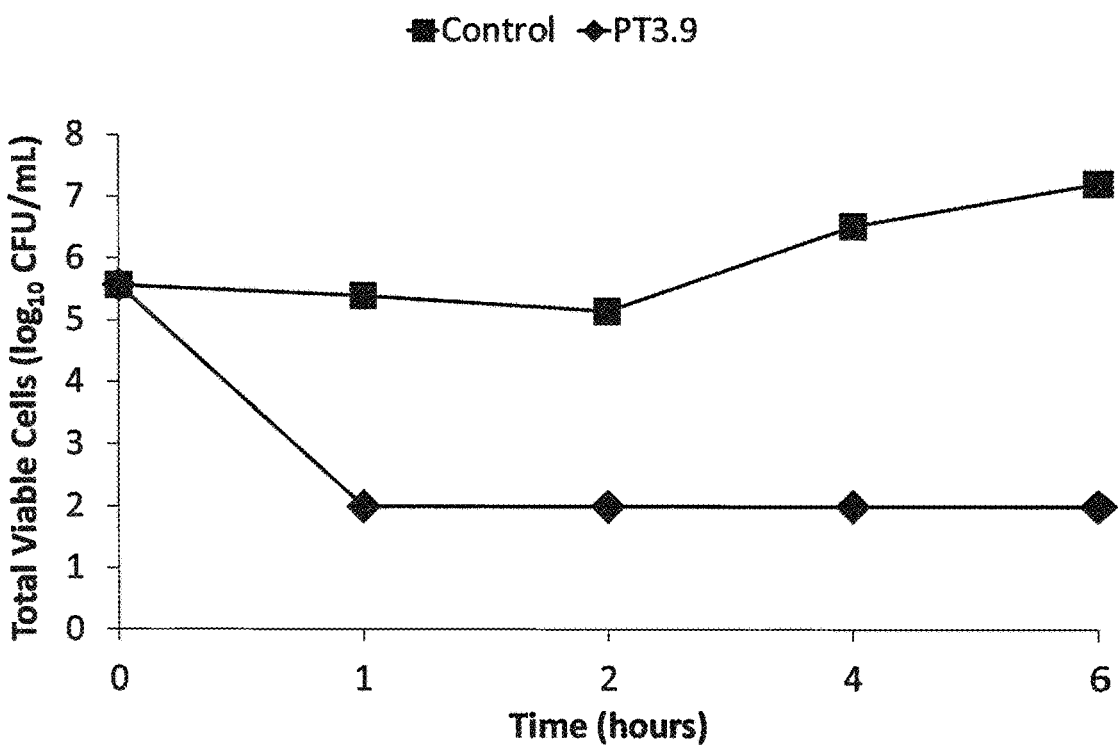

The efficacy of PT3.9 was tested in a 6 hour time-kill curve experiment against a multi-drug resistant (MDR) clinical isolate (trachea isolation site, antibiotic resistance to ceftazidime, piperacillin-tazobactam and imipenem) of *P. aeruginosa*, strain 3503 and reference strain ATCC 27853. Briefly, cultures were set up in Luria Bertani (LB) broth supplemented with 5 mM calcium chloride, 5 mM magnesium sulphate and 0.1% glucose (LC broth), and grown at 37° C. $5 \times 10^5$ colony forming units per millilitre (cfu/ml) of *P. aeruginosa* was incubated with $3 \times 10^9$ plaque forming units per ml (pfu/ml) of PT3.9, or extra LC broth as a control (untreated culture). Samples were removed at 0, 1, 2, 4, and 6 hours for serial dilution and plating on LC agar plates and then overnight incubation at 32° C. For both strains, the viable cell count was reduced from $5 \times 10^5$ cfu/ml to below the limit of detection ($10^2$ cfu/ml) within 1 hour of treatment, and no viable cells were detected after 6 hours (FIG. 14). In contrast, the untreated control culture grew to between $5 \times 10^8$ and $1 \times 10^9$ cfu/ml for both strains. This demonstrates the ability of PT3.9 to kill clinical strains of *P. aeruginosa*.

Figure 15:
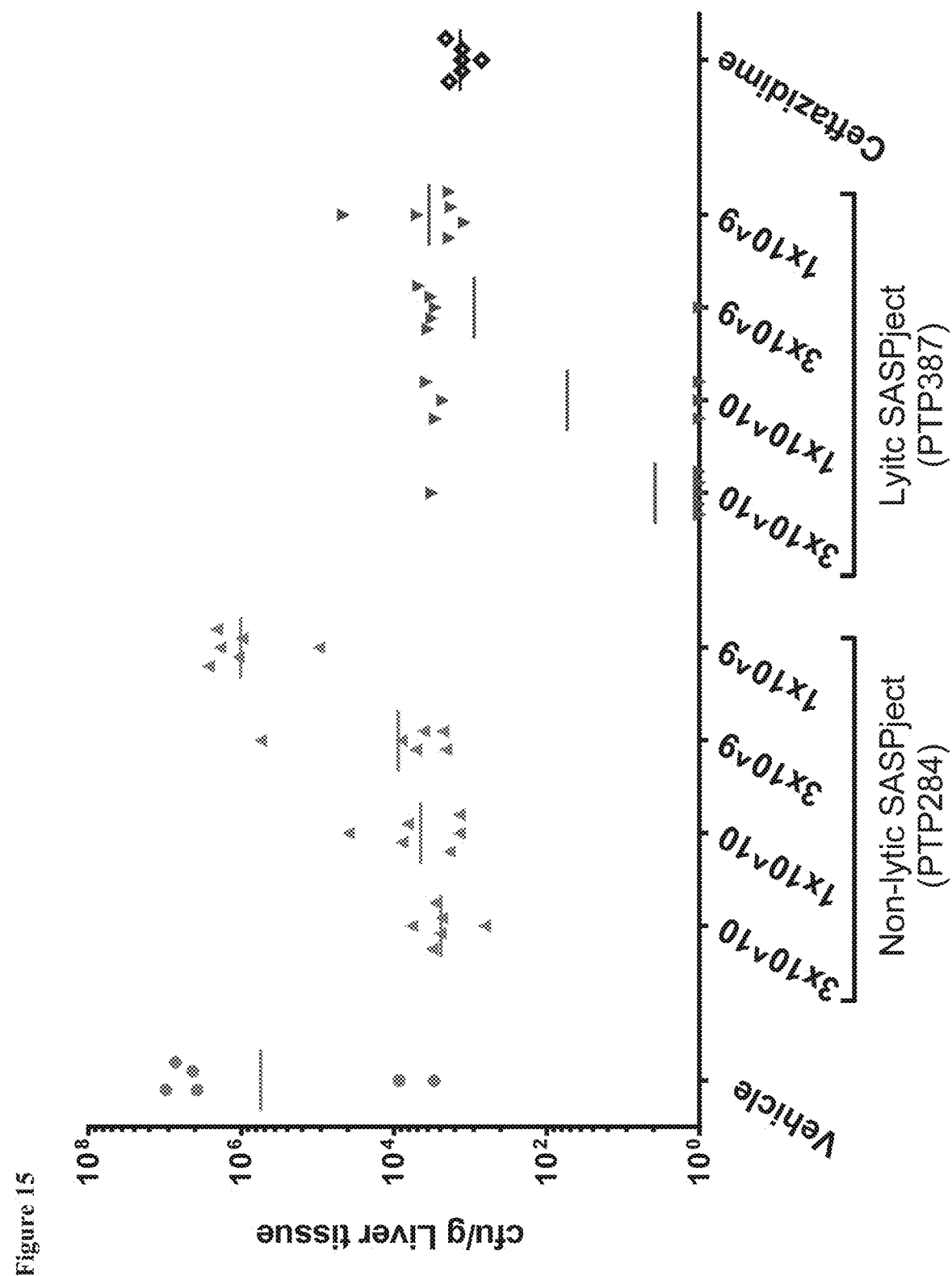

PTP387, a component SASPject of PT3.9, was tested in vivo in comparison to PTP284, a SASPject which is equivalent to PTP387 other than lacking one of the lysis genes (endolysin). An immunocompetent murine model of *P. aeruginosa* bacteraemia was used to assess the potency of the two SASPject vectors. Briefly, animals were infected by intravenous injection with an incoculum of 7.5 $\log_{10}$ cfu of *P. aeruginosa* strain ATCC 27853. At 2 hours post infection, the mice were treated either with PTP284, PTP387, vehicle (buffer), or ceftazidime (50 mg/kg) by intravenous injection. PTP284 and PTP387 were administered at the following doses: $3 \times 10^{10}$, $1 \times 10^{10}$, $3 \times 10^9$, and $1 \times 10^9$ pfu. At 22 hours post treatment, mice were euthanised by carbon dioxide asphyxiation, and the livers were removed and weighed. Liver tissue was homogenised in tryptone soya broth (TSB) and the number of viable cells in the liver tissue was enumerated by serial dilution and plating on Cetrimide agar plates. A control (not treated) group of mice was euthanised at 2 hours post infection and the viable cells in the liver tissue enumerated, to assess the viable cell count in the lung tissue at the time of treatment. A dose response was seen for both PTP284 and PTP387, when assessing the geometric mean of the bioburden levels of *P. aeruginosa* in liver tissue (FIG. 15). The potency of PTP387 was greater than that of PTP284 when assessing the log reduction in cfu/g liver tissue compared to the level assessed at the time of treatment: 22 hours post treatment, PTP387 caused a 3-log reduction in liver tissue bioburden at a $1 \times 10^9$ pfu dose, whilst an equivalent effect of PTP284 was seen at $1 \times 10^{10}$ pfu. PTP387 caused a greater maximum effect on liver tissue bioburden reduction compared to PTP284: at a dose of $3 \times 10^{10}$ pfu, PTP387 caused a 5.4-log reduction in liver tissue bioburden at 22 hours post treatment, whilst PTP284 caused a 2.4-log reduction. This demonstrates the increased potency of the lytic SASPject in vivo when compared to equivalent non-lytic SASPject.

The mixture of lytic modified SASPject phage comprising PT3.9 was tested in vivo in comparison to the mixture of non-lyitc modified SASPject phage comprising PT3.8. The modified phage in PT3.8 are identical to those in PT3.9 other than lacking the lysis gene (endolysin) present in PT3.9. A neutropenic murine model of *P. aeruginosa* pneumonia was used to assess the potency of the two mixtures of SASPject phage. Briefly, animals were rendered neutropenic by immunosuppression with cyclophosphamide 200 mg/kg 4 days before infection and 150 mg/kg 1 day before infection by intraperitoneal injection. Animals were anaesthetised and infected intranasally with $4.5 \times 10^3$ cfu of *P. aeruginosa* strain ATCC 27853. Groups of 6 mice were given each treatment. PT3.8 and PT3.9 were administered via the trachea 15 minutes post infection in an aerosolised form at the following doses: $1 \times 10^9$, $3 \times 10^9$, $1 \times 10^{10}$ and $1.5 \times 10^{10}$ pfu. Tobramycin (200 μg) was administered in an aerosolised form to a control group of mice, and another group was treated with placebo buffer. Animals were euthanised 24 hours post treatment and lung tissue was removed and homogenised in phosphate buffered saline (PBS). The tissue homogenate was serially diluted and plated on agar plates to enumerate the bacteria in the lung tissue. A control (not treated) group of mice was euthanised at 15 minutes post infection and the viable cells in the lung tissue enumerated, to assess the viable cell count in the tissue at the time of treatment. A dose response was seen for both PT3.8 and PT3.9, when assessing the geometric mean of the bioburden levels of *P. aeruginosa* in lung tissue (FIG. 16). The potency of PT3.9 was greater than that of PT3.8. When assessing the log reduction in cfu/g lung tissue compared to the level assessed at the time of treatment: 24 hours post treatment, PT3.9 caused a >2-log reduction in lung tissue bioburden at a $1\times10^9$ pfu dose, whilst an equivalent effect of PT3.8 was seen at doses between $1\times10^{10}$ and $1.5\times10^{10}$ pfu. Thus PT3.9 was more than 10 times more potent than PT3.8.

The ability of PTP387 to propagate in a host cell and yield bacterial lysates suitable for further purification was assessed in comparison to the unmodified phage (Phi33). Briefly, overnight culture of *P. aeruginosa* strain 1868 were used to inoculate 2 X 1 L bioreactor vessels, each containing 0.5 L of rich broth medium, to an OD600 of 0.05. The cultures were grown to OD600=0.3-0.4 and then infected with phage Phi33 or PTP387 to a final concentration of $1\times10^7$ pfu/ml, and grown further at 37° C. After 5 hours of growth, the cultures were treated with benzonase and sterile filtered. The concentration of each phage was determined by plaque assay. The lysate titres yielded for PTP387 were comparable to those obtained for Phi33: $2\times10^{11}$ pfu/ml (PTP387) and $5\times10^{11}$ pfu/ml (Phi33). The titre of PTP387 increased by 4-logs over 5 hours, demonstrating the ability of this phage to complete several cycles of infection, multiplication and lysis, despite the presence of the toxic SASP gene.

Fermentations were performed at 15.5-16 L scale for all 3 of the modified phage which comprise PT3.9. Briefly, overnight cultures of *Pseudomonas aeruginosa* were used to inoculate a 16 L bioreactor containing 15.5 to 16 L of rich broth medium, to an OD600 of 0.05. Each culture was grown to OD600=0.4-0.7 before being infected with either PTP387, PTP388 or PTP389 (SASPject phage which comprise PT3.9) to a final concentration of $1\times10^7$ pfu/ml. Cultures were grown for another 5 hours before Benonzase treatment. Samples were removed, sterile filtered, and analysed by plaque assay. Two fermentations were performed for each SASPject phage. All 3 of the modified SASPject phage comprising PT3.9 were able to propagate to $5\times10^{11}$ to $1\times10^{12}$ pfu/ml. Thus all 3 of the modified SASPject phage are able to complete several cycles of infection, multiplication and lysis, despite the presence of the toxic SASP gene.

The quantities of PTP387 obtained by such manufacturing processes at 1 L scale are suitable for effective in vivo use, as demonstrated by the use of such preparations in murine infection models (FIGS. 15 and 16). The levels of PT387, PTP388 and PTP389 obtained by such manufacturing processes at 15.5-16 L scale are suitable for effective in vivo use, as demonstrated by the use of such preparations, when combined as a mixture (PT3.9), in murine infection models (FIGS. 15 and 16).

In another embodiment, an obligately lytic phage may be modified to create a SASPject by inserting a SASP gene under the control of a constitutive promoter, and the tail fibre gene could be deleted altogether. Such phage must be propagated in a strain in which a tail fibre gene or tail fibre hybrid gene is expressed in trans. In such an instance, the SASPject progeny from such a strain would carry a single tail fibre, derived from the propagation strain, yet would lack in their genomes any tail fibre or tail fibre hybrid gene(s). Several such propagation strains could be constructed and the same tail fibre deleted SASPject expressed in each. In this way several different SASPject derivatives could be made, each carrying a different tail fibre or tail fibre hybrid protein. These SASPjects could be used to formulate a mixture.

In another embodiment, an obligately-lytic phage engineered to carry a SASP gene expressed from a constitutive promoter may be propagated in a host strain carrying the gene(s) for hybrid tail fibre protein(s) in trans under the control of a suitable promoter. Suitable promoters for the tail fibre hydrid gene(s) may be a phage promoter, particularly the promoter which drives expression of the tail fibre gene in the engineered, obligately-lytic phage. Other suitable promoters are inducible promoters, such as lac, and trp, together with their cognate regulatory proteins. The SASPject progeny obtained from such strains are extra-potent, carrying the tail fibre hybrid(s) expressed from the strain in trans as well as their own. Alternatively, the tail fibre gene from the obligately lytic phage may be deleted altogether, providing that a strain is used for propagation in which tail fibre gene(s) or tail fibre hybrid gene(s) are expressed in trans, allowing for the formation of derivative SASPjects. In such an instance, the SASPject progeny from such a strain would carry multiple tail fibres, yet would lack in their genomes any tail fibre or tail fibre hybrid gene(s).

In a further aspect, the present invention provides a composition for inhibiting or preventing bacterial cell growth, which comprises a modified bacteriophage or mixtures thereof as defined herein and a carrier therefor. The modified bacteriophage may be provided in admixture with at least one other modified bacteriophage which is capable of infecting target bacteria, which includes a toxin gene such as a SASP gene encoding a SASP which is toxic to the target bacteria. Then at least one other modified bacteriophage may or may not express a plurality of different HRDs. Such compositions may have a wide range of uses and are therefore to be formulated according to the intended use. The composition may be formulated as a medicament, especially for human treatment and may treat various conditions, including bacterial infections. Among those infections treatable according to the present invention are localised tissue and organ infections, or multi-organ infections, including blood-stream infections, topical infections, oral infections including dental carries, respiratory infections and eye infections. The carrier may be a pharmaceutically-acceptable excipient or diluent. The exact nature and quantities of the components of such compositions may be determined empirically and will depend in part upon the routes of administration of the composition.

Routes of administration to recipients include intravenous, intra-arterial, oral, buccal, sublingual, intranasal, by inhalation, topical (including ophthalmic), intra-muscular, subcutaneous, intra-vaginal, intrathecal and intra-articular. For convenience of use, dosages according to the invention will depend on the site and type of infection to be treated or prevented. Respiratory infections may be treated by inhalation administration and eye infections may be treated using eye drops. Oral hygiene products containing the modified bacteriophage are also provided; a mouthwash or toothpaste may be used which contains modified bacteriophage according to the invention formulated to eliminate bacteria associated with dental plaque formation.

A modified bacteriophage, or mixture thereof, according to the invention may be used as a bacterial decontaminant, for example in the treatment of surface bacterial contamination as well as land remediation or water treatment. The bacteriophage may be used in the treatment of medical personnel and/or patients as a decontaminating agent, for example in a handwash. Treatment of work surfaces and equipment is also provided, especially that used in hospital procedures or in food preparation. One particular embodiment comprises a composition formulated for topical use for preventing, eliminating or reducing carriage of bacteria and contamination from one individual to another. This is important to limit the transmission of microbial infections, particularly in a hospital environment where bacteria resistant to conventional antibiotics are prevalent. For such a use the modified bacteriophage may be contained in Tris buffered saline or phosphate buffered saline or may be formulated within a gel or cream. For multiple use a preservative may be added. Alternatively the product may be lyophilised and excipients, for example a sugar such as sucrose, may be added.

DETAILED DESCRIPTION OF THE INVENTION

Figure 1B:
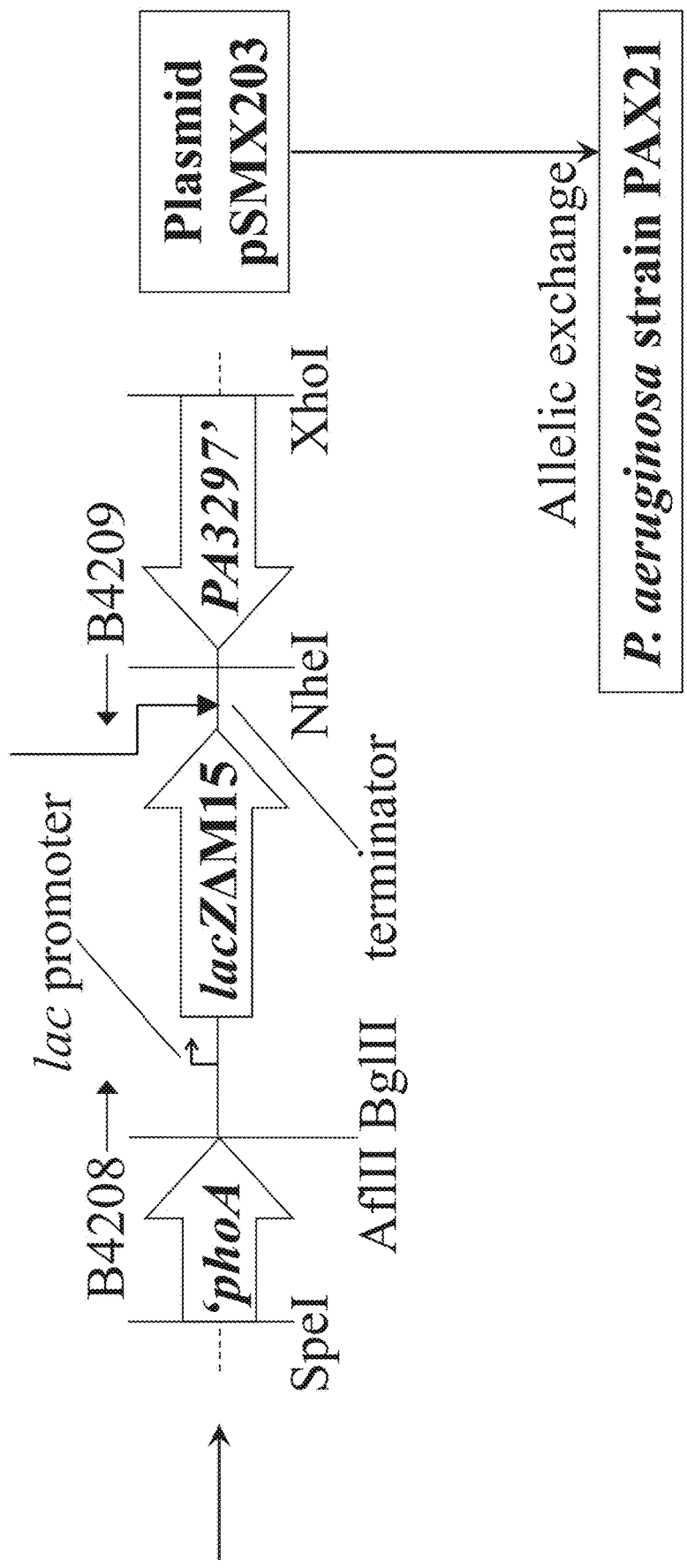
Figure 2A:
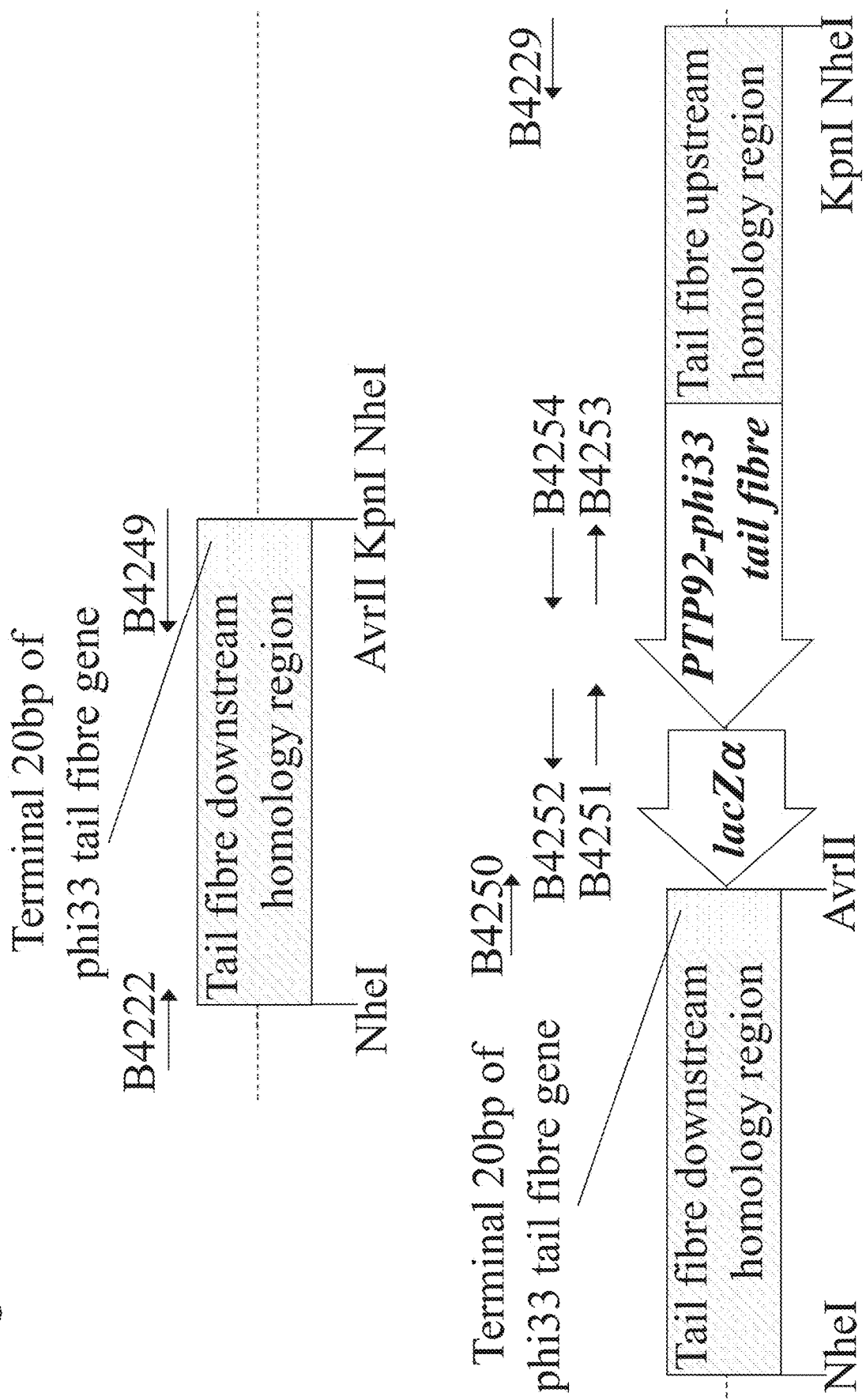
Figure 2B:
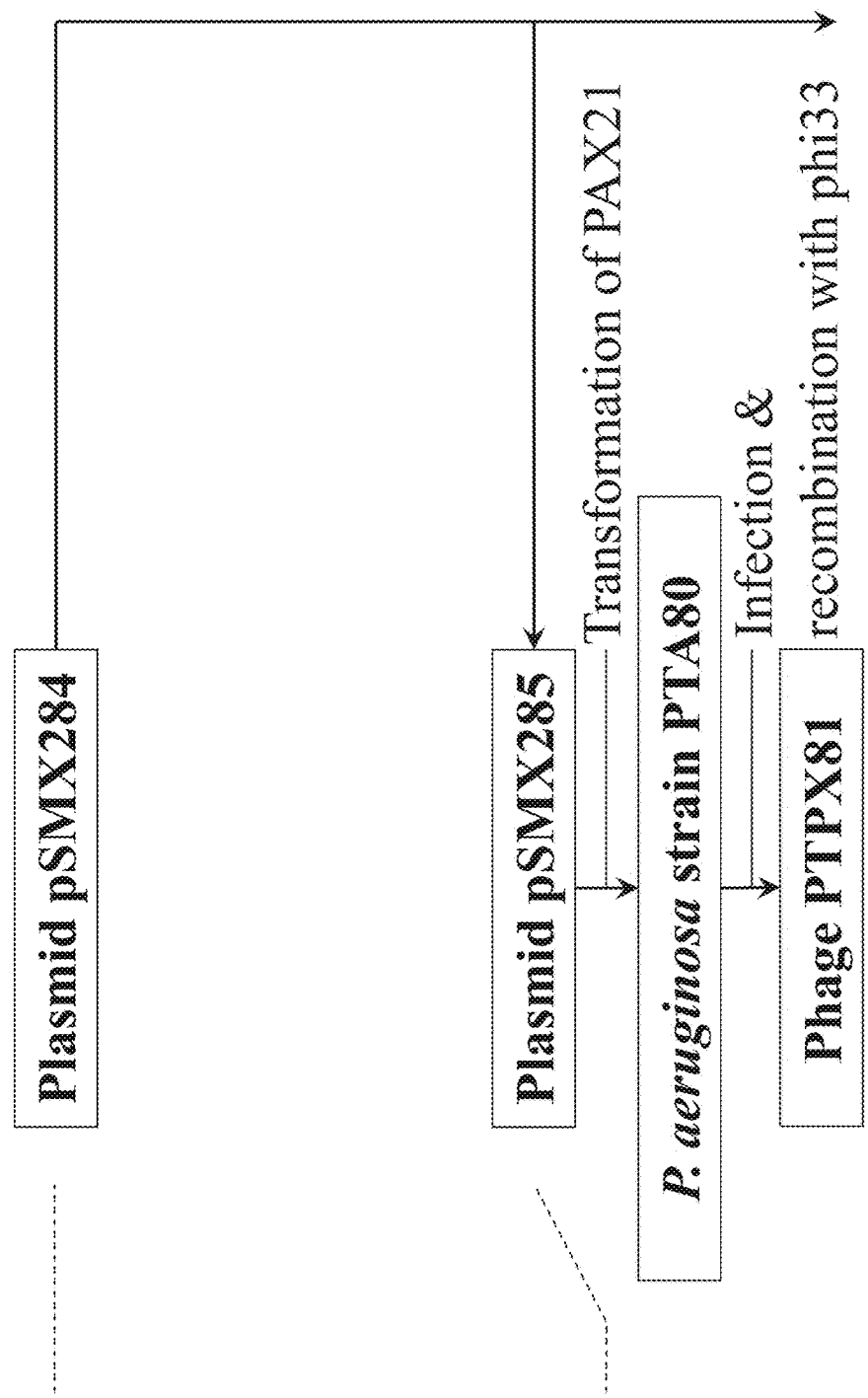
Figure 2C:
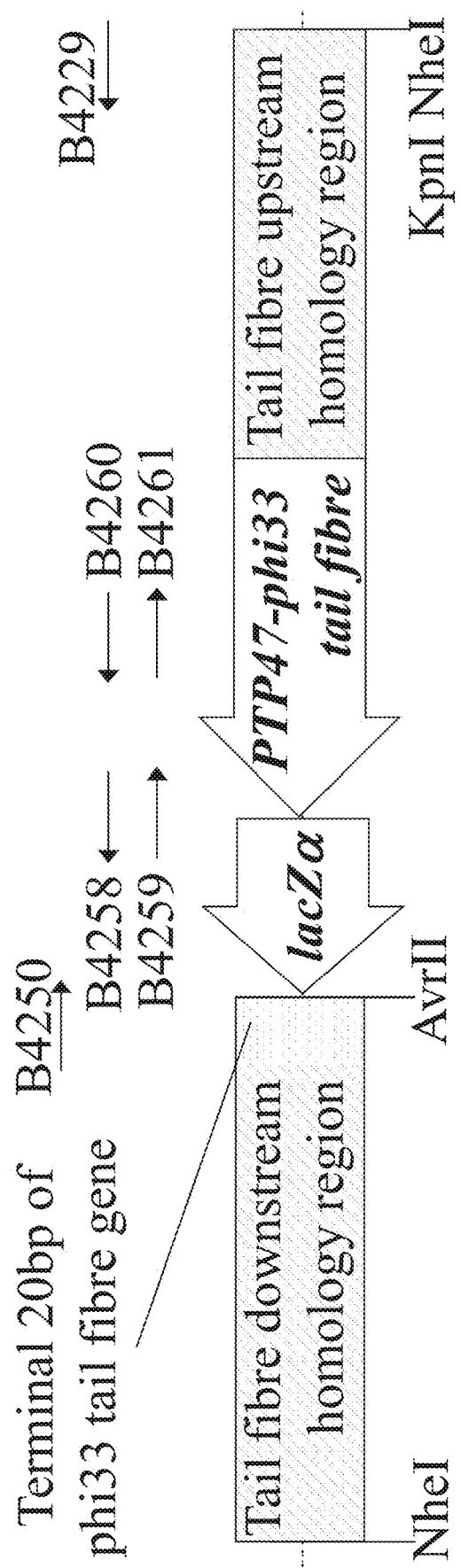
Figure 2D:
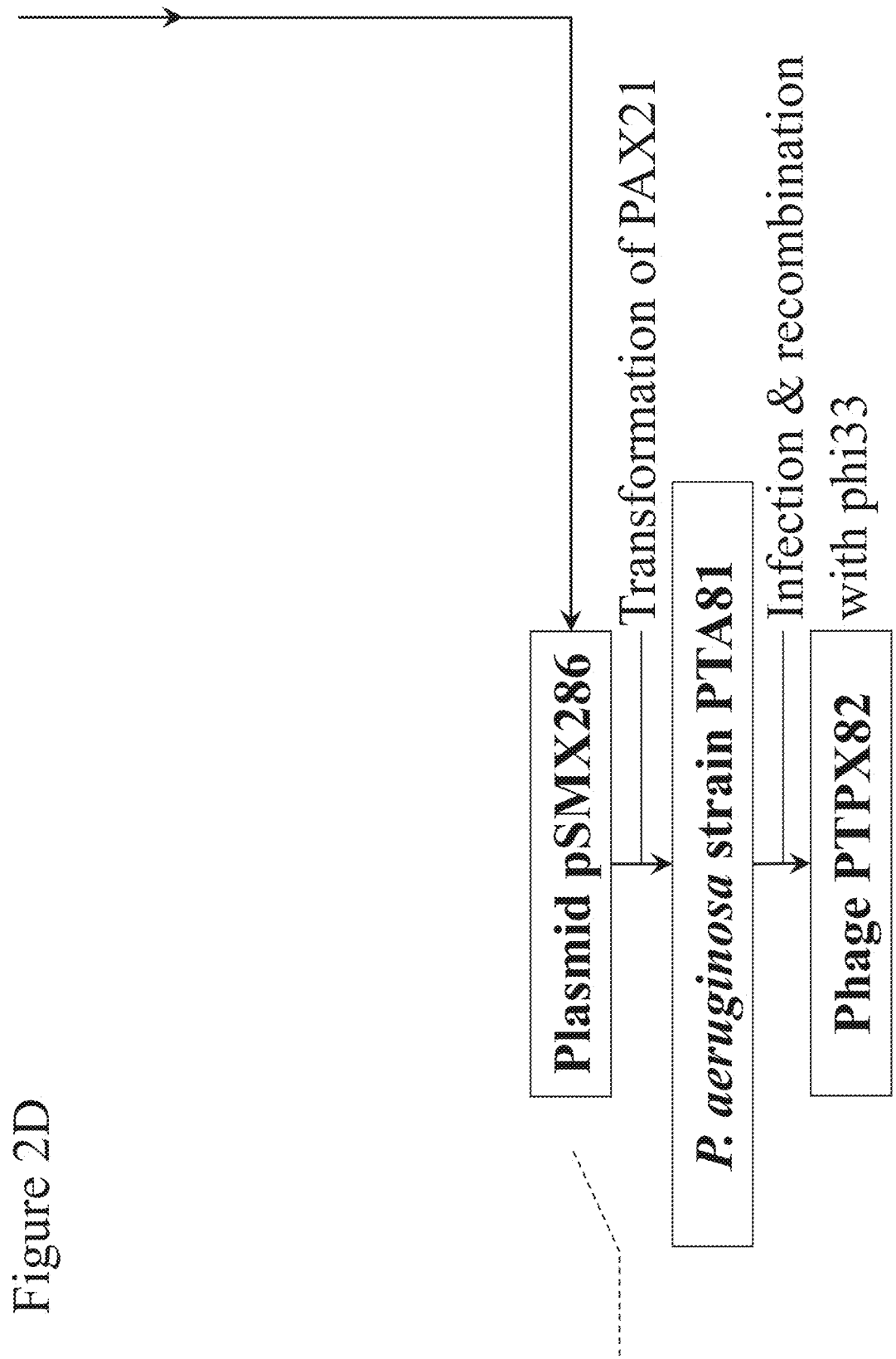
Figure 3A:
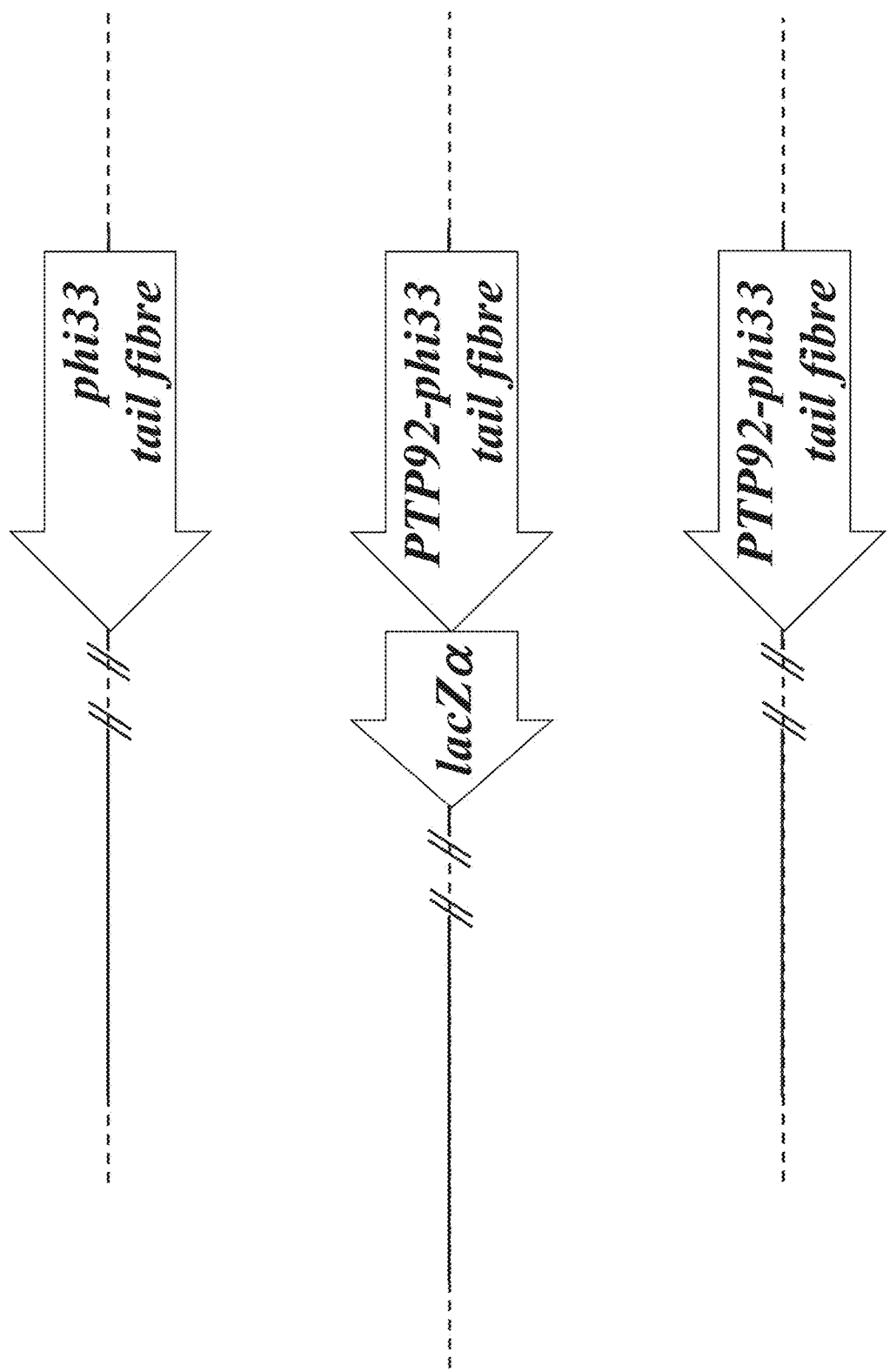
Figure 3B:
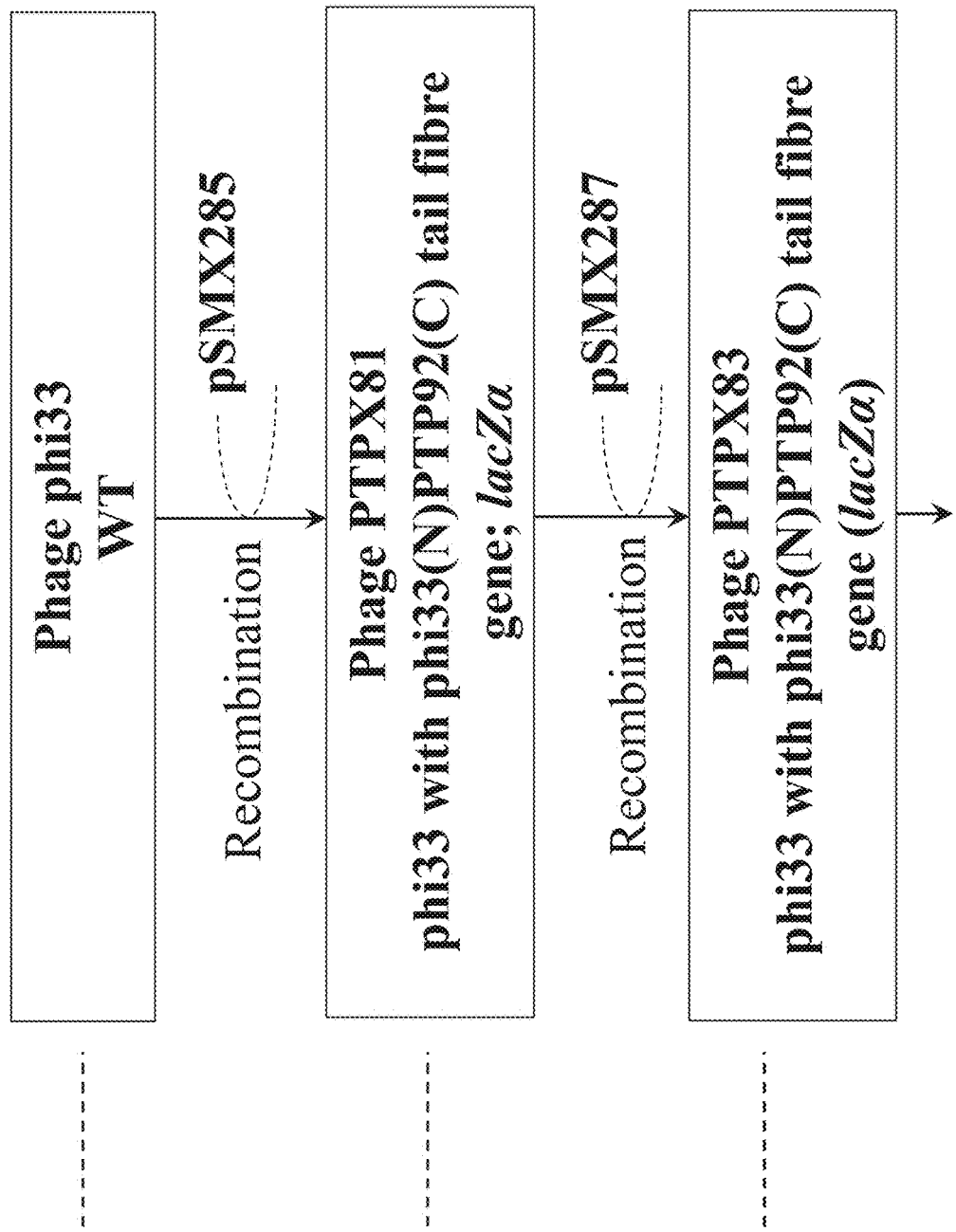
Figure 3C:
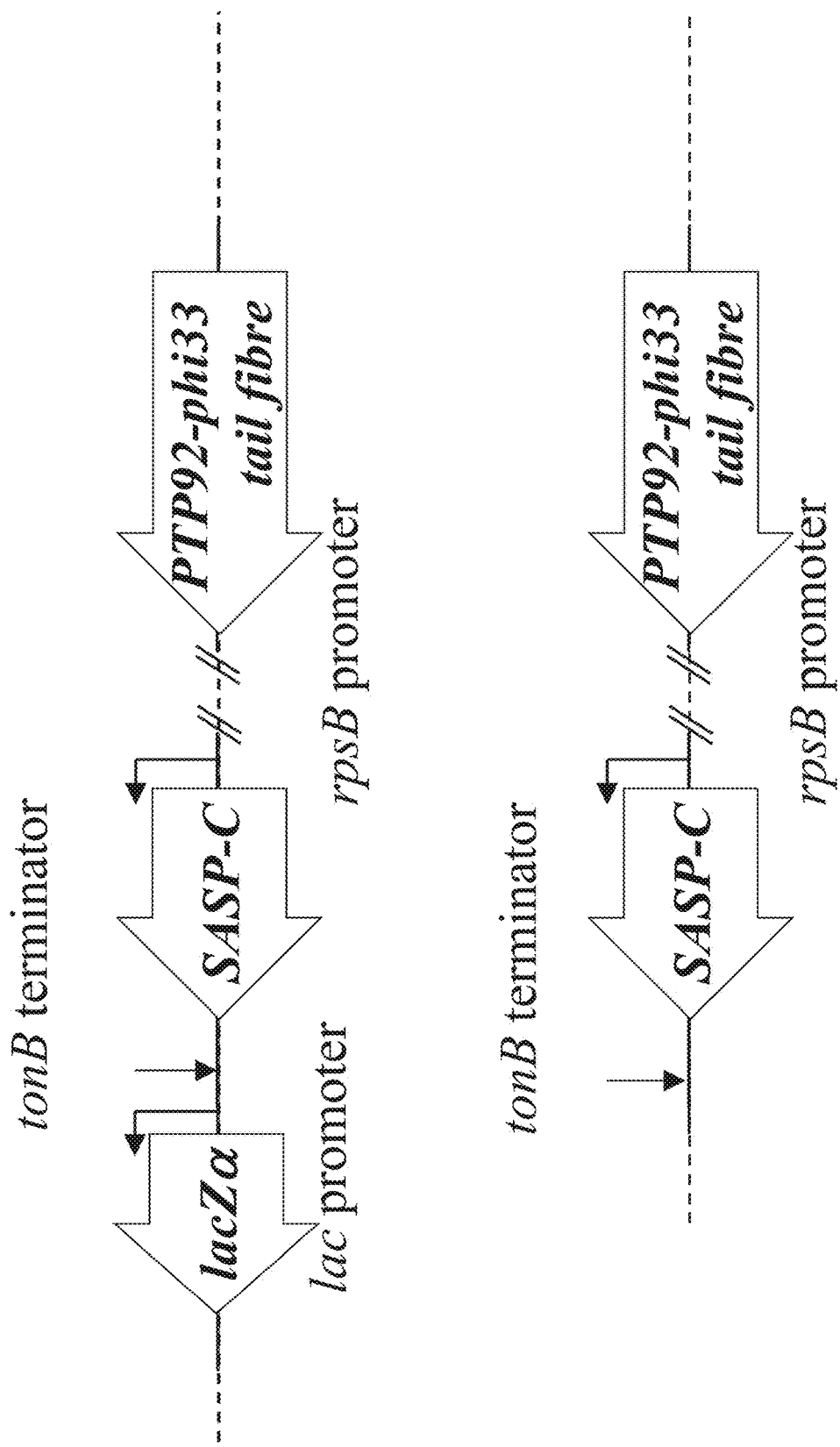
Figure 3D:
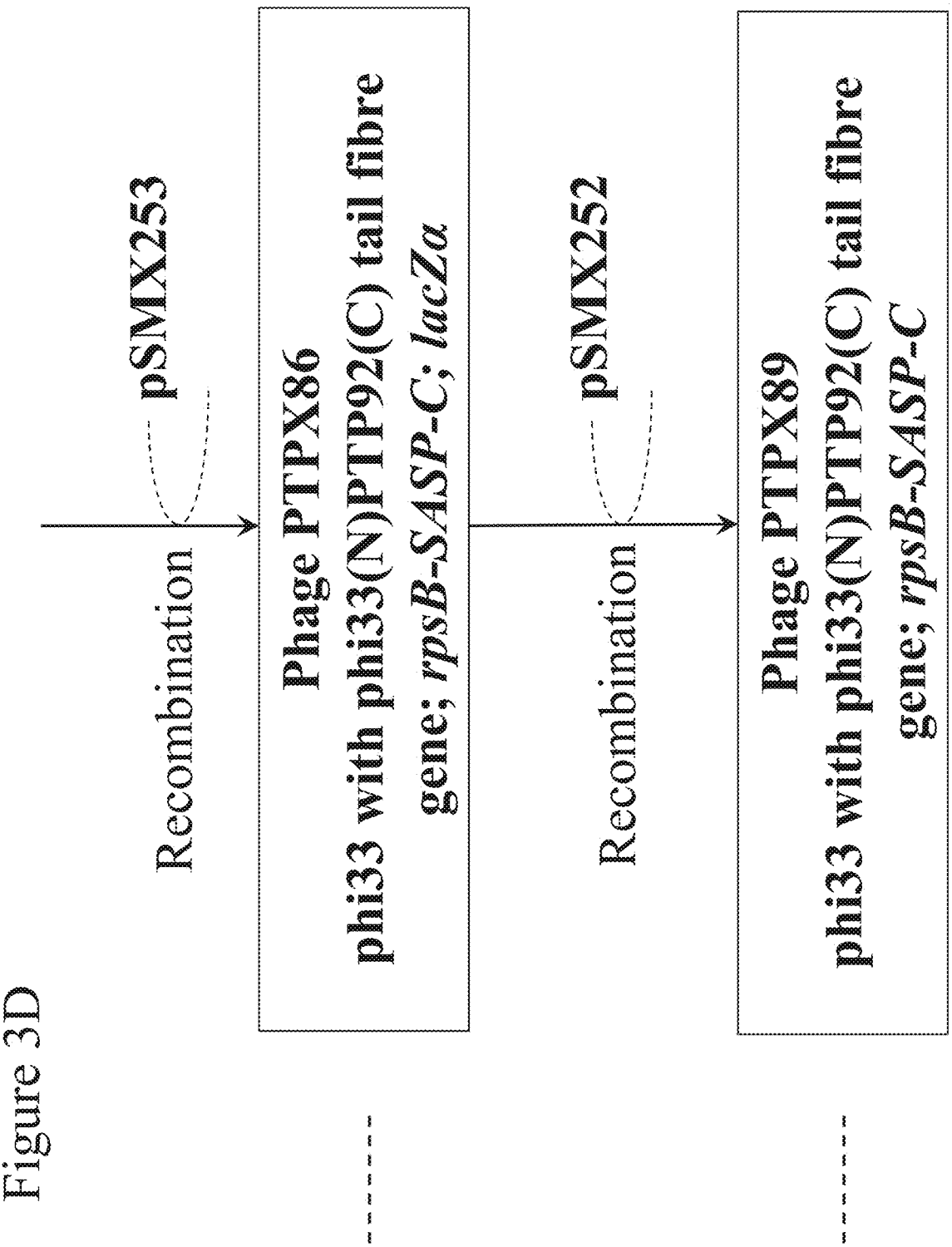
Figure 4A:
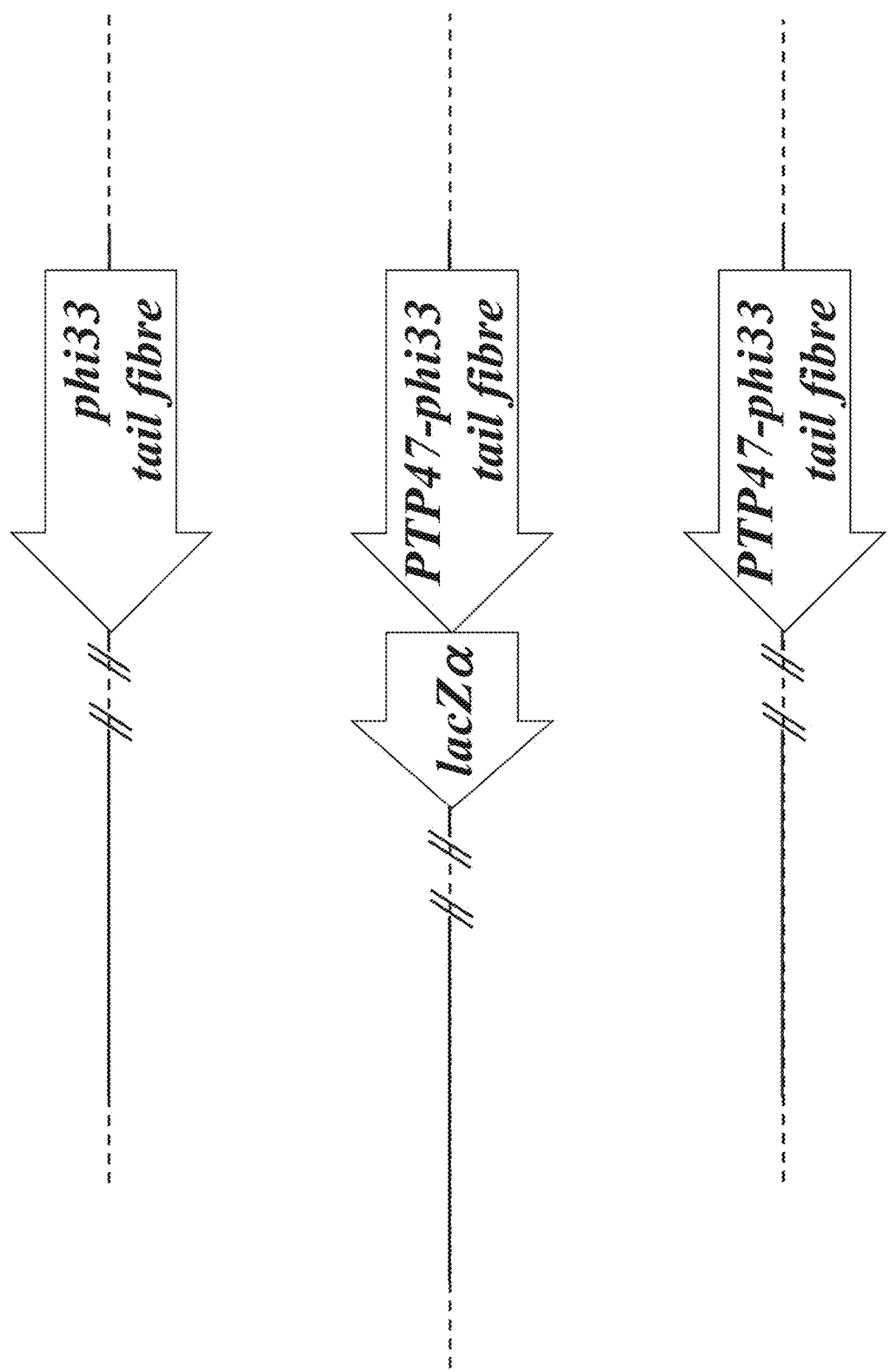
Figure 4B:
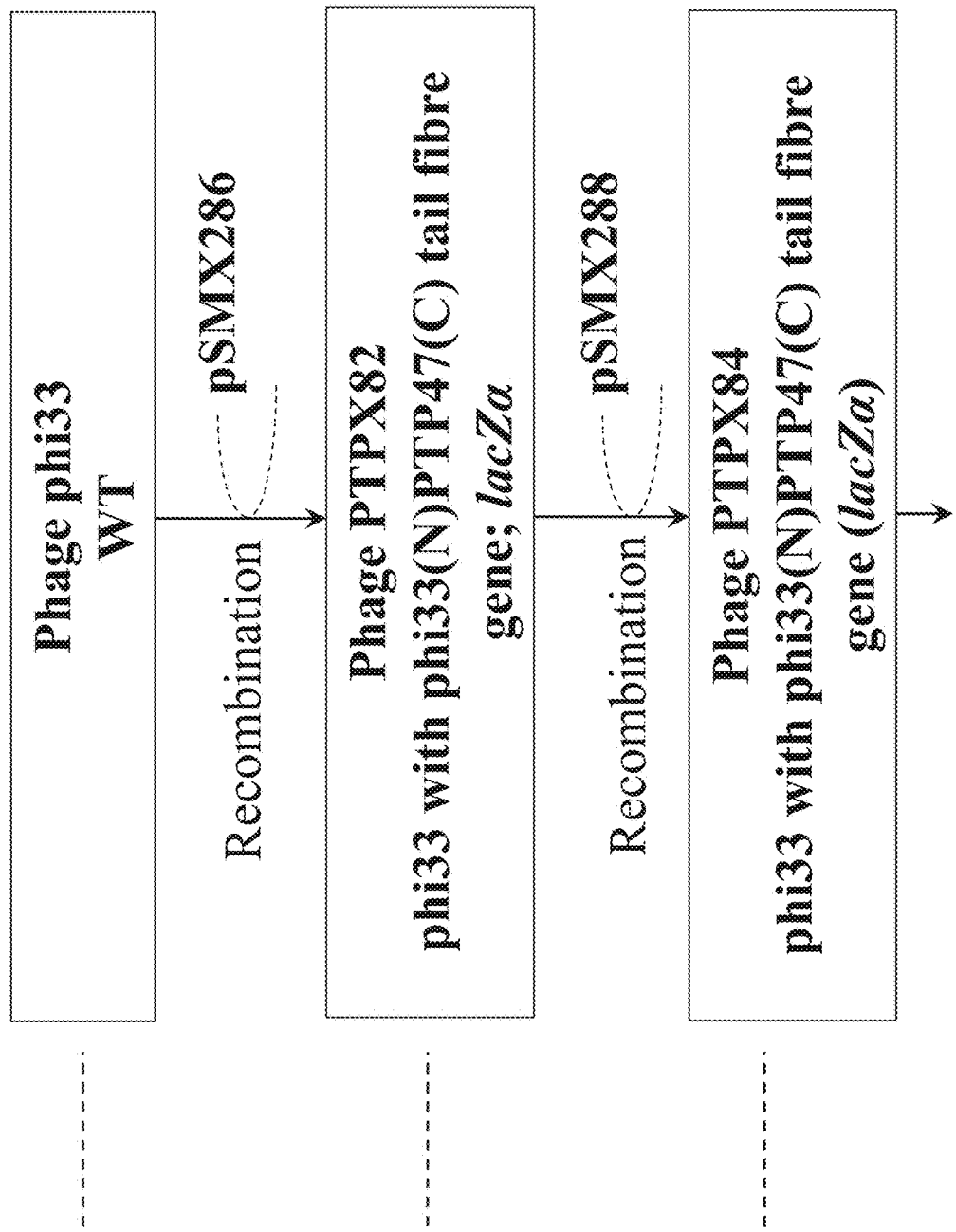
Figure 4C:
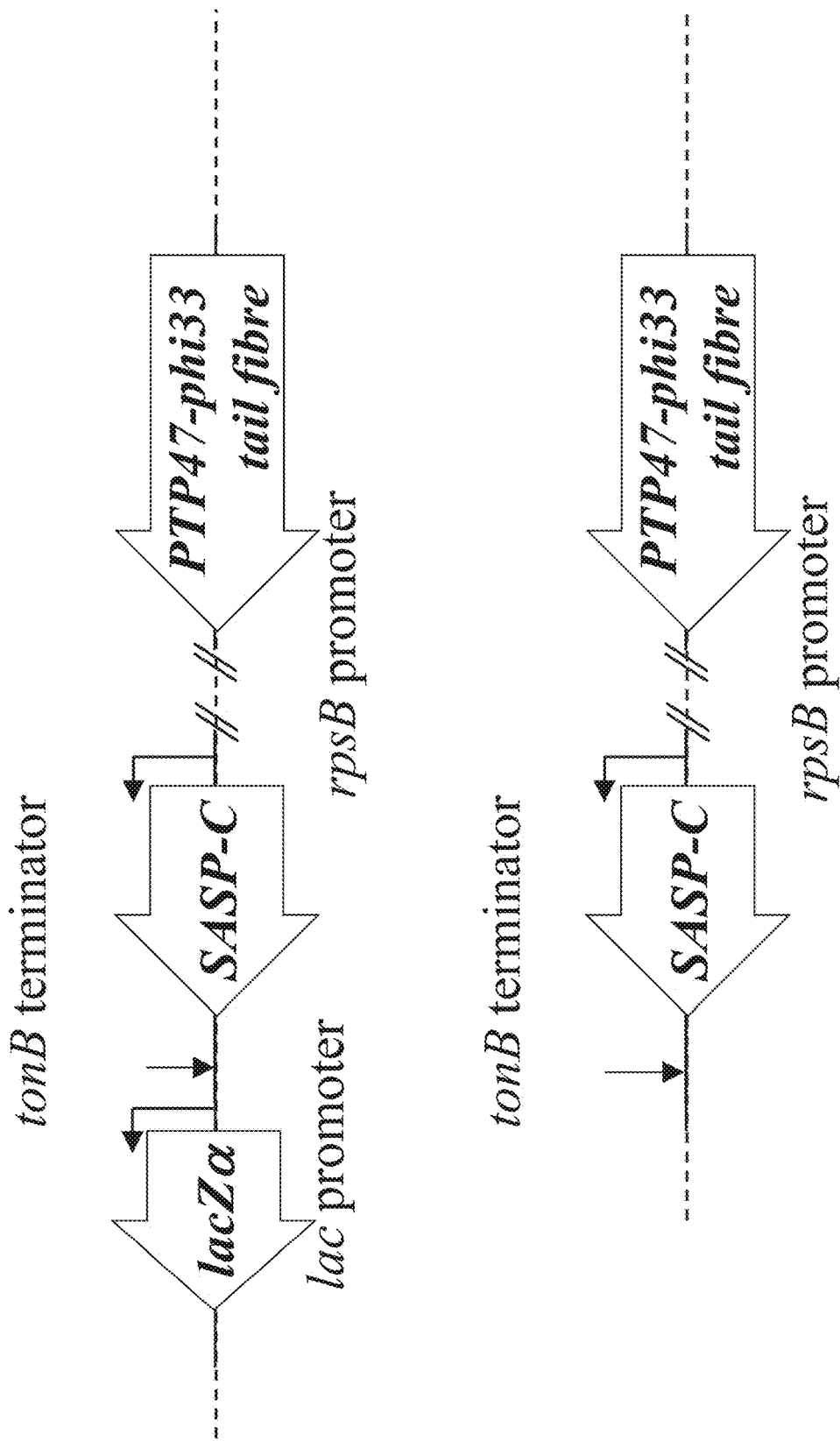
Figure 4D:

This invention will now be described in more detail, by way of example only, and with reference to the accompanying drawings, in which:

FIGS. 1A and 1B are a schematic diagram showing construction of a plasmid containing lacZΔM15

Figure 5A:
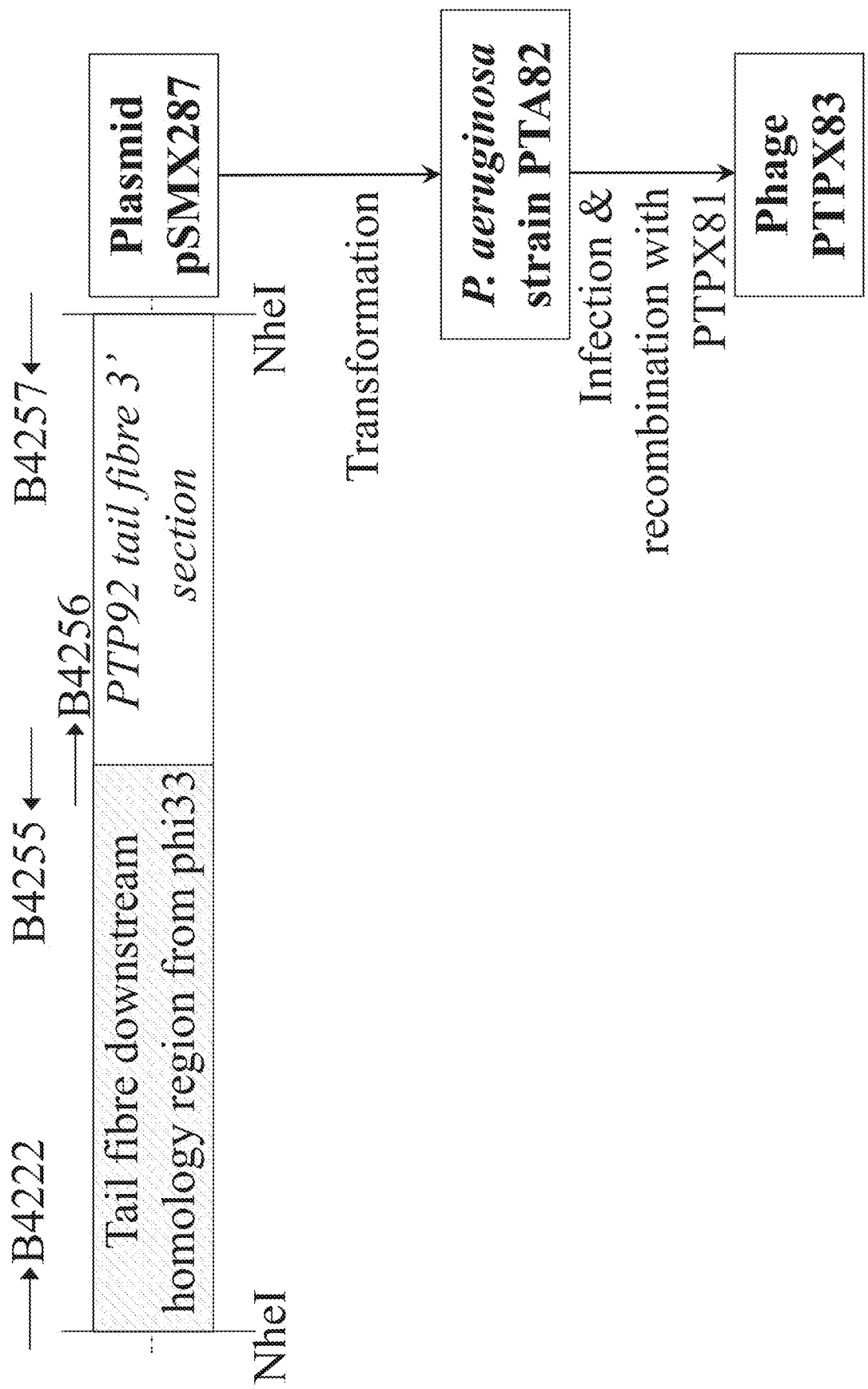
Figure 5B:
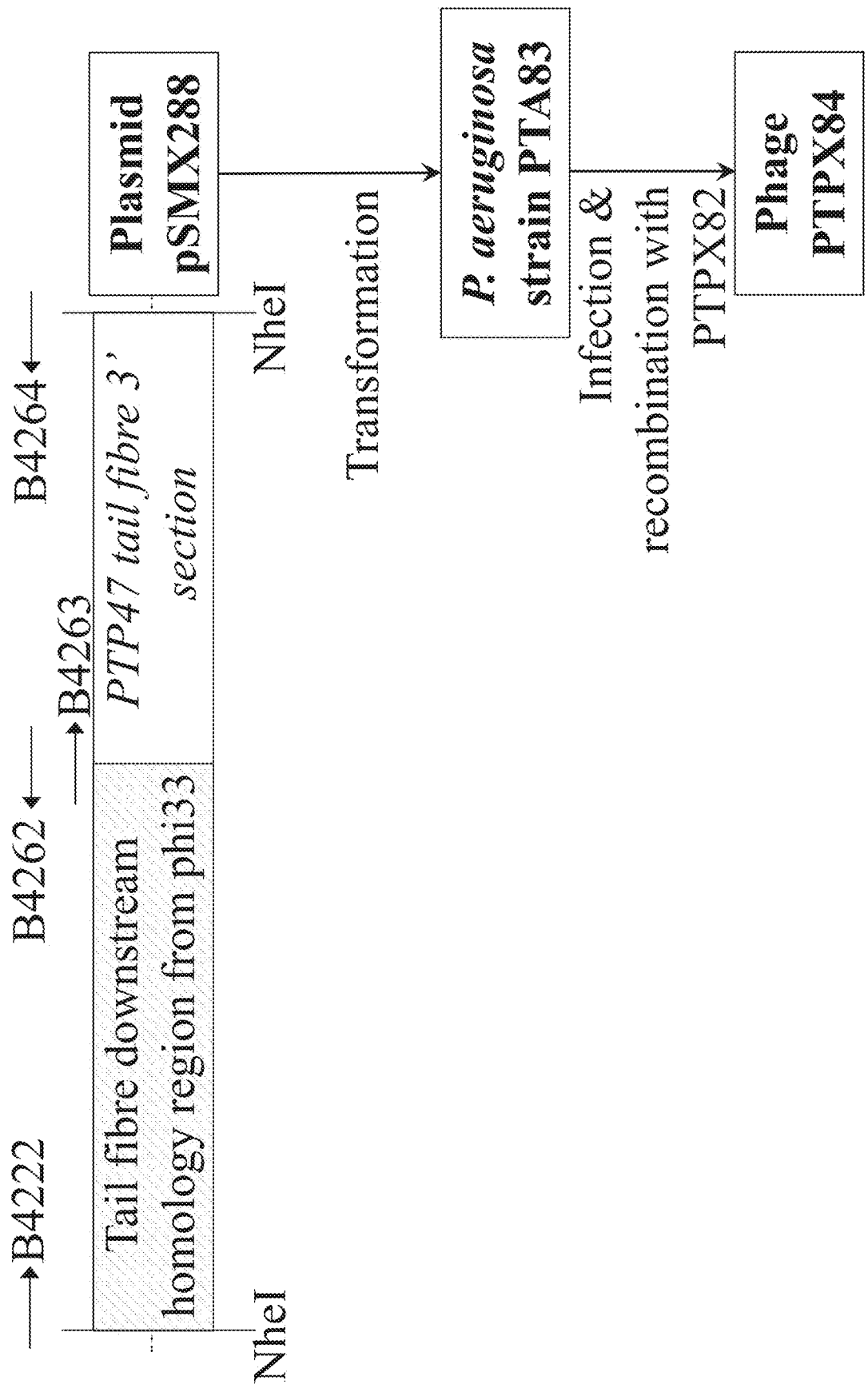
Figure 6A:
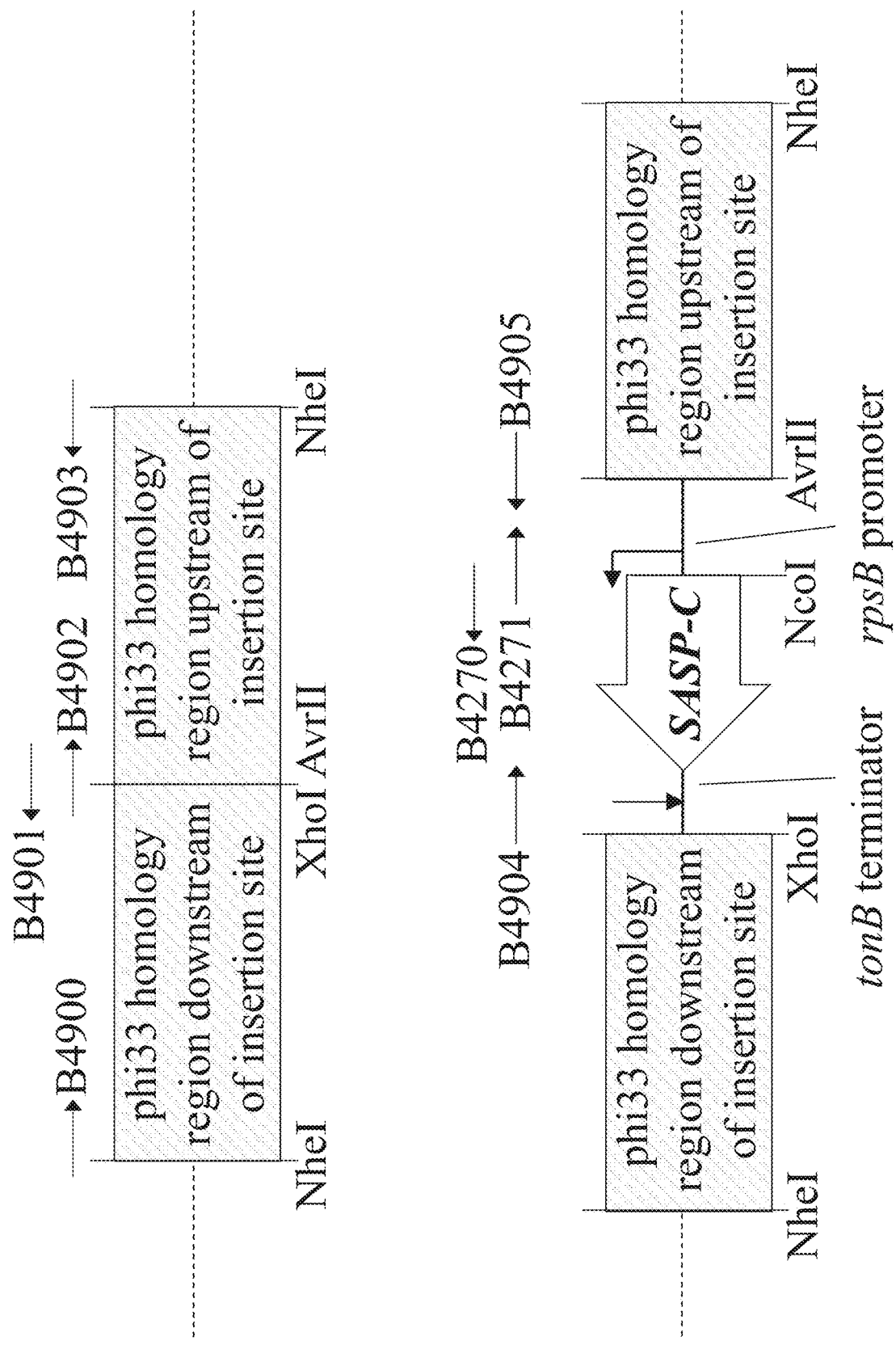
Figure 6B:
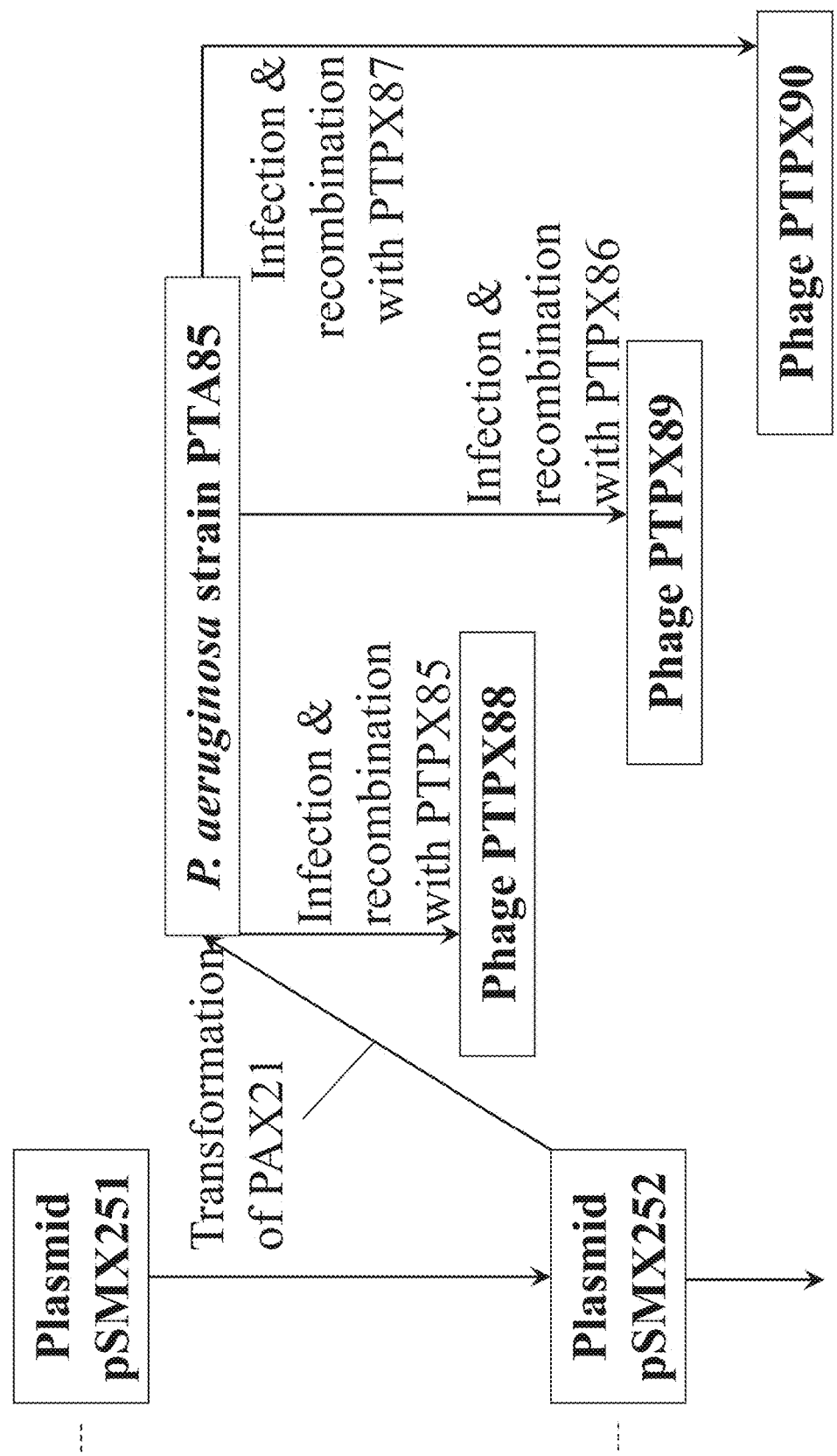
Figure 6C:
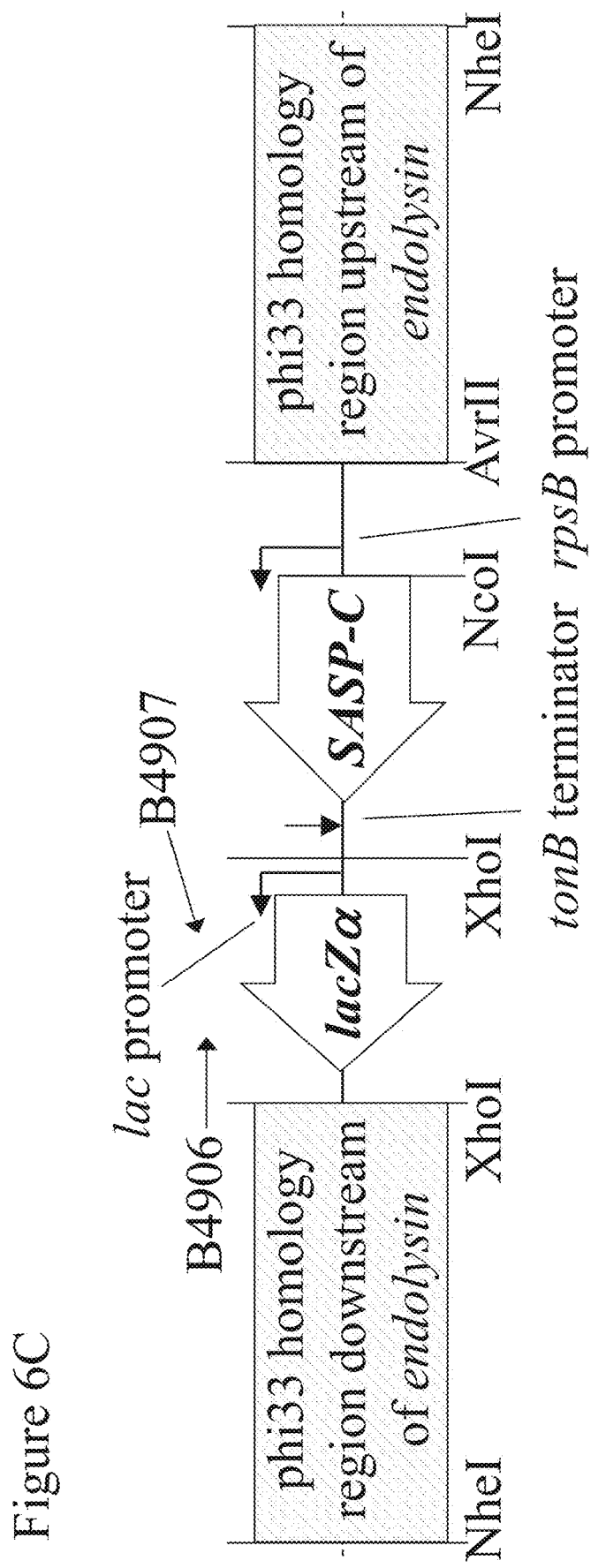
Figure 6D:
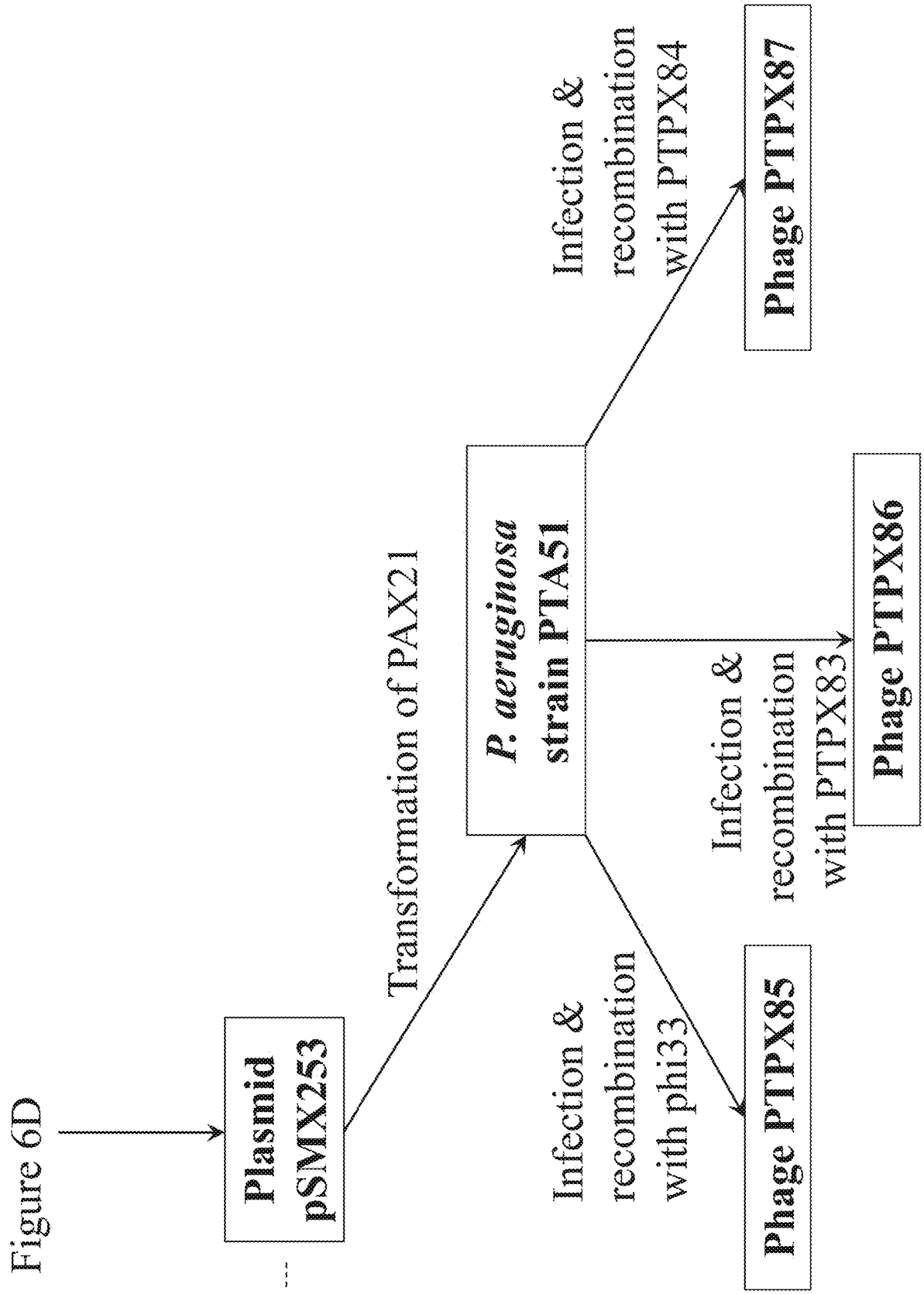
Figure 7A:
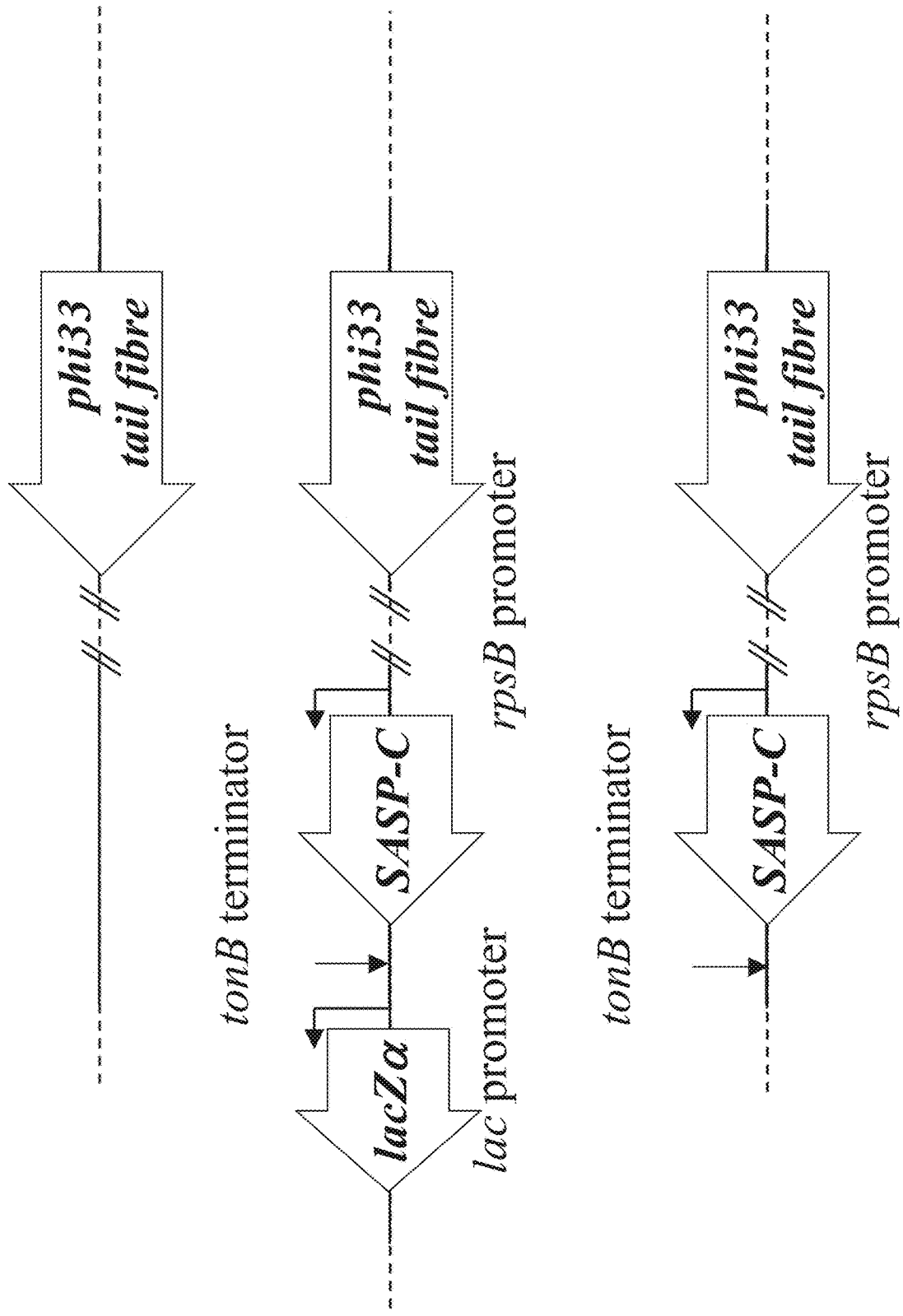
Figure 7B:
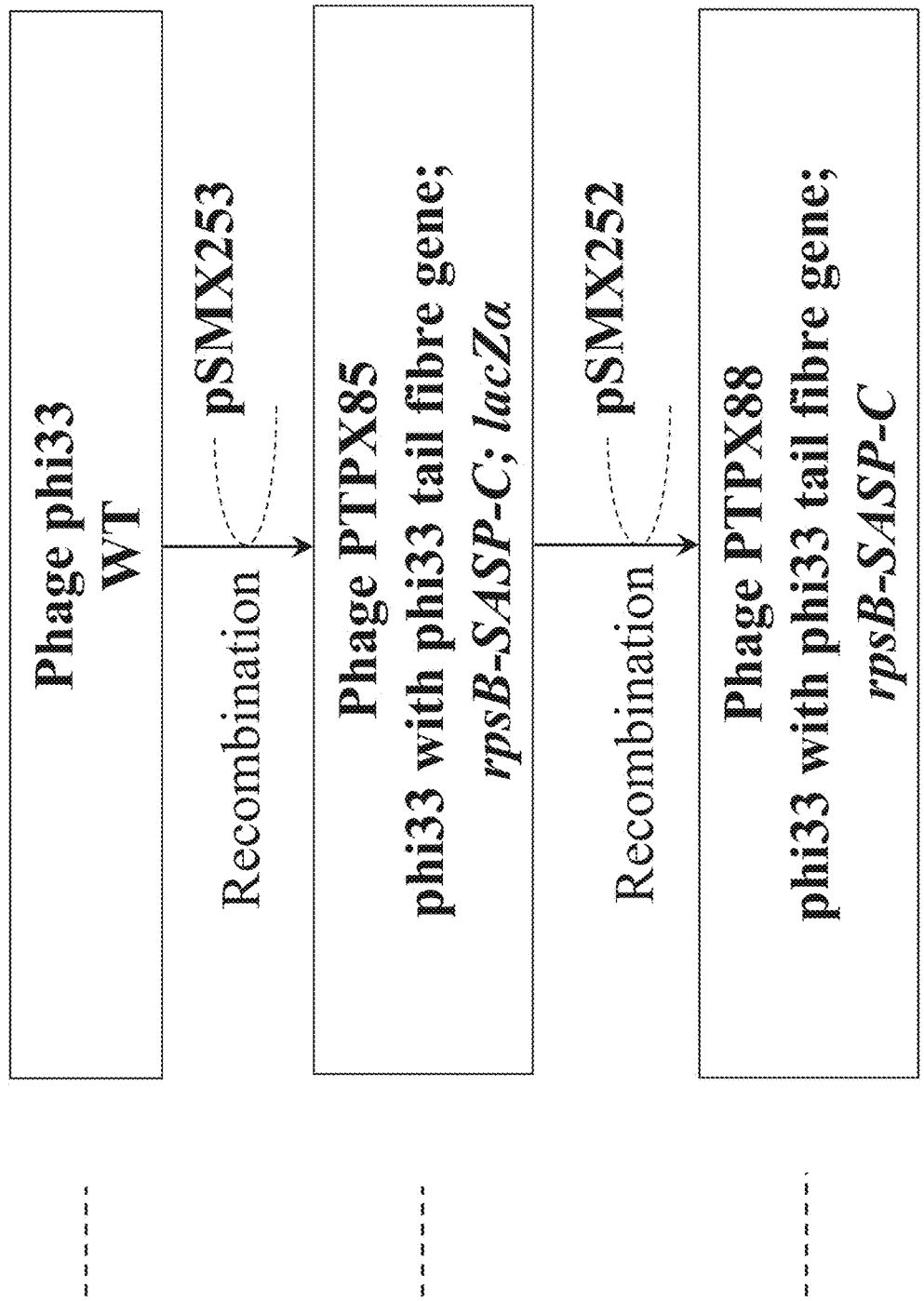
Figure 8A:
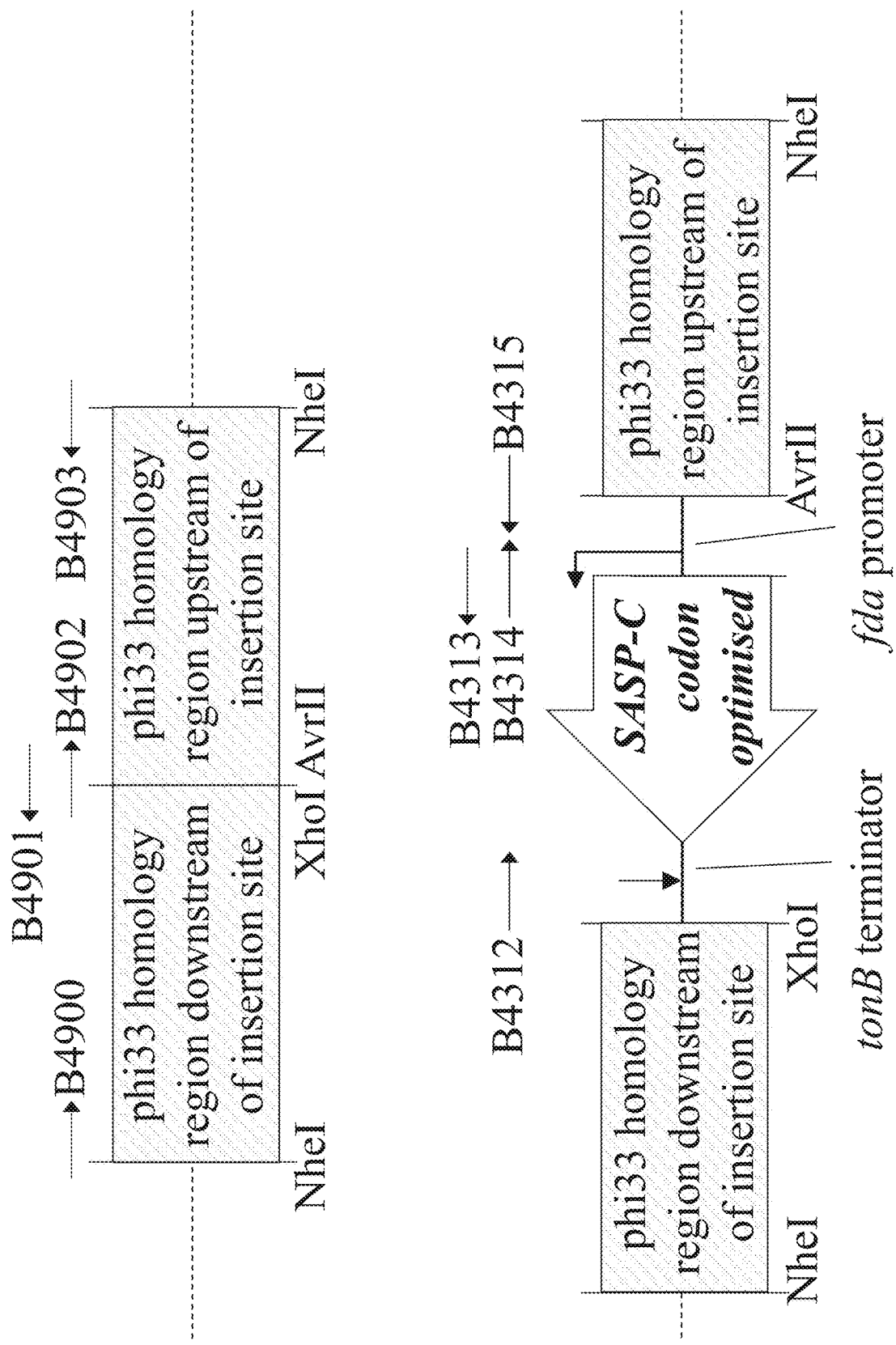
Figure 8B:
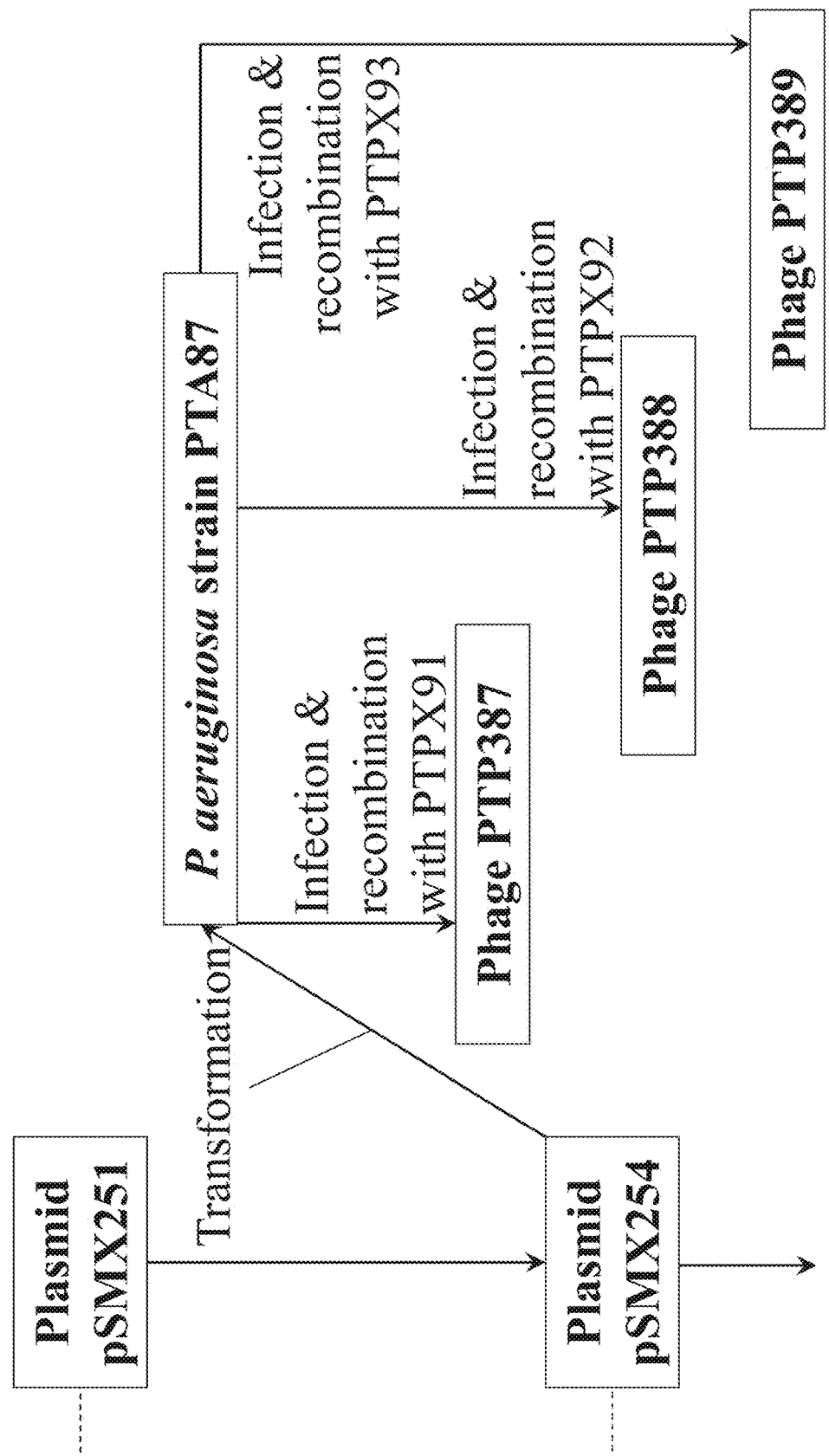
Figure 8C:
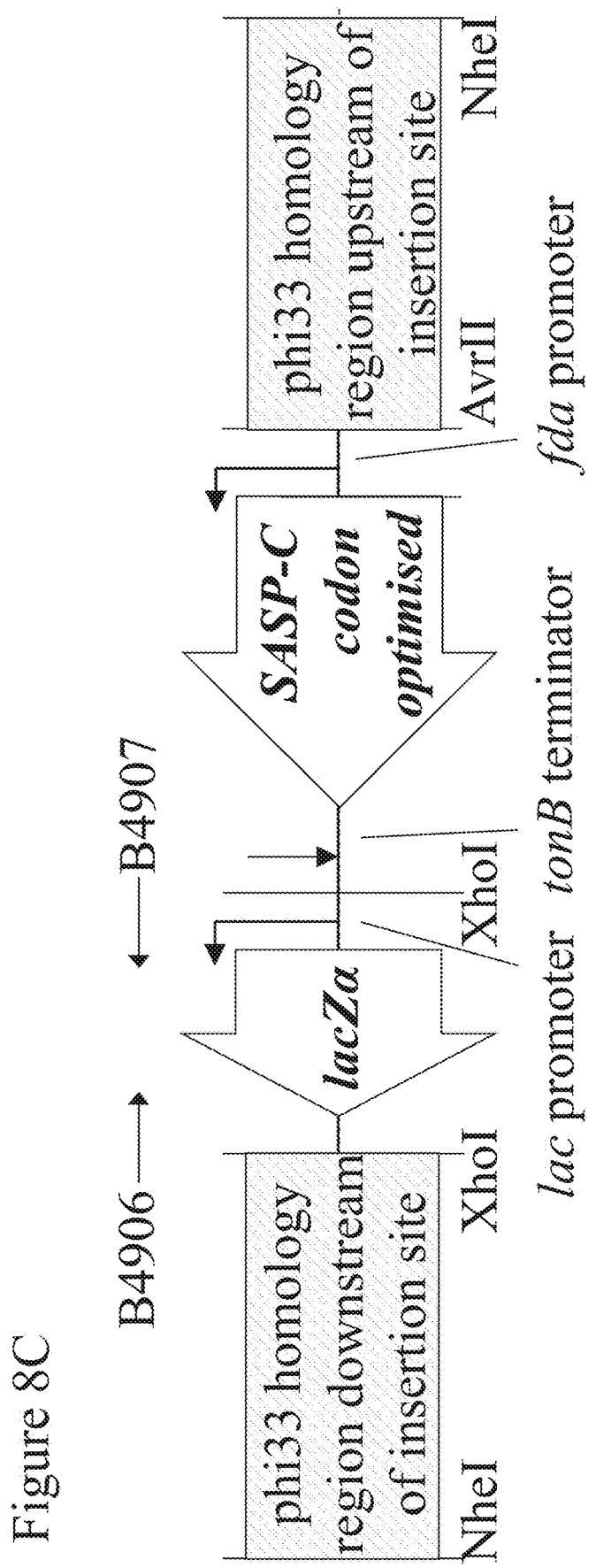
Figure 8D:
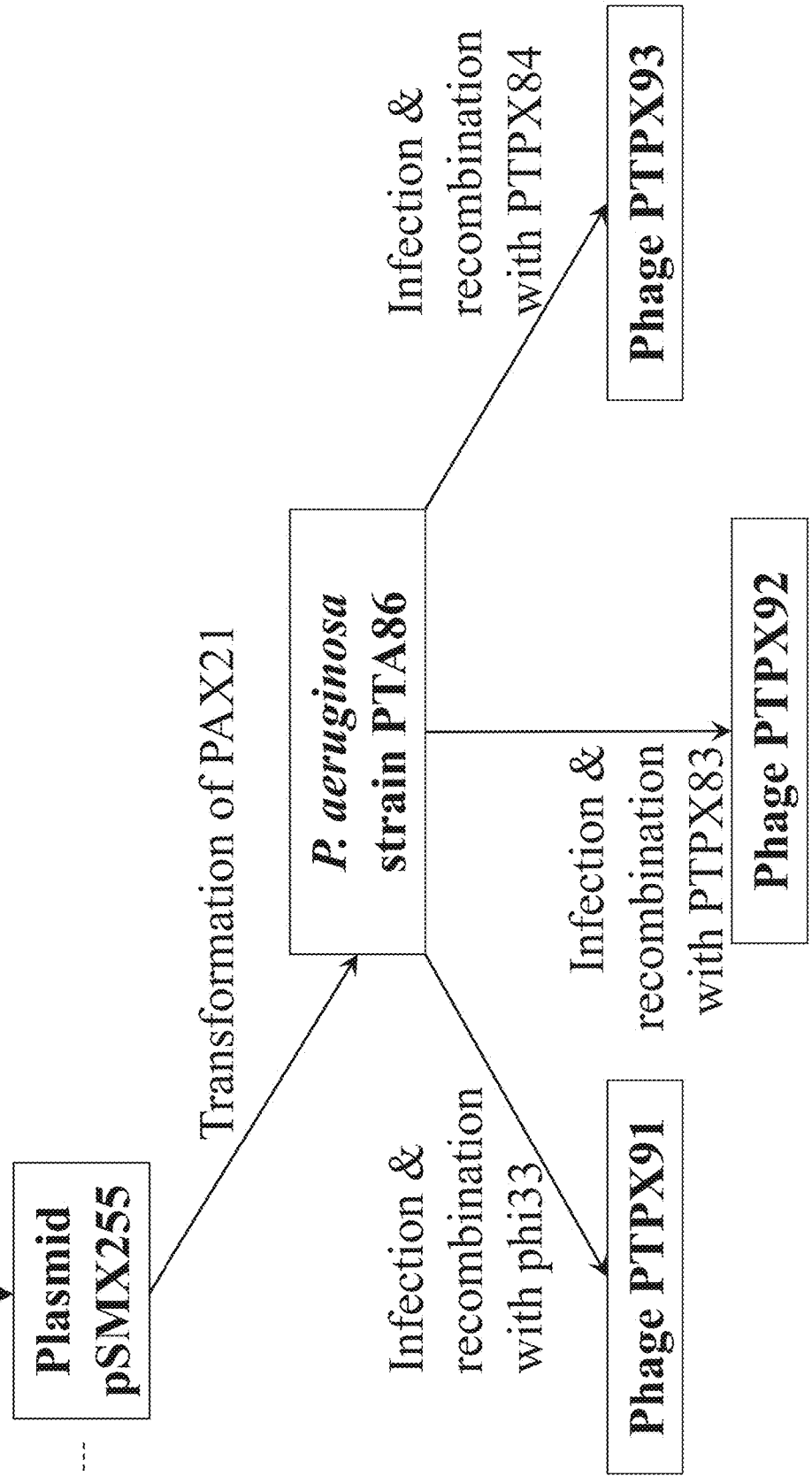
Figure 10A:
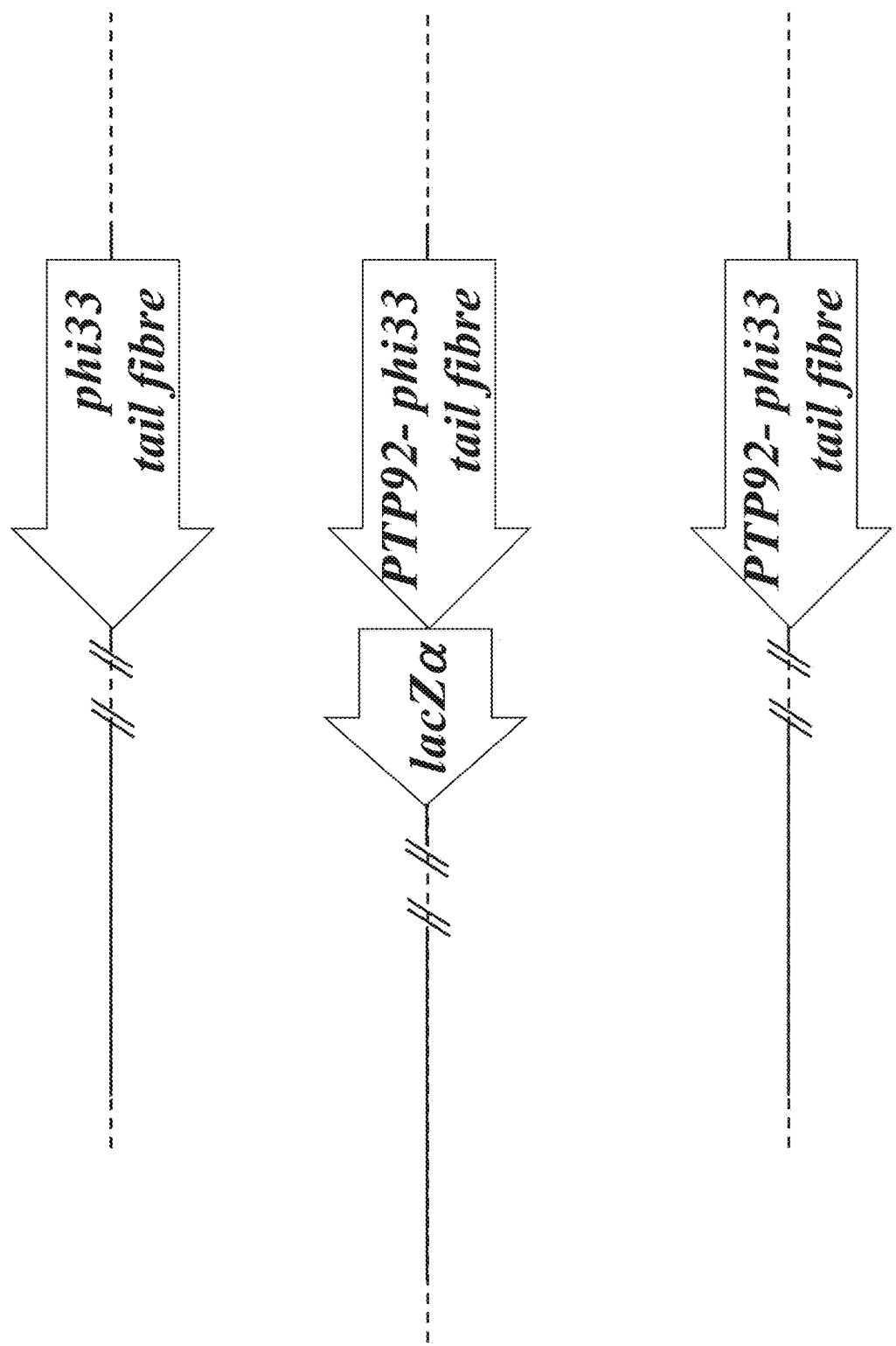
Figure 10B:
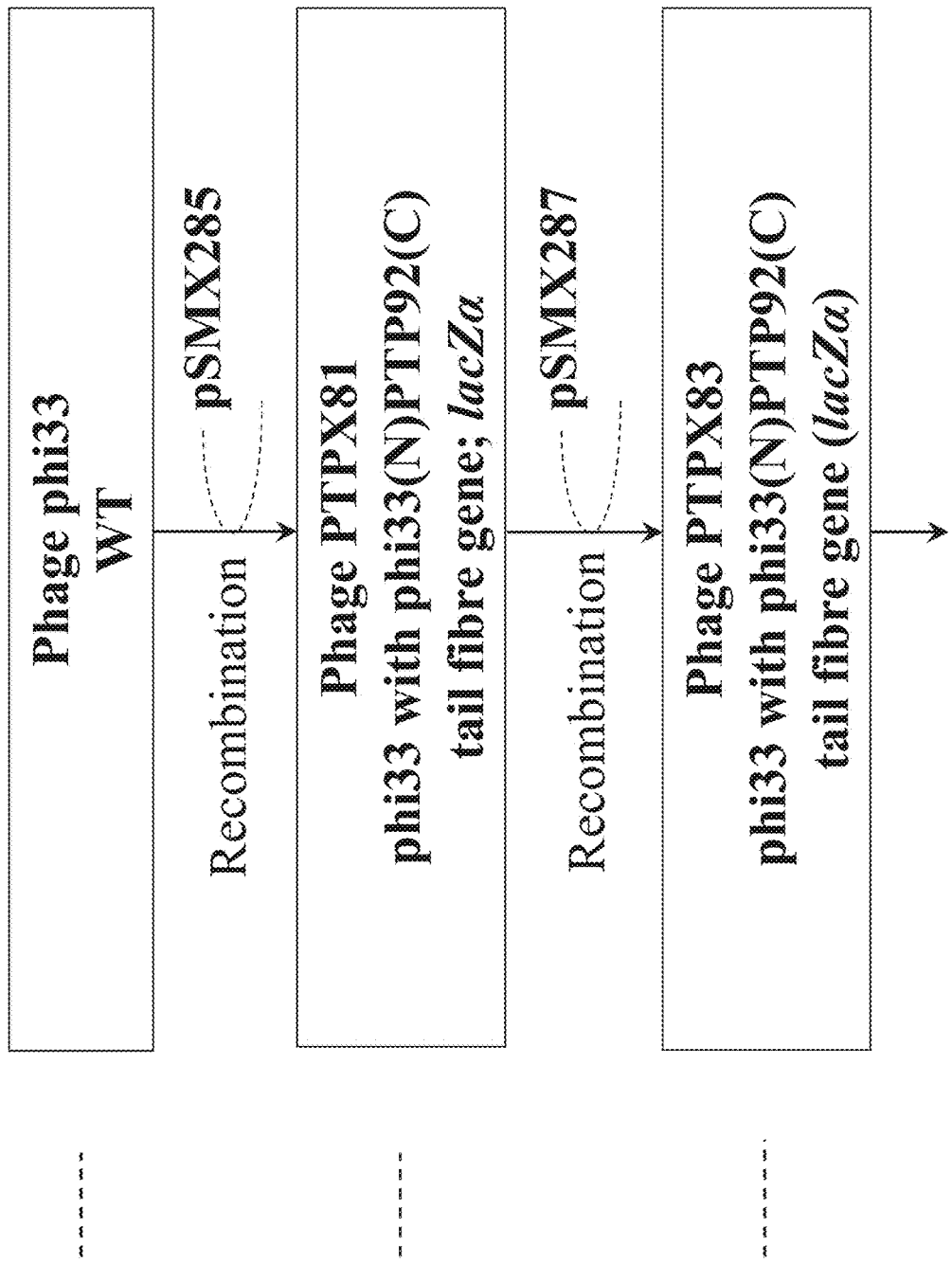
Figure 10C:
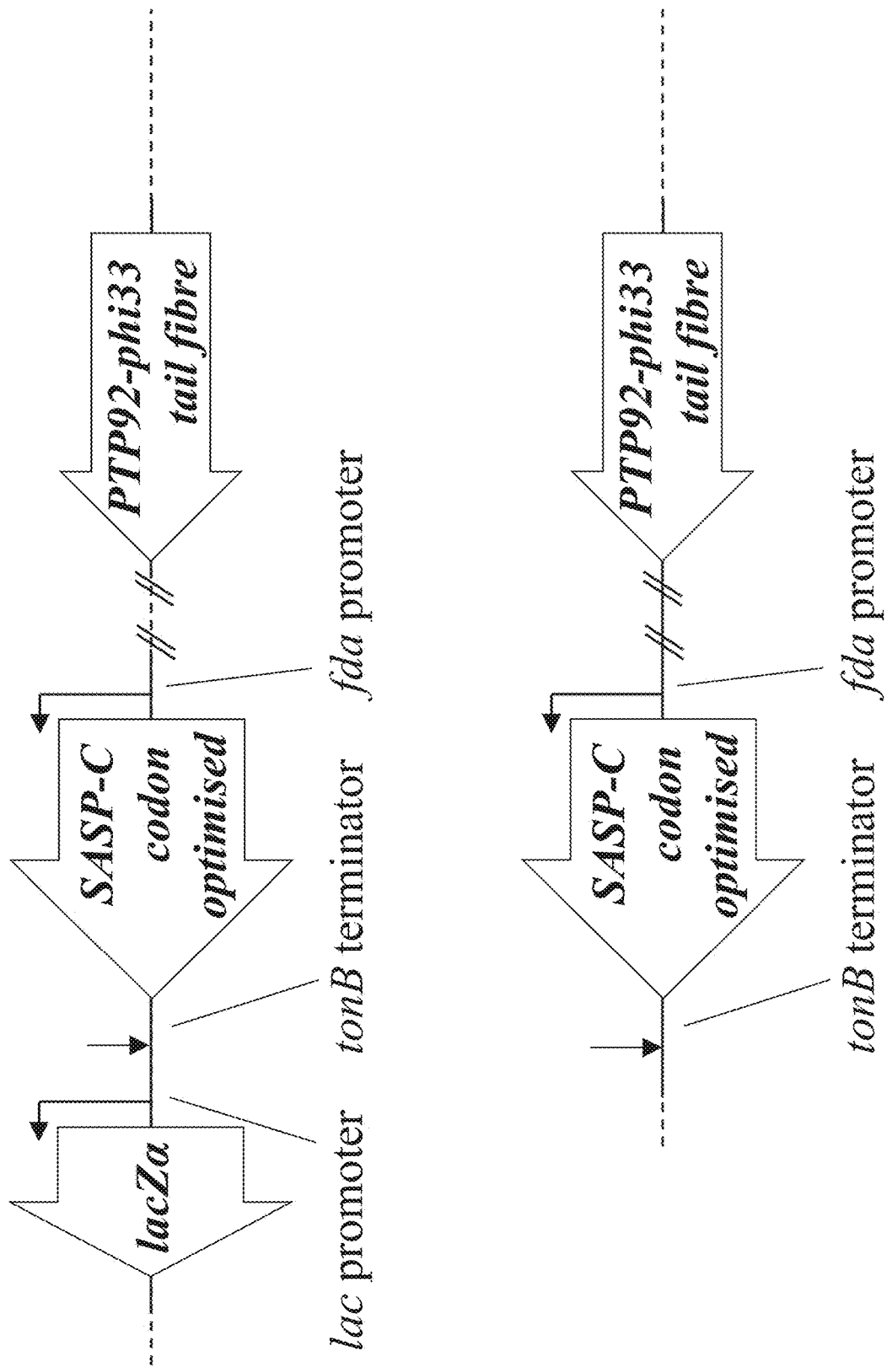
Figure 10D:
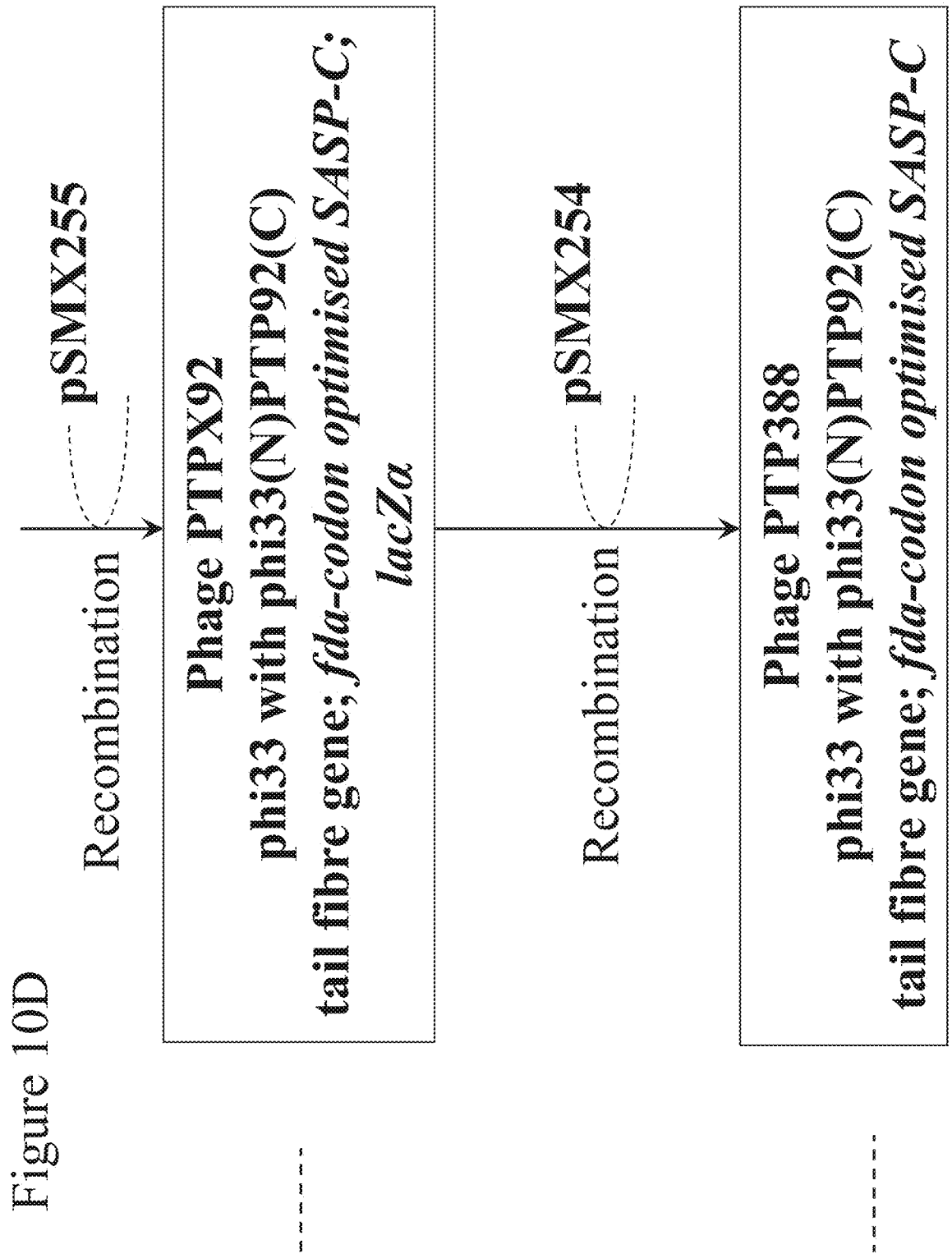
Figure 11A:
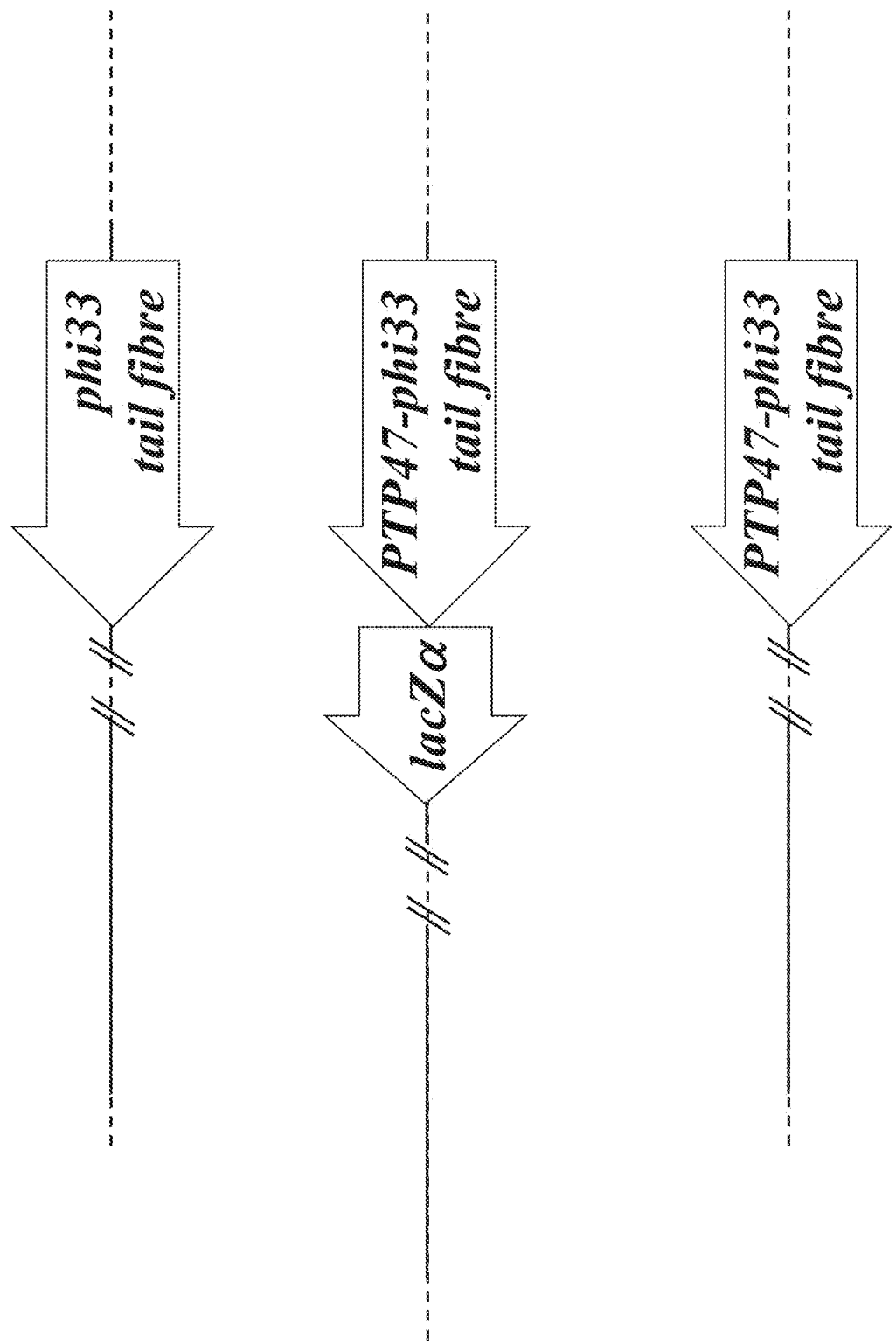
Figure 11B:
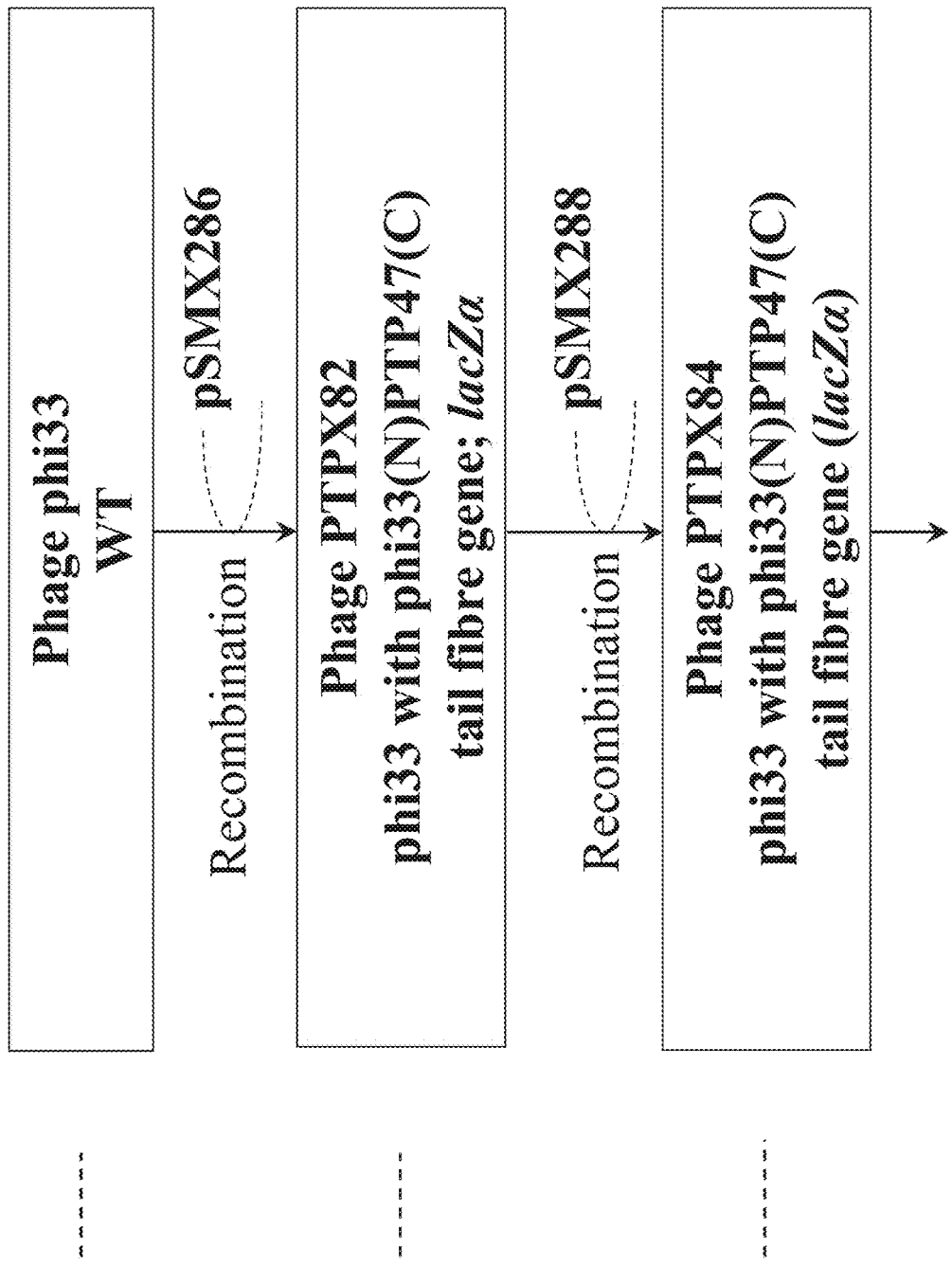
Figure 11C:
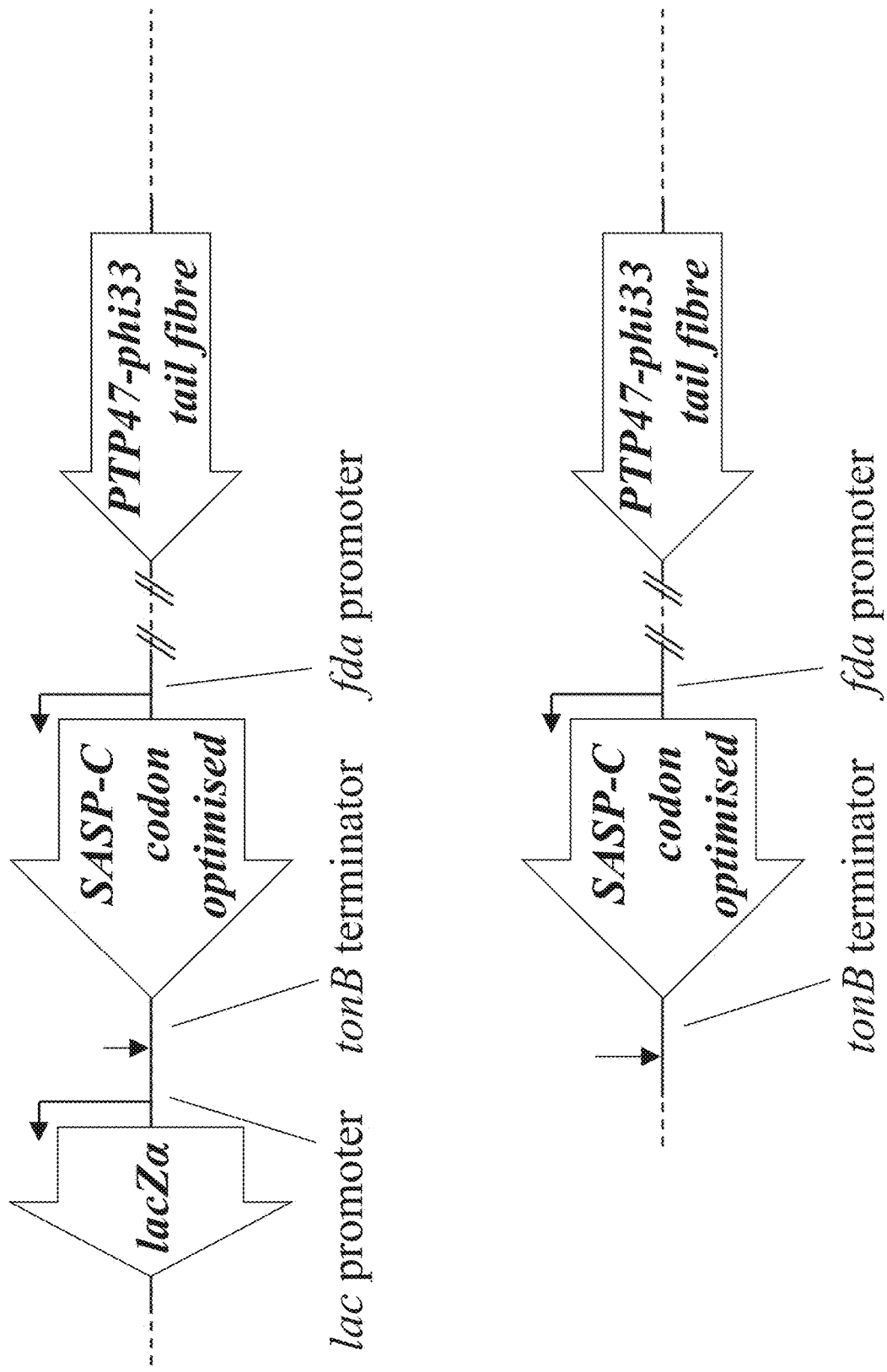
Figure 11D:
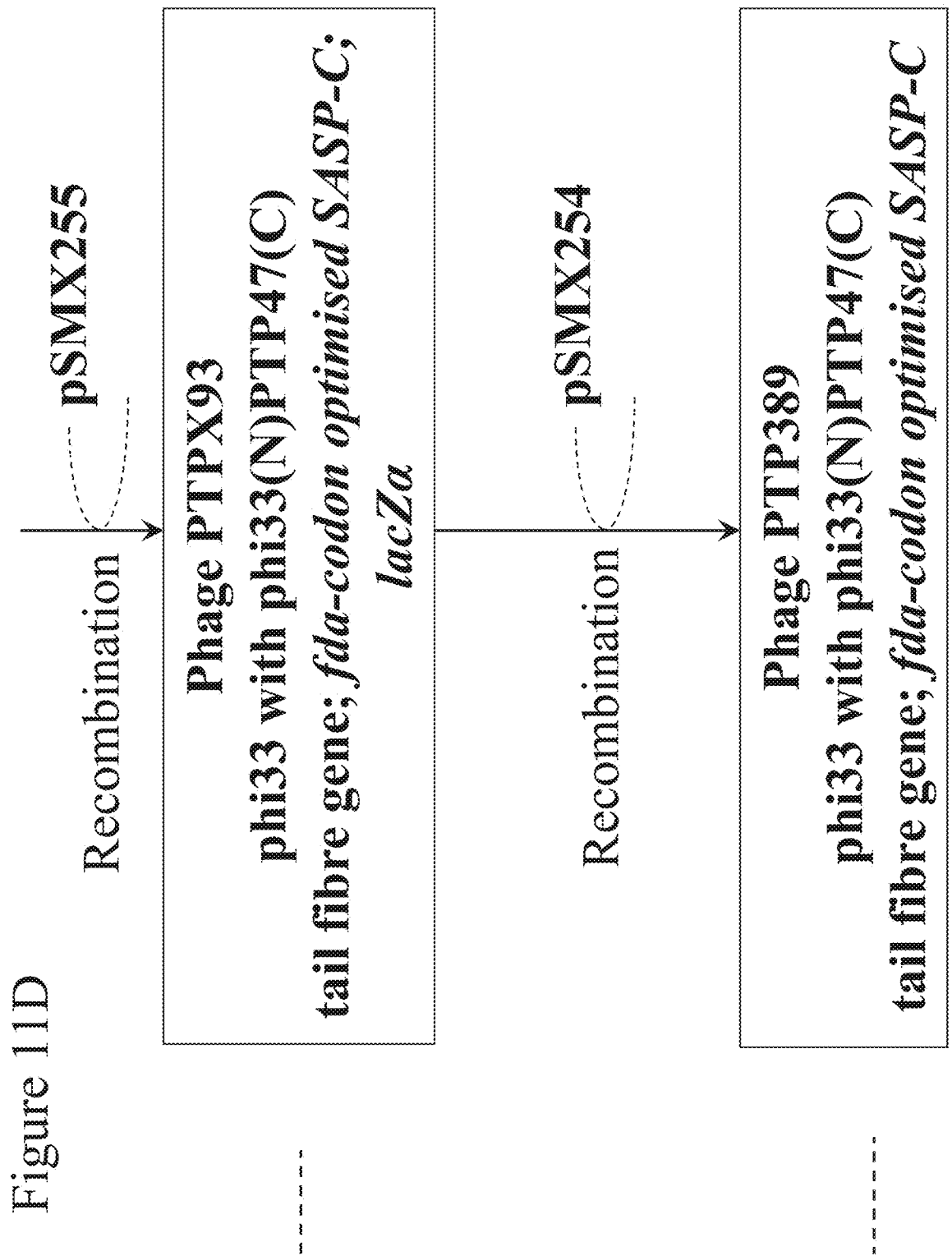
Figure 12A:
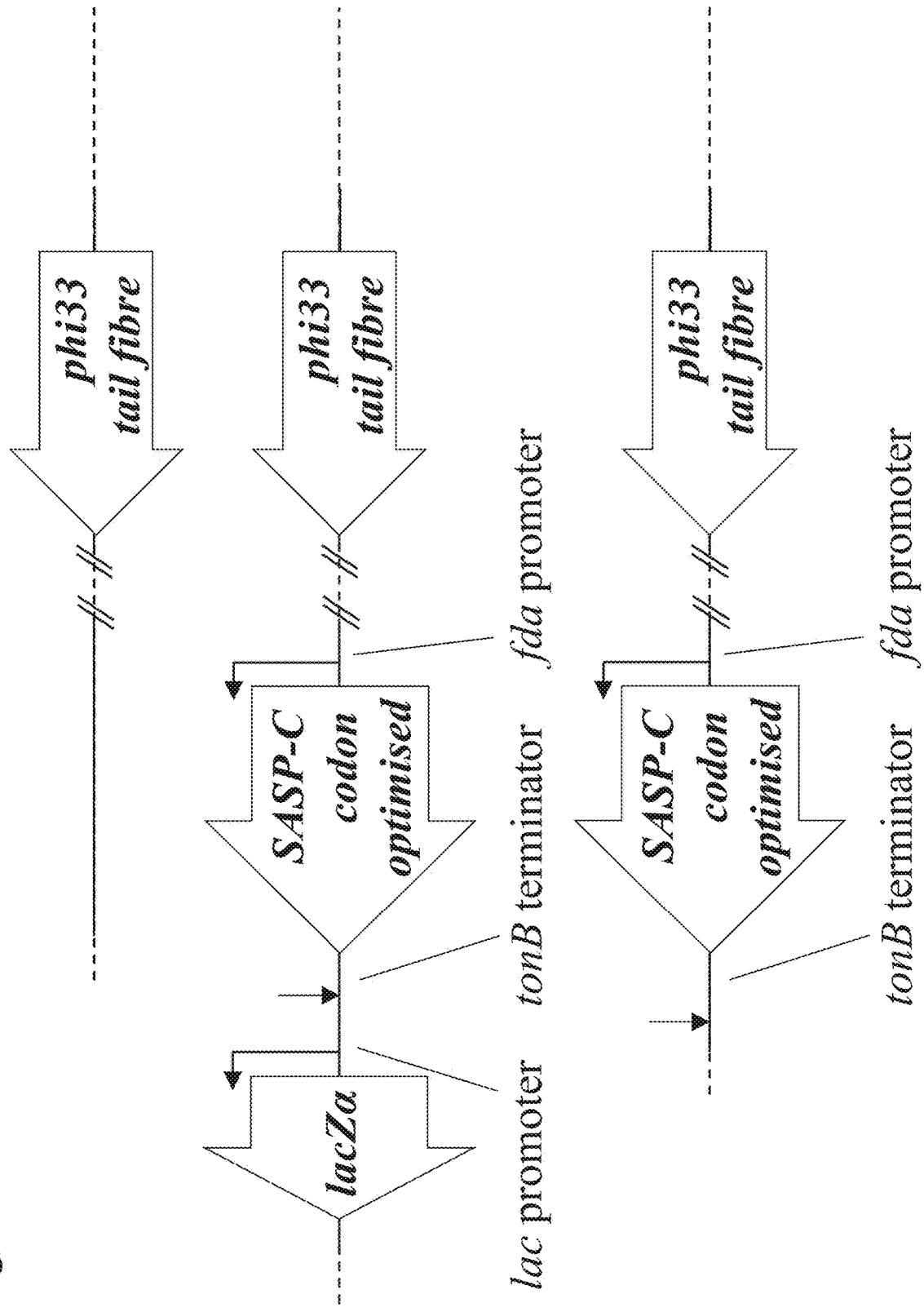
Figure 12B:
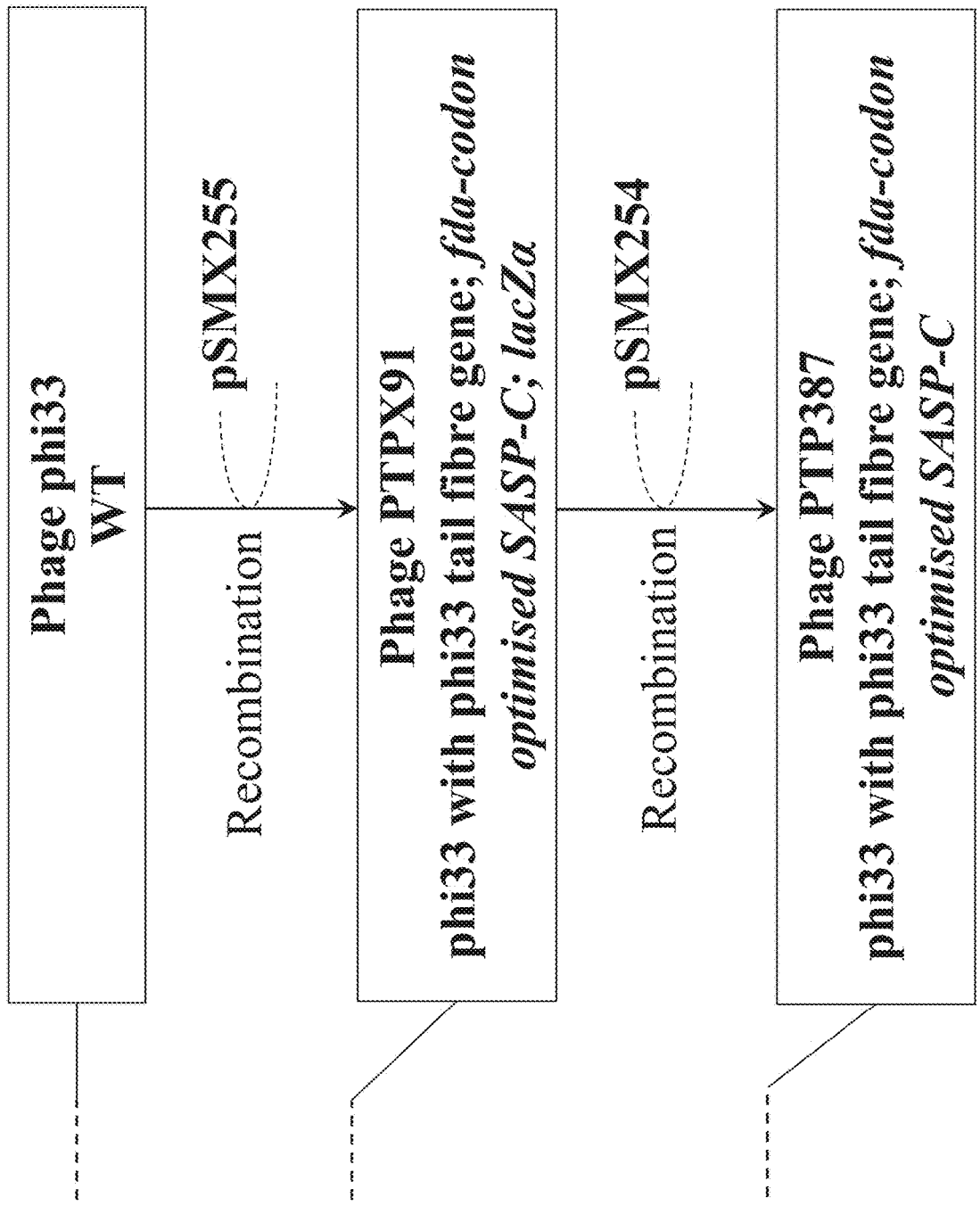

FIGS. 2A, 2B, 2C, and 2D are a schematic diagram showing construction of plasmids with replaced tail fibre sections;

FIGS. 3A, 3B, 3C, and 3D are a schematic diagram showing construction of phage with hybrid tail fibre genes, which may be subsequently modified to introduce SASP-C according to the invention;

FIGS. 4A, 4B, 4C, and 4D are a schematic diagram showing construction of phage with further hybrid tail fibre genes, which may be subsequently modified to introduce SASP-C according to the invention;

FIGS. 5A and 5B are a schematic diagram showing construction of bacteriophage with hybrid tail fibre genes, in which the lacZα marker has been removed;

FIGS. 6A, 6B, 6C, and 6D are a schematic diagram showing construction of plasmids in which SASP-C is introduced into a suitable Phi33 insertion site;

FIGS. 7A and 7B are a schematic diagram showing production of further bacteriophage according to the invention;

FIGS. 8A, 8B, 8C, and 8D are a schematic diagram showing construction of plasmids in which SASP-C codon optimised for expression in *P. aeruginosa* is introduced into a suitable Phi33 insertion site;

FIG. 9 shows the sequence of the SASP-C gene from *Bacillus megaterium* strain KM (ATCC 13632), which has been codon optimised for expression in *P. aeruginosa*; and contains SEQ ID NO: 59;

FIGS. 10A, 10B, 10C, and 10D are a schematic diagram showing production of bacteriophage in which SASP-C which has been codon optimised for expression in *P. aeruginosa* is introduced into a suitable Phi33 insertion site;

FIGS. 11A, 11B, 11C, and 11D are a schematic diagram showing production of further bacteriophage according to the invention;

FIGS. 12A and 12B are a schematic diagram showing production of further bacteriophage according to the invention;

FIGS. 13A, 13B, 13C, 13D and 13E are a CLUSTAL 2.1 multiple sequence alignment of the tail fibre proteins from Phage SPM-1, F8, PB1, C36, LBL3, Phi33, LMA2, KPP12, JG024, PTP92, NH-4, 14-1, PTP47, SN; and contains SEQ ID NOs: 45-58; and FIG. 14. 24 hour time-kill curve showing the in vitro efficacy of PT3.9 against *P. aeruginosa* strains 3503 (A) and ATCC 27853 (B). Cultures were grown in Luria bertani (LB) broth supplemented with 10 mM calcium chloride, 1 mM magnesium sulphate and 1% glucose, at 37° C.

FIG. 15. In vivo efficacy of PT3.9 in a murine bacteraemia model of infection. Mice were treated IV with vehicle (tris buffered saline containing 1 mM magnesium sulphate, 10 mM calcium chloride and 10% v/v glycerol), PTP284 or PTP387 (2 hours post infection with *P. aeruginosa*). The viable cell counts in liver tissue at 22 hours post treatment are shown for each animal in each group (group size=6), the geomean for each data set is represented by a horizontal line.

FIG. 16. In vivo efficacy of PT3.9 in a neutropenic murine pneumonia model of infection. Mice were treated IT (intratrachea) with placebo vehicle (tris buffered saline containing 1 mM magnesium sulphate, 10 mM calcium chloride and 10% v/v glycerol), PT3.9, PT3.8 or Tobramycin (15 minutes post infection with *P. aeruginosa*). The viable cell counts in lung tissue at 24 hours post treatment are shown for each animal in each group (group size=6), the geomean for each data set is represented by a horizontal line.

The product of the invention provides in one aspect a single tail fibre within an individual phage, or a mix of phages where each type of phage has a single, different tail fibre.

This is a summary of the genetic modification of a lytic bacteriophage to render it non-lytic, such that it carries one of a number of possible tail fibre variants, in addition to SASP-C under the control of a promoter that usually controls expression of the *Pseudomonas aeruginosa* 30S ribosomal subunit protein S2 gene (rpsB), or SASP-C codon optimised for expression in *P. aeruginosa*, under the control of a promoter that usually controls expression of the *P. aeruginosa* fructose-1,6-bisphosphate aldolase gene (fda).

Genes can be removed and added to the phage genome using homologous recombination. There are several ways in which phages carrying foreign genes and promoters can be constructed and the following is an example of such methods.

For the construction of a Phi33 derivative it is shown how, using an *E. coli/P. aeruginosa* broad host range vector, as an example only, the existing tail fibre, or a section of the tail fibre, in the bacteriophage genome may be replaced by an alternative tail fibre or tail fibre section from a different bacteriophage, via homologous recombination. It is also shown as an example only, how additional DNA sequences, such as the SASP-C gene from *B. megaterium* under the control of a *P. aeruginosa* rpsB promoter, or the SASP-C gene from *B. megaterium*, codon optimised for expression in *P. aeruginosa*, under the control of a *P. aeruginosa* fda promoter may be added to the bacteriophage genome via homologous recombination.

A tail fibre gene, or section of a tail fibre gene, from an alternative phage may be cloned between two regions of Phi33 DNA that flank the native tail fibre, or section thereof, along with a lacZα genetic marker, in a broad host range *E. coli/P. aeruginosa* vector. This plasmid may be introduced into *P. aeruginosa*, and the resulting strain infected with Phi33. Following harvesting of progeny phage, double recombinants in which the native Phi33 tail fibre or tail fibre section, has been replaced by the new tail fibre or tail fibre section and lacZα, may be isolated by plaquing on a suitable P. aeruginosa (lacZΔM15+) host strain using medium containing a chromogenic substrate that detects the action of β-galactosidase.

In a subsequent step, the lacZα marker may be removed from the bacteriophage genomes by making versions of the previously described tail fibre region recombination plasmids that do not contain the lacZα marker, introducing the new plasmids into suitable P. aeruginosa host strains and infecting with the previously modified bacteriophage derivatives of Phi33 carrying the corresponding alternative tail fibre gene, or section thereof, along with the lacZα marker. Recombinants that retain the new tail fibre or tail fibre section, but from which lacZα has been removed, may be isolated by plaquing on a suitable P. aeruginosa (lacZΔM15+) host strain using medium containing a chromogenic substrate that detects the action of β-galactosidase.

In a subsequent step, a similar homologous recombination may be used to introduce the gene for SASP-C, under the control of a P. aeruginosa rpsB promoter, while simultaneously adding an E. coli lacZα reporter gene for the identification of recombinant phage, into Phi33, or any of the previously described Phi33 derivatives, or similar bacteriophage or similar derivatives. A region consisting of SASP-C controlled by the rpsB promoter, and the E. coli lacZα allele, may be cloned between two regions of Phi33 that flank a suitable insertion site, such as the intergenic region located immediately downstream of the Phi33 tail fibre operon, in a broad host range E. coli/P. aeruginosa vector. This plasmid may be transferred to a suitable P. aeruginosa (lacZΔM15+) strain, and the resulting strain infected by Phi33 or the previously constructed Phi33 derivative (from which the initial lacZα marker has been removed). Progeny phage may be harvested and double recombinants identified by plaquing on P. aeruginosa (lacZΔM15+), looking for acquisition of the new lacZα reporter on medium containing a chromogenic substrate that detects the action of β-galactosidase.

In an alternative subsequent step, a similar homologous recombination may be used to introduce the gene for SASP-C that has been codon optimised for expression in P. aeruginosa, under the control of a P. aeruginosa fda promoter, while simultaneously adding an E. coli lacZα reporter gene for the identification of recombinant phage, into Phi33, or any of the previously described Phi33 derivatives, or similar bacteriophage or similar derivatives. A region consisting of codon optimised SASP-C controlled by the fda promoter, and the E. coli lacZα allele, may be cloned between two regions of Phi33 that flank a suitable insertion site, such as the intergenic region located immediately downstream of the Phi33 tail fibre operon, in a broad host range E. coli/P. aeruginosa vector. This plasmid may be transferred to a suitable P. aeruginosa (lacZΔM15+) strain, and the resulting strain infected by Phi33 or the previously constructed Phi33 derivative (from which the initial lacZα marker has been removed). Progeny phage may be harvested and double recombinants identified by plaquing on P. aeruginosa (lacZΔM15+), looking for acquisition of the new lacZα reporter on medium containing a chromogenic substrate that detects the action of β-galactosidase.

Since these bacteriophage to be modified are lytic (rather than temperate), another requirement for these described steps of bacteriophage construction is the construction of a suitable host P. aeruginosa strain that carries the E. coli lacZΔM15 gene at a suitable location in the bacterial genome, to complement the lacZα phenotypes of the desired recombinant bacteriophage. As an example, the construction of these P. aeruginosa strains may be achieved via homologous recombination using an E. coli vector that is unable to replicate in P. aeruginosa. The genomic location for insertion of the lacZΔM15 transgene should be chosen such that no essential genes are affected and no unwanted phenotypes are generated through polar effects on the expression of adjacent genes. As an example, one such location may be immediately downstream of the P. aeruginosa strain PAO1 phoA homologue.

The E. coli lacZΔM15 allele may be cloned into an E. coli vector that is unable to replicate in P. aeruginosa, between two regions of P. aeruginosa strain PAO1 genomic DNA that flank the 3' end of phoA. This plasmid may be introduced into P. aeruginosa and isolates having undergone a single homologous recombination to integrate the whole plasmid into the genome selected according to the acquisition of tetracycline (50 µg/ml) resistance. Isolates (lacZΔM15+) which have undergone a second homologous recombination event may then be isolated on medium containing 10% sucrose (utilising the sacB counter-selectable marker present on the plasmid backbone).

In a subsequent step, a similar homologous recombination may be used to remove the lacZα marker from the previously described, (lacZα+) Phi33 derivatives that have been modified to introduce the gene for SASP-C, under the control of a P. aeruginosa rpsB promoter. A region consisting of SASP-C controlled by the rpsB promoter, may be cloned between two regions of Phi33 that flank the chosen insertion site, in a broad host range E. coli/P. aeruginosa vector. This plasmid may be transferred to a suitable P. aeruginosa (lacZΔM15+) strain, and the resulting strain infected by the previously described (lacZα+) Phi33 derivatives that have been modified to introduce the gene for SASP-C, under the control of a P. aeruginosa rpsB promoter. Progeny phage may be harvested and double recombinants identified by plaquing on P. aeruginosa (lacZΔM15+), looking for loss of the lacZα reporter on medium containing a chromogenic substrate that detects the action of β-galactosidase.

In an alternative subsequent step, a similar homologous recombination may be used to remove the lacZα marker from the previously described, (lacZα+) Phi33 derivatives that have been modified to introduce the gene for SASP-C, codon optimised for expression in P. aeruginosa, under the control of a P. aeruginosa fda promoter. A region consisting of SASP-C, codon optimised for expression in P. aeruginosa, controlled by the fda promoter, may be cloned between two regions of Phi33 that flank the chosen insertion site, in a broad host range E. coli/P. aeruginosa vector. This plasmid may be transferred to a suitable P. aeruginosa (lacZΔM15+) strain, and the resulting strain infected by the previously described (lacZα+) Phi33 derivatives that have been modified to introduce the gene for SASP-C, codon optimised for expression in P. aeruginosa, under the control of a P. aeruginosa fda promoter. Progeny phage may be harvested and double recombinants identified by plaquing on P. aeruginosa (lacZΔM15+), looking for loss of the lacZα reporter on medium containing a chromogenic substrate that detects the action of β-galactosidase.

Experimental Procedures

PCR reactions to generate DNA for cloning purposes may be carried out using Herculase II Fusion DNA polymerase (Agilent Technologies), depending upon the melting temperatures (Tm) of the primers, according to manufacturers instructions. PCR reactions for screening purposes may be carried out using Taq DNA polymerase (NEB), depending upon the Tm of the primers, according to manufacturers instructions. Unless otherwise stated, general molecular biology techniques, such as restriction enzyme digestion, agarose gel electrophoresis, T4 DNA ligase-dependent ligations, competent cell preparation and transformation may be based upon methods described in Sambrook et al., (1989). Enzymes may be purchased from New England Biolabs or Thermo Scientific. DNA may be purified from enzyme reactions and prepared from cells using Qiagen DNA purification kits. Plasmids may be transferred from *E. coli* strains to *P. aeruginosa* strains by conjugation, mediated by the conjugation helper strain *E. coli* HB101 (pRK2013). A chromogenic substrate for β-galactosidase, S-gal, that upon digestion by β-galactosidase forms a black precipitate when chelated with ferric iron, may be purchased from Sigma (S9811).

Primers may be obtained from Sigma Life Science. Where primers include recognition sequences for restriction enzymes, additional 2-6 nucleotides may be added at the 5' end to ensure digestion of the PCR-amplified DNA.

All clonings, unless otherwise stated, may be achieved by ligating DNAs overnight with T4 DNA ligase and then transforming them into *E. coli* cloning strains, such as DH5α or TOP10, with isolation on selective medium, as described elsewhere (Sambrook et al., 1989).

An *E. coli/P. aeruginosa* broad host range vector, such as pSM1080A, may be used to transfer genes between *E. coli* and *P. aeruginosa*. pSM1080A was previously produced by combining the broad host-range origin of replication from a *P. aeruginosa* plasmid, oriT from pRK2, the tetAR selectable marker for use in both *E. coli* and *P. aeruginosa*, from plasmid pRK415, and the high-copy-number, *E. coli* origin of replication, oriV, from plasmid pUC19.

An *E. coli* vector that is unable to replicate in *P. aeruginosa*, pSM1104, may be used to generate *P. aeruginosa* mutants by allelic exchange. pSM1104 was previously produced by combining oriT from pRK2, the tetAR selectable marker for use in both *E. coli* and *P. aeruginosa*, from plasmid pRK415, the high-copy-number, *E. coli* origin of replication, oriV, from plasmid pUC19, and the sacB gene from *Bacillus subtilis* strain 168, under the control of a strong promoter, for use as a counter-selectable marker.

Detection of Phi33-like phage (PB1-like phage family) conserved N-terminal tail fibre regions by PCR 1. Primers for the detection of Phi33-like phage-like tail fibre genes in experimental phage samples may be designed as follows:

The DNA sequences of the tail fibre genes from all sequenced Phi33-like phage (including Phi33, PB1, NH-4, 14-1, LMA2, KPP12, JG024, F8, SPM-1, LBL3, PTP47, C36, PTP92 and SN) may be aligned using Clustal Omega, which is available on the EBI website, and the approximately 2 kb-long highly conserved region mapping to the gene's 5' sequence may be thus identified (positions 31680-33557 in the PB1 genome sequence, Acc. EU716414). Sections of 100% identity among the 11 tail fibre gene sequences may be identified by visual inspection. Three pairs of PCR primers targeting selected absolutely conserved regions, and amplifying PCR products no longer than 1 kb may be chosen as follows: pair B4500 and B4501, defining a 193 bp-long region; pair B4502 and B4503, defining a 774 bp-long region; and pair B4504 and B4505, defining a 365 bp-long region.

Primer B4500 consists of sequence of PB1 phage genome (Acc. EU716414) ranging from position 31680 to 31697. Primer B4501 consists of sequence of PB1 phage genome (Acc. EU716414) ranging from position 31851 to 31872. Primer B4502 consists of sequence of PB1 phage genome (Acc. EU716414) ranging from position 31785 to 31804. Primer B4503 consists of sequence of PB1 phage genome (Acc. EU716414) ranging from position 32541 to 32558. Primer B4504 consists of sequence of PB1 phage genome (Acc. EU716414) ranging from position 32868 to 32888. Primer B4505 consists of sequence of PB1 phage genome (Acc. EU716414) ranging from position 33213 to 33232.

```
B4500
                                        (SEQ ID NO: 1)
5'-GTGATCACACCCGAACTG-3'

B4501
                                        (SEQ ID NO: 2)
5'-CGATGAAGAAGAGTTGGTTTTG-3'

B4502
                                        (SEQ ID NO: 3)
5'-ACGCCGGACTACGAAATCAG-3'

B4503
                                        (SEQ ID NO: 4)
5'-TCCGGAGACGTTGATGGT-3'

B4504
                                        (SEQ ID NO: 5)
5'-CCTTTCATCGATTTCCACTTC-3'

B4505
                                        (SEQ ID NO: 6)
5'-TTCGTGGACGCCCAGTCCCA-3'
```

2. Phi33-like tail fibre genes may be detected in experimental phage samples as follows:

Plaques of isolated phage of environmental origin may be picked from agar plates and added to water and incubated for 30 minutes, making plaque soak outs. The plaque soak outs may be diluted and a portion added to PCR reactions containing one or all of the above primer pairs, and PCR may be performed according to a standard protocol. PCR products may be visualised on a 1.5% agarose gel with ethidium bromide staining, and evaluated for their size. PCR products of the correct size for the primer pair used may be gel-extracted and submitted to an external facility for sequencing. Sequencing results may be compared with the available tail fibre gene sequences in order to confirm the identity of the PCR product.

Construction of plasmids to generate *Pseudomonas aeruginosa* strains carrying the *Escherichia coli* lacZΔM15 gene, immediately downstream of the phoA locus of the bacterial genome 1. Plasmid pSMX200 (FIG. 1), comprising pSM1104 carrying DNA flanking the 3' end of the *P. aeruginosa* PAO1 phoA homologue, may be constructed as follows.

A region comprising the terminal approximately 1 kb of the phoA gene from *P. aeruginosa* may be amplified by PCR using primers B4200 and B4201 (FIG. 1). The PCR product may then be cleaned and digested with SpeI and BglII. A second region comprising approximately 1 kb downstream of the phoA gene from *P. aeruginosa*, including the 3' end of the PA3297 open reading frame, may be amplified by PCR using primers B4202 and B4203 (FIG. 1). This second PCR product may then be cleaned and digested with BglII and XhoI. The two digests may be cleaned again and ligated to pSM1104 that has been digested with SpeI and XhoI, in a 3-way ligation, to yield plasmid pSMX200 (FIG. 1).

Primer B4200 consists of a 5' SpeI restriction site (underlined), followed by sequence located approximately 1 kb upstream of the stop codon of phoA from *P. aeruginosa* strain PAO1 (FIG. 1). Primer B4201 consists of 5' BglII and AflII restriction sites (underlined), followed by sequence complementary to the end of the phoA gene from *P. aeruginosa* strain PAO1 (the stop codon is in lower case; FIG. 1). Primer B4202 consists of 5' BglII and NheI restriction sites (underlined), followed by sequence immediately downstream of the stop codon of the phoA gene from *P. aeruginosa* strain PAO1 (FIG. 1). Primer B4203 consists of a 5' XhoI restriction site (underlined), followed by sequence within the PA3297 open reading frame, approximately 1 kb downstream of the phoA gene from *P. aeruginosa* strain PAO1 (FIG. 1).

```
Primer B4200
                                  (SEQ ID NO: 7)
5'-gataACTAGTCCTGGTCCACCGGGGTCAAG-3'

Primer B4201
                                  (SEQ ID NO: 8)
5'-gctcagatcttccttaagtcaGTCGCGCAGGTTCAG-3'

Primer B4202
                                  (SEQ ID NO: 9)
5'-aggaagatctgagctagcTCGGACCAGAACGAAAAAG-3'

Primer B4203
                                  (SEQ ID NO: 10)
5'-gataCTCGAGGCGGATGAACATTGAGGTG-3'
```

2. Plasmid pSMX203 (FIG. 1), comprising pSMX200 carrying lacZΔM15 under the control of a lac promoter, may be constructed as follows.

The lacZΔM15 gene under the control of a lac promoter may be amplified by PCR from *Escherichia coli* strain DH10B using primers B4208 and B4209 (FIG. 1). The resulting PCR product may then be digested with BglII and NheI, and ligated to pSMX200 that has also been digested with BglII and NheI, to yield plasmid pSMX203 (FIG. 1).

Primer B4208 consists of a 5' BglII restriction site (underlined), followed by sequence of the lac promoter (FIG. 1). Primer B4209 consists of a 5' NheI restriction site (underlined), followed by a bi-directional transcriptional terminator and sequence complementary to the 3' end of lacZΔM15 (underlined, in bold; FIG. 1).

```
Primer B4208
                                  (SEQ ID NO: 11)
5'-gataagatctgagcgcaacgcaattaatgtg-3'

Primer B4209
                                  (SEQ ID NO: 12)
5'-gatagctagcAGTCAAAAGCCTCCGGTCGGAGGCTTTTGACTTTATT

TTTGACACCAGACCAAC-3'
```

Genetic modification of *Pseudomonas aeruginosa* to introduce the *Escherichia coli* lacZΔM15 gene immediately downstream of the phoA locus of the bacterial genome 1. Plasmid pSMX203 (FIG. 1) may be transferred to *P. aeruginosa* by conjugation, selecting for primary recombinants by acquisition of resistance to tetracycline (50 µg/ml).

2. Double recombinants may then be selected via sacB-mediated counterselection, by plating onto medium containing 10% sucrose.

3. Isolates growing on 10% sucrose may then be screened by PCR to confirm that lacZΔM15 has been introduced downstream of the *P. aeruginosa* phoA gene.

4. Following verification of an isolate (PAX21), this strain may then be used as a host for further modification of bacteriophage, where complementation of a lacZα reporter is required.

Construction of a plasmid to replace the 3' section of the Phi33 tail fibre with that of PTP92, utilising a lacZα screening process 1. pSMX284 (FIG. 2), comprising pSM1080A carrying the region immediately downstream of the Phi33 tail fibre gene, may be constructed as follows.

A 1 kb region of Phi33 sequence covering the terminal 20 bases of the Phi33 tail fibre, and the adjacent downstream region, may be amplified by PCR using primers B4222 and B4249 (FIG. 2). The resulting PCR product may then be cleaned and digested with NheI, and ligated to pSM1080A that has also been digested with NheI and then treated with alkaline phosphatase prior to ligation, yielding plasmid pSMX284 (FIG. 2).

Primer B4222 consists of a 5' NheI restriction site (underlined), followed by sequence from Phi33, approximately 1 kb downstream of the end of the Phi33 tail fibre gene (FIG. 2). B4249 consists of 5' NheI-KpnI-AvrII restriction sites (underlined), followed by sequence complementary to the 3' end of the Phi33 tail fibre and sequence immediately downstream of the tail fibre open reading frame (FIG. 2).

```
B4222
                                  (SEQ ID NO: 13)
5'-gataGCTAGCATGGTTTTCACGACCATG-3'

B4249
                                  (SEQ ID NO: 14)
5'-GATAGCTAGCGAGGTACCGACCTAGGTTTTCCAGCGAGTGACGTAA

AATG-3'
```

2. pSMX285 (FIG. 2), comprising pSMX284 carrying lacZα, a 3' section of the PTP92 tail fibre gene sequence, and a region of Phi33 sequence comprising the 5' end of the tail fibre gene and sequence located immediately upstream of the Phi33 tail fibre gene, may be constructed as follows.

The lacZα open reading frame may be amplified by PCR from pUC19 using primers B4250 and B4252 (FIG. 2). The PTP92 tail fibre 3' section may be amplified by PCR from PTP92 using primers B4251 and B4254 (FIG. 2). The lacZα open reading frame may then be joined to the PTP92 tail fibre gene 3' section by SOEing PCR using the outer primers, B4250 and B4254. A region comprising sequence of the 5' end of the Phi33 tail fibre gene, and sequence located immediately upstream of the Phi33 tail fibre gene, may be amplified by PCR using primers B4253 and B4229 (FIG. 2). This PCR product may then be joined to the PCR product comprising lacZα and the PTP92 tail fibre gene 3' section, by SOEing PCR using the outer primers B4250 and B4229. The resulting PCR product may then be cleaned and digested with AvrII and KpnI, and ligated to pSMX284 that has also been digested with AvrII and KpnI, yielding plasmid pSMX285 (FIG. 2).

Primer B4250 consists of a 5' AvrII restriction site, followed by sequence complementary to the 3' end of the lacZα open reading frame (FIG. 2). Primer B4252 consists of a 5' section of sequence that overlaps the 3' end of the PTP92 tail fibre gene (underlined), followed by sequence of the 5' end of the lacZα open reading frame. Primer B4251 is the reverse complement of primer B4252 (FIG. 2). Primer B4254 consists of 5' sequence from within the Phi33 tail fibre gene (underlined), followed by sequence within the 3' end of the PTP92 tail fibre gene (FIG. 2). Primer B4253 is the reverse complement of Primer B4254. Primer B4229 consists of a 5' KpnI restriction site (underlined), followed by sequence that is complementary to a region approximately 1 kb upstream of the tail fibre gene in Phi33 (FIG. 2).

Primer B4250
(SEQ ID NO: 15)
5'-GataCCTAGGttagcgccattcgccattc-3'

Primer B4252
(SEQ ID NO: 16)
5'-CTATTCCAGCGGGTAACGTAAAatgaccatgattacggattC-3'

Primer B4251
(SEQ ID NO: 17)
5'-GaatccgtaatcatggtcatTTTACGTTACCCGCTGGAATAG-3'

Primer B4254
(SEQ ID NO: 18)
5'-CAAGCGGGCCGGCTGGTCTCTCGGCAATAACTCCTATGTGATC-3'

Primer B4253
(SEQ ID NO: 19)
5'-GATCACATAGGAGTTATTGCCGAGAGACCAGCCGGCCCGCTTG-3'

Primer B4229
(SEQ ID NO: 20)
5'-gataGGTACCGCGACCGGTCTGTACTTC-3'

Genetic Modification of Phi33 to Replace the 3' Section of the Tail Fibre Gene with that of PTP92

1. Plasmid pSMX285 (FIG. 2; FIG. 3) may be introduced into *P. aeruginosa* strain PAX21 by conjugation, selecting transconjugants on the basis of tetracycline resistance (50 µg/ml), yielding strain PTA80.
2. Strain PTA80 may be infected with phage Phi33, and the progeny phage harvested.
3. Recombinant phage in which the 3' end of the Phi33 tail fibre gene has been replaced by that of PTP92, and to which lacZα has been added, may be identified by plaquing the lysate from step (2) on *P. aeruginosa* strain PAX21, onto medium containing S-gal, looking for black plaques, which are indicative of β-galactosidase activity.
4. PCR may be carried out to check that the tail fibre gene has been replaced, and that lacZα is present.
5. Following identification of a verified isolate (PTPX81; FIG. 3), this isolate may be plaque purified twice more on *P. aeruginosa* strain PAX21, prior to further use.

Construction of a plasmid to replace the 3' section of the Phi33 tail fibre with that of PTP47, utilising a lacZα screening process 1. pSMX286 (FIG. 2), comprising pSMX284 carrying lacZα, a 3' section of the PTP47 tail fibre gene sequence, and a region of Phi33 sequence comprising the 5' end of the tail fibre gene and sequence located immediately upstream of the Phi33 tail fibre gene, may be constructed as follows.

The lacZα open reading frame may be amplified by PCR from pUC19 using primers B4250 and B4258 (FIG. 2). The PTP47 tail fibre 3' section may be amplified by PCR from PTP47 using primers B4259 and B4260 (FIG. 2). The lacZα open reading frame may then be joined to the PTP47 tail fibre gene 3' section by SOEing PCR using the outer primers, B4250 and B4260. A region comprising sequence of the 5' end of the Phi33 tail fibre gene, and sequence located immediately upstream of the Phi33 tail fibre gene, may be amplified by PCR using primers B4261 and B4229 (FIG. 2). This PCR product may then be joined to the PCR product comprising lacZα and the PTP47 tail fibre gene 3' section, by SOEing PCR using the outer primers B4250 and B4229. The resulting PCR product may then be cleaned and digested with AvrII and KpnI, and ligated to pSMX284 that has also been digested with AvrII and KpnI, yielding plasmid pSMX286 (FIG. 2).

Primer B4250 consists of a 5' AvrII restriction site, followed by sequence complementary to the 3' end of the lacZα open reading frame (FIG. 2). Primer B4258 consists of a 5' section of sequence that overlaps the 3' end of the PTP47 tail fibre gene (underlined), followed by sequence of the 5' end of the lacZα open reading frame. Primer B4259 is the reverse complement of primer B4258 (FIG. 2). Primer B4260 consists of 5' sequence from within the Phi33 tail fibre gene (underlined), followed by sequence within the 3' end of the PTP47 tail fibre gene (FIG. 2). Primer B4261 is the reverse complement of Primer B4260. Primer B4229 consists of a 5' KpnI restriction site (underlined), followed by sequence that is complementary to a region approximately 1 kb upstream of the tail fibre gene in Phi33 (FIG. 2).

Primer B4250
(SEQ ID NO: 15)
5'-GataCCTAGGttagcgccattcgccattc-3'

Primer B4258
(SEQ ID NO: 21)
5'-CTTTTCCAGCGAGTGACGTAAAatgaccatgattacggattC-3'

Primer B4259
(SEQ ID NO: 22)
5'-gaatccgtaatcatggtcatTTTACGTCACTCGCTGGAAAAG-3'

Primer B4260
(SEQ ID NO: 23)
5'-CAAGCGGGCCGGCTGGTCTCTCGGCAATAACTCCTATGTGATC-3'

Primer B4261
(SEQ ID NO: 24)
5'-GATCACATAGGAGTTATTGCCGAGAGACCAGCCGGCCCGCTTG-3'

Primer B4229
(SEQ ID NO: 20)
5'-gataGGTACCGCGACCGGTCTGTACTTC-3'

Genetic Modification of Phi33 to Replace the 3' Section of the Tail Fibre Gene with that of PTP47

1. Plasmid pSMX286 (FIG. 2; FIG. 4) may be introduced into *P. aeruginosa* strain PAX21 by conjugation, selecting transconjugants on the basis of tetracycline resistance (50 µg/ml), yielding strain PTA81.
2. Strain PTA81 may be infected with phage Phi33, and the progeny phage harvested.
3. Recombinant phage in which the 3' end of the Phi33 tail fibre gene has been replaced by that of PTP47, and to which lacZα has been added, may be identified by plaquing the lysate from step (2) on *P. aeruginosa* strain PAX21, onto medium containing S-gal, looking for black plaques, which are indicative of β-galactosidase activity.
4. PCR may be carried out to check that the tail fibre gene has been replaced, and that lacZα is present.
5. Following identification of a verified isolate (PTPX82; FIG. 4), this isolate may be plaque purified twice more on *P. aeruginosa* strain PAX21, prior to further use.

Construction of a Plasmid to Remove the lacZα Marker from PTPX81

1. pSMX287 (FIG. 5), comprising pSM1080A carrying a 3' section of the PTP92 tail fibre gene, and a region of Phi33 sequence located immediately downstream of the Phi33 tail fibre gene, may be constructed as follows.

The region of Phi33 sequence located immediately downstream of the Phi33 tail fibre may be amplified by PCR using primers B4222 and B4255 (FIG. 5). The 3' end of the PTP92 tail fibre gene may be amplified by PCR using primers B4256 and B4257 (FIG. 5). These two PCR products may then be joined by SOEing PCR, using the two outer primers B4222 and B4257. The resulting PCR product may then be cleaned, digested with NheI, cleaned again, and ligated to pSM1080A that has also been digested with NheI and then treated with alkaline phosphatase prior to ligation, to yield plasmid pSMX287 (FIG. 5).

Primer B4255 consists of a 5' section of the end of the PTP92 tail fibre gene (underlined), followed by sequence immediately downstream of the Phi33 tail fibre gene (FIG. 5). Primer B4256 is the reverse complement of primer B4255 (FIG. 5). Primer B4257 consists of a 5' NheI restriction site (underlined), followed by sequence of the terminal 1 kb of the PTP92 tail fibre gene (FIG. 5).

Primer B4255
(SEQ ID NO: 25)
5'-CTATTCCAGCGGGTAACGTAAAATGAAATGGACGCGGATCAG-3'

Primer B4256
(SEQ ID NO: 26)
5'-CTGATCCGCGTCCATTTCATTTTACGTTACCCGCTGGAATAG-3'

Primers B4257
(SEQ ID NO: 27)
5'-gataGCTAGCGGCAATAACTCCTATGTGATC-3'

Genetic Modification of PTPX81 to Remove the lacZα Marker

1. Plasmid pSMX287 (FIG. 5; FIG. 3) may be introduced into *P. aeruginosa* strain PAX21 by conjugation, selecting transconjugants on the basis of tetracycline resistance (50 μg/ml), yielding strain PTA82.

2. Strain PTA82 may be infected with phage PTPX81, and the progeny phage harvested.

3. Recombinant phage in which the lacZα marker has been removed may be identified by plaquing the lysate from step (2) on *P. aeruginosa* strain PAX21, onto medium containing S-gal, looking for white plaques, which are indicative of loss of β-galactosidase activity.

4. PCR may be carried out to check that the tail fibre gene has been retained, and that lacZα has been removed.

5. Following identification of a verified isolate (PTPX83; FIG. 3), this isolate may be plaque purified twice more on *P. aeruginosa* strain PAX21, prior to further use.

Construction of a Plasmid to Remove the lacZα Marker from PTPX82

1. pSMX288 (FIG. 5), comprising pSM1080A carrying a 3' section of the PTP47 tail fibre gene, and a region of Phi33 sequence located immediately downstream of the Phi33 tail fibre gene, may be constructed as follows.

The region of Phi33 sequence located immediately downstream of the Phi33 tail fibre may be amplified by PCR using primers B4222 and B4262 (FIG. 5). The 3' end of the PTP47 tail fibre gene may be amplified by PCR using primers B4263 and B4264 (FIG. 5). These two PCR products may then be joined by SOEing PCR, using the two outer primers B4222 and B4264. The resulting PCR product may then be cleaned, digested with NheI, cleaned again, and ligated to pSM1080A that has also been digested with NheI and then treated with alkaline phosphatase prior to ligation, to yield plasmid pSMX288 (FIG. 5).

Primer B4262 consists of a 5' section of the end of the PTP47 tail fibre gene (underlined), followed by sequence immediately downstream of the Phi33 tail fibre gene (FIG. 5). Primer B4263 is the reverse complement of primer B4262 (FIG. 5). Primer B4264 consists of a 5' NheI restriction site (underlined), followed by sequence of the terminal 1 kb of the PTP47 tail fibre gene (FIG. 5).

Primer B4262
(SEQ ID NO: 28)
5'-CTTTTCCAGCGAGTGACGTAAAATGAAATGGACGCGGATCAG-3'

Primer B4263
(SEQ ID NO: 29)
5'-CTGATCCGCGTCCATTTCATTTTACGTCACTCGCTGGAAAAG-3'

Primers B4264
(SEQ ID NO: 30)
5'-gataGCTAGCGGCAATAACTCCTATGTGATC-3'

Genetic Modification of PTPX82 to Remove the lacZα Marker

1. Plasmid pSMX288 (FIG. 5; FIG. 4) may be introduced into *P. aeruginosa* strain PAX21 by conjugation, selecting transconjugants on the basis of tetracycline resistance (50 μg/ml), yielding strain PTA83.

2. Strain PTA83 may be infected with phage PTPX82, and the progeny phage harvested.

3. Recombinant phage in which the lacZα marker has been removed may be identified by plaquing the lysate from step (2) on *P. aeruginosa* strain PAX21, onto medium containing S-gal, looking for white plaques, which are indicative of loss of β-galactosidase activity.

4. PCR may be carried out to check that the tail fibre gene has been retained, and that lacZα has been removed.

5. Following identification of a verified isolate (PTPX84; FIG. 4), this isolate may be plaque purified twice more on *P. aeruginosa* strain PAX21, prior to further use.

Construction of a plasmid to introduce rpsB-SASP-C and lacZα into the phage genome of Phi33, PTPX83, PTPX84, and similar phage 1. Plasmid pSMX251 (FIG. 6), comprising pSM1080A containing regions of Phi33 flanking the chosen insertion site for rpsB-SASP-C, such as the intergenic region immediately downstream of the tail fibre operon, may be constructed as follows.

The region of Phi33 sequence immediately downstream of the chosen insertion site may be amplified by PCR using primers B4900 and B4901 (FIG. 6). This PCR product may then be cleaned and digested with NheI and AvrII. The region of Phi33 sequence immediately upstream of the chosen insertion site may be amplified by PCR using primers B4902 and B4903 (FIG. 6). This second PCR product may then be cleaned and digested with AvrII and NheI. The two PCR product digests may then be cleaned again and ligated to pSM1080A that has been digested with NheI and treated with alkaline phosphatase prior to ligation. Clones carrying one insert of each of the two PCR products may be identified by PCR using primers B4900 and B4903, and NheI restriction digest analysis of the purified putative clones, to identify plasmid pSMX251 (FIG. 6).

Primer B4900 consists of a 5' NheI restriction site (underlined), followed by Phi33 sequence located approximately 500 bp downstream of the Phi33 insertion site that is within the intergenic region immediately downstream of the tail fibre operon (FIG. 6). Primer B4901 consists of 5' AvrII and XhoI restriction sites (underlined), followed by sequence of Phi33 that is complementary to sequence located immediately downstream of the Phi33 insertion site (FIG. 6). Primer B4902 consists of a 5' AvrII restriction site (underlined), followed by Phi33 sequence located immediately upstream of the insertion site (FIG. 6). Primer B4903 consists of a 5' NheI site (underlined), followed by Phi33 sequence that is complementary to sequence located approximately 500 bp upstream of the Phi33 insertion site (FIG. 6).

```
Primer B4900
                                       (SEQ ID NO: 31)
5' gatagctagcTTTCTCGTTTTAATGTCG 3'

Primer B4901
                                       (SEQ ID NO: 32)
5' gataCCTAGGtgCTCGAGTATTCGCCCAAAAGAAAAG 3'

Primer B4902
                                       (SEQ ID NO: 33)
5' gataCCTAGGTCAGGAGCCTTGATTGATC 3'

Primer B4903
                                       (SEQ ID NO: 34)
5' gatagctagcGGACTGGTAAGTCTGGTG 3'
```

2. Plasmid pSMX252 (FIG. 6), comprising pSMX251 containing SASP-C under the control of an rpsB promoter, may be constructed as follows.

The SASP-C gene from *Bacillus megaterium* strain KM (ATCC 13632) may be amplified by PCR using primers B4904 and B4270 (FIG. 6). The resulting PCR product may then be digested with XhoI and NcoI. The rpsB promoter may be amplified by PCR from *P. aeruginosa* using primers B4271 and B4905 (FIG. 6). The resulting PCR product may then be digested with NcoI and AvrII. The two digested PCR products may then be cleaned and ligated to pSMX251 that has been digested with XhoI and AvrII, yielding plasmid pSMX252 (FIG. 6).

Primer B4904 comprises a 5' XhoI restriction site, followed by 5 bases, and then a bi-directional transcriptional terminator, and then sequence complementary to the 3' end of the SASP-C gene from *B. megaterium* strain KM (ATCC 13632) (underlined, in bold; FIG. 6). Primer B4270 comprises a 5' NcoI restriction site (underlined), followed by sequence of the 5' end of the SASP-C gene from *B. megaterium* strain KM (ATCC 13632) (FIG. 6). Primer B4271 comprises a 5' NcoI restriction site (underlined), followed by sequence complementary to the end of the rpsB promoter from *P. aeruginosa* PAO1 (FIG. 6). Primer B4905 comprises a 5' AvrII restriction site (underlined), followed by sequence of the beginning of the rpsB promoter from *P. aeruginosa* PAO1 (FIG. 6).

```
Primer B4904
                                       (SEQ ID NO: 35)
5'-gataCTCGAGGATCTAGTCAAAAGCCTCCGACCGGAGGCTTTTGACT
ttagtacttgccgcctag-3'

Primer B4270
                                       (SEQ ID NO: 36)
5'-gataccATGGcaaattatcaaaacgcatc-3'

Primer B4271
                                       (SEQ ID NO: 37)
5'-gataCCATggTAGTTCCTCGATAAGTCG-3'

Primer B4905
                                       (SEQ ID NO: 38)
5'-gataCCTAGGCCTAGGgatctGACCGACCGATCTACTCC-3'
```

3. pSMX253 (FIG. 6), comprising pSMX252 containing lacZα, may be constructed as follows.

lacZα may be PCR amplified using primers B4906 and B4907 (FIG. 6). The resulting PCR product may then be digested with XhoI and ligated to pSMX252 that has also been digested with XhoI and treated with alkaline phosphatase prior to ligation, to yield pSMX253 (FIG. 6).

Primer B4906 consists of a 5' XhoI restriction site (underlined), followed by sequence complementary to the 3' end of lacZα (FIG. 6). Primer B4907 consists of a 5' XhoI restriction site (underlined), followed by sequence of the lac promoter driving expression of lacZα (FIG. 6).

```
Primer B4906
                                       (SEQ ID NO: 39)
5'-gataCTCGAGttagcgccattcgccattc-3'

Primer B4907
                                       (SEQ LD NO: 40)
5'-gataCTCGAGgcgcaacgcaattaatgtg-3'
```

Genetic Modification of Phi33, PTPX83, PTPX84, and Similar Phage, to Introduce rpsB-SASP-C and lacZα

1. Plasmid pSMX253 (FIG. 6; FIG. 3; FIG. 4; FIG. 7) may be introduced into *P. aeruginosa* strain PAX21 by conjugation, selecting transconjugants on the basis of tetracycline resistance (50 µg/ml), yielding strain PTA51.

2. Strain PTA51 may be infected in individual experiments with phage Phi33, or PTPX83, or PTPX84, or other similar phage, and the progeny phage harvested.

3. Recombinant phage, in which rpsB-SASP-C and lacZα have been introduced into the chosen insertion site, may be identified by plaquing the lysate from step (2) on *P. aeruginosa* strain PAX21, onto medium containing S-gal, looking for black plaques, which are indicative of β-galactosidase activity.

4. PCR may be carried out to check that rpsB-SASP-C and lacZα are present.

5. Following identification of verified isolates (for example, PTPX85 (FIG. 7), PTPX86 (FIG. 3), PTPX87 (FIG. 4)), the isolates may be plaque purified twice more on *P. aeruginosa* strain PAX21, prior to further use.

Genetic Modification to Remove the lacZα Marker from PTPX85, PTPX86, PTPX87, and Similar Derivatives of Phi33

1. Plasmid pSMX252 (FIG. 6; FIG. 3; FIG. 4; FIG. 7) may be introduced into *P. aeruginosa* strain PAX21 by conjugation, selecting transconjugants on the basis of tetracycline resistance (50 µg/ml), yielding strain PTA85.

2. Strain PTA85 may be infected in individual experiments with phage PTPX85, or PTPX86, or PTPX87, or other similar phage, and the progeny phage harvested.

3. Recombinant phage, in which lacZα marker has been removed, may be identified by plaquing the lysate from step (2) on *P. aeruginosa* strain PAX21, onto medium containing S-gal, looking for white plaques, which are indicative of loss of β-galactosidase activity.

4. PCR may be carried out to confirm removal of the lacZα marker, while ensuring that rpsB-SASP-C is still present.

5. Following identification of verified isolates (for example, PTPX88 (FIG. 7), PTPX89 (FIG. 3), PTPX90 (FIG. 4)), the isolates may be plaque purified twice more on *P. aeruginosa* strain PAX21, prior to further use.

Construction of a plasmid to introduce fda-SASP-C(codon optimised) and lacZα into a chosen insertion site, located in an intergenic region immediately downstream of the tail fibre operon, within the genome of Phi33, PTPX83, PTPX84, and similar phage 1. Plasmid pSMX254 (FIG. 8), comprising pSMX251 containing SASP-C codon optimised for expression in *P. aeruginosa*, under the control of an fda promoter, may be constructed as follows.

The SASP-C gene from *Bacillus megaterium* strain KM (ATCC 13632) may be codon optimised for expression in *P. aeruginosa* (FIG. 9) and synthesised in vitro. The codon optimised SASP-C gene may then be amplified by PCR using primers B4312 and B4313 (FIG. 8). The fda promoter may be amplified by PCR from *P. aeruginosa* using primers B4314 and B4315 (FIG. 8). The resulting two PCR products may then be joined by splicing by overlap extension (SOEing) PCR, using the outer primers B4312 and B4314 (FIG. 8). The resulting fda-codon optimised SASP-C-terminator PCR product may then be digested with XhoI and AvrII, cleaned, and ligated to pSMX251 that has been digested with XhoI and AvrII, yielding plasmid pSMX254 (FIG. 8).

Primer B4312 comprises a 5' XhoI restriction site, followed by a bi-directional transcriptional terminator, and then sequence complementary to the 3' end of the SASP-C gene from *B. megaterium* strain KM (ATCC 13632) that has been codon optimised for expression in *P. aeruginosa* (underlined, in bold; FIG. 8). Primer B4313 comprises sequence of the 3' end of the fda promoter from *P. aeruginosa* PAO1 (in bold) followed by sequence of the 5' end of the codon optimised SASP-C gene. Primer B4314 comprises sequence complementary to the 5' end of the codon optimised SASP-C gene followed by sequence complementary to the 3' end of the fda promoter from *P. aeruginosa* PAO1 (FIG. 8). Primer B4315 comprises a 5' AvrII restriction site (underlined), followed by sequence of the beginning of the fda promoter from *P. aeruginosa* PAO1 (FIG. 8).

```
Primer B4312
                                      (SEQ ID NO: 41)
5'-gataCTCGAGAGTCAAAAGCCTCCGACCGGAGGCTTTTGACTTCAGT

ACTTGCCGCCCAG-3'

Primer B4313
                                      (SEQ ID NO: 42)
5'-GATTGGGAGATACGAGAACCATGGCCAACTACCAGAACGC-3'

Primer B4314
                                      (SEQ ID NO: 43)
5'-GCGTTCTGGTAGTTGGCCATGGTTCTCGTATCTCCCAATC-3'

Primer B4315
                                      (SEQ ID NO: 44)
5'-GATACCTAGGAACGACGAAGGCCTGGTG-3'
```

3. pSMX255 (FIG. 8), comprising pSMX254 containing lacZα, may be constructed as follows.

lacZα may be PCR amplified using primers B4906 and B4907 (FIG. 8). The resulting PCR product may then be digested with XhoI and ligated to pSMX254 that has also been digested with XhoI and treated with alkaline phosphatase prior to ligation, to yield pSMX255 (FIG. 8).

Primer B4906 consists of a 5' XhoI restriction site (underlined), followed by sequence complementary to the 3' end of lacZα (FIG. 8). Primer B4907 consists of a 5' XhoI restriction site (underlined), followed by sequence of the lac promoter driving expression of lacZα (FIG. 8).

```
Primer B4906
                                      (SEQ ID NO: 40)
5'-gataCTCGAGttagcgccattcgccattc-3'

Primer B4907
                                      (SEQ ID NO: 41)
5'-gataCTCGAGgcgcaacgcaattaatgtg-3'
```

Genetic Modification of Phi33, PTPX83, PTPX84, and Similar Phage, to Introduce Fda-Codon Optimised SASP-C and lacZα

1. Plasmid pSMX255 (FIG. 8; FIG. 10; FIG. 11; FIG. 12) may be introduced into *P. aeruginosa* strain PAX21 by conjugation, selecting transconjugants on the basis of tetracycline resistance (50 μg/ml), yielding strain PTA86.

2. Strain PTA86 may be infected in individual experiments with phage Phi33, or PTPX83, or PTPX84, or other similar phage, and the progeny phage harvested.

3. Recombinant phage, into which fda-codon optimised SASP-C and lacZα have been introduced, may be identified by plaquing the lysate from step (2) on *P. aeruginosa* strain PAX21, onto medium containing S-gal, looking for black plaques, which are indicative of β-galactosidase activity.

4. PCR may be carried out to check that fda-codon optimised SASP-C and lacZα are present.

5. Following identification of verified isolates (for example, PTPX91 (FIG. 12), PTPX92 (FIG. 10), PTPX93 (FIG. 11)), the isolates may be plaque purified twice more on *P. aeruginosa* strain PAX21, prior to further use.

Genetic Modification to Remove the lacZα Marker from PTPX91, PTPX92, PTPX93, and Similar Derivatives of Phi33

1. Plasmid pSMX254 (FIG. 8; FIG. 10; FIG. 11; FIG. 12) may be introduced into *P. aeruginosa* strain PAX21 by conjugation, selecting transconjugants on the basis of tetracycline resistance (50 μg/ml), yielding strain PTA87.

2. Strain PTA87 may be infected in individual experiments with phage PTPX91, or PTPX92, or PTPX93, or other similar phage, and the progeny phage harvested.

3. Recombinant phage, in which lacZα marker has been removed, may be identified by plaquing the lysate from step (2) on *P. aeruginosa* strain PAX21, onto medium containing S-gal, looking for white plaques, which are indicative of loss of β-galactosidase activity.

4. PCR may be carried out to confirm removal of the lacZα marker, while ensuring that fda-codon optimised SASP-C is still present.

5. Following identification of verified isolates (for example, PTP387 (FIG. 12), PTP388 (FIG. 10), PTP389 (FIG. 11)), the isolates may be plaque purified twice more on *P. aeruginosa* strain PAX21, prior to further use.

REFERENCES

Abedon S T. (2008). Bacteriophage Ecology: Population Growth, Evolution, an Impact of Bacterial Viruses. Cambridge. Cambridge University Press. Chapter 1.

Boucher, H. W., Talbot, G. H., Bradley, 1 S., Edwards, J. E., Gilbert, D., Rice, L. B., & Bartlett, J. (2009). Bad bugs, no drugs: no ESKAPE! An update from the Infectious Diseases Society of America. *Clinical Infectious Diseases*, 48: 1-12.

Burrowes, B., & Harper, D. R. (2012). Phage Therapy of Non-wound Infections. *Bacteriophages in Health and Disease: Bacteriophages in Health and Disease*, Chapter 14: 203-216.

Carlton, R. M. (199 Phage therapy: past history and future prospects. *Archivum Immunologiae et Therapiae Experimentalis-English Edition* 47:267-274.

Ceyssens P, Miroshnikov K, Mattheus W, Krylov V. Robben J, Noben J, Vanderschraeghe S, Sykilinda N, Kropinski A M, Volckaert G, Mesyanzhinov V, Lavigne R. (2009). Comparative analysis of the widespread and conserved PB1-like viruses infecting *Pseudomonas aeruginosa*. *Env. Microbiol.*. 11:2874-2883.

Francesconi, S. C., MacAlister, T. J., Setlow, B., & Setlow, P. (1988). Immunoelectron microscopic localization of small, acid-soluble spore proteins in sporulating cells of *Bacillus subtilis* Bacterial., 170: 5963-5967.

Frenkiel-Krispin, D., Sack, R., Englander, J., Shimoni, E., Eisenstein, M., Bullitt, E. & Wolf, S. G. (2004. Structure of the DNA-SspC complex: implications for DNA packaging, protection, and repair in bacterial spores. *J. Bacteriol.* 186:3525-3530.

Gill J J, Hyman P. (2010). Phage Choice, Isolation and Preparation for Phage therapy. *Current Pharmaceutical Biotechnology.* 11:2-14.

Kutateladze, M., & Adamia., R. (2010). Bacteriophages as potential new therapeutics to replace or supplement antibiotics. *Trends Biotechnol.* 28:591-595, Lee, K. S., Bumbaca, D., Kosman, J., Setlow, P., &. Jedrzejas, M. J. (2008). Structure of a protein-DNA complex essential for DNA protection in spores of *Bacillus* species. *Proc. Nail Acad. Sci.* 1.05:2806-2811.

Nicholson W L, Setlow B, Setlow P. (1990). Binding of DNA in vitro by a small, acid-soluble spore protein from *Bacillus subtilis* and the effect of this binding on DNA topology. *J Bacteriol.* 172:6900-6906.

Rakhuba D V, Kolomiets E I, Szwajcer Dey E, Novik E I (2010). Bacteriophage Receptors, Mechanisms of Phage Adsorption and Penetration into Host Cell. *Polish J. Microbiol.* 59:145-155.

Sambrook, J., Fritsch. E. F., & Maniatis, T. (1989 *Molecular cloning*(Vol. 2, pp. 14-9). New York: Cold Spring Harbor Laboratory Press.

Scholl, D., Rogers, S., Adhya, S. Merril, C. R. (2001). Bacteriophage K1-5 encodes two different tail fiber proteins, allowing it to infect and replicate on both K1 and K5 strains of *Escherichia coli. J. virol.* 75:2509-7515, Veesler D, Cambillau C. (2011). A Common Evolutionary Origin for Tailed-Bacteriophage Functional Modules and Bacterial Machineries. *Microbiol Mol Biol Rev.* 75:423-433.

Walker, B., Barrett, S., Polasky, S., Galaz, V., Folke, C., Engstrom. G., & de Zeeuw, A. (2009). Looming global-scale failures and missing institutions., *Science,* 325: 1345-1346.

WHO (2014) Antimicrobial resistance: global report on surveillance 2014.

---

What is claimed is:

1. A composition comprising:
   (i) an anti-bacterially effective amount of at least one isolated modified lytic bacteriophage capable of infecting multiple different target bacteria, which at least one bacteriophage is modified to comprise:
   (a) a toxin gene encoding a toxin protein which is toxic to the target bacteria,
   wherein said toxin gene comprises an α/β small acid-soluble spore protein (SASP) gene, and
   (b) to express one or more host range determinant proteins which are not naturally present in the bacteriophage which confer multiple bacterial host specificities, wherein the host range determinant proteins comprise tail fibre proteins, and each tail fibre protein comprises a receptor binding region for binding to the target bacteria and a region linking the receptor binding region to the body of the bacteriophage; and
   (ii) a pharmaceutically acceptable carrier;
   wherein said composition is capable of inhibiting the growth of said target bacteria when administered to a subject infected with said target bacteria and/or when applied to an environment comprising said target bacteria.

2. A composition comprising a modified lytic bacteriophage according to claim 1, wherein the SASP gene encodes SASP-C, or the SASP-C from *Bacillus megaterium*.

3. A composition comprising a modified lytic bacteriophage according to claim 1, wherein the modified lytic bacteriophage is capable of infecting multiples-different target bacteria bacterial within the same bacterial species.

4. A composition comprising a modified lytic bacteriophage according to claim 1, wherein the toxin gene is under the control of a constitutive promoter or is under the control of a constitutive promoter selected from pdhA, rpsB, pgi, fda, and lasB promoters.

5. A composition comprising a modified lytic bacteriophage according to claim 1, wherein at least one of the target bacteria is *Pseudomonas*, or wherein the multiple different target bacteria all comprise different *Pseudomonas* bacteria, or wherein the target *Pseudomonas* bacteria comprise *Pseudomonas aeruginosa*.

6. A composition comprising a modified lytic bacteriophage according to claim 1, wherein the receptor binding region of the tail fibre protein is a C-terminal region and the region linking the C-terminal receptor binding region to the body of the bacteriophage is an N-terminal region wherein the N-terminal region comprises amino acids 1 to 628 of the tail fibre protein and the C-terminal region comprises amino acids 629 to 964 of the tail fibre of bacteriophage Phi33 (SEQ ID NO: 50) and:

(a) the C-terminal region has 57-96% amino acid sequence identity with the C-terminal region of bacteriophage Phi33 and/or
   (b) the C-terminal region is from any one of bacteriophage Phi33, LBL3, SPM-1, F8, PB1, KPP12, LMA2, SN, 14-1, JG024, NH4, PTP47, PTP92, C36 and PTP93 (SEQ ID NOs: 45-58); and/or
   (c) the C-terminal region has 57-80% amino acid sequence identity with the C-terminal region of bacteriophage Phi33; and/or
   (d) the N-terminal region has at least 95% amino acid sequence identity with the N-terminal region of bacteriophage Phi33; and/or
   (e) the N-terminal region is from any one of bacteriophage Phi33, LBL3, SPM-1, F8, PB1, KPP12, LMA2, SN, 14-1, JG024, NH4, PTP47, PTP92, C36 and PTP93 (SEQ ID NOs: 45-58); and/or
   (f) the tail fibre protein is from bacteriophage PTP387.

7. A composition comprising one or more modified lytic bacteriophage according to claim 1, wherein the host range determinant proteins comprise hybrid tail fibre proteins comprising a C-terminal receptor binding region and an N-terminal region linking the C-terminal receptor binding region to the body of the bacteriophage, wherein the C-terminal and N-terminal regions are each from a different bacteriophage and/or each hybrid tail fibre protein comprises the C-terminal receptor binding region of bacteriophage PTP47 and the N-terminal region of bacteriophage Phi33; and/or each hybrid tail fibre protein comprises the C-terminal receptor binding region of bacteriophage PTP92 and the N-terminal region of bacteriophage Phi33.

8. A composition comprising one or more modified lytic bacteriophages according to claim 1, which bacteriophages comprise a tail fibre protein from a bacteriophage selected from one or more of Phi33, LBL3, SPM-1, F8, PB1, KPP12, LMA2, SN, 14-1, JG024, NH4, PTP47, PTP92, C36 and PTP93 (SEQ ID NOs: 45-58).

9. A composition comprising one or more modified lytic bacteriophage according to claim 1 in admixture with at least one other modified lytic bacteriophage which is capable of infecting target bacteria, which also includes a SASP gene encoding a SASP which is toxic to the target bacteria.

10. A composition according to claim 1, which comprises at least two of said modified lytic bacteriophages, wherein at least two of which have different host specificities.

11. A composition according to claim 1, which is formulated for pharmaceutical use, for topical use, or for delivery to the respiratory tract.

* * * * *